(12) United States Patent
Church et al.

(10) Patent No.: US 9,914,939 B2
(45) Date of Patent: Mar. 13, 2018

(54) GENOME ENGINEERING

(71) Applicant: President and Fellows of Harvard College, Cambridge, MA (US)

(72) Inventors: George M. Church, Brookline, MA (US); Luhan Yang, Somerville, MA (US); Marc Guell, Boston, MA (US); Joyce Lichi Yang, Cambridge, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 14/907,605

(22) PCT Filed: Jul. 25, 2014

(86) PCT No.: PCT/US2014/048140
§ 371 (c)(1),
(2) Date: Jan. 26, 2016

(87) PCT Pub. No.: WO2015/013583
PCT Pub. Date: Jan. 29, 2015

(65) Prior Publication Data
US 2016/0369301 A1    Dec. 22, 2016

Related U.S. Application Data

(60) Provisional application No. 61/858,866, filed on Jul. 26, 2013.

(51) Int. Cl.
*C12N 15/90* (2006.01)
*C12N 15/85* (2006.01)
*C12N 5/00* (2006.01)
*C12N 15/86* (2006.01)
*C12N 5/074* (2010.01)

(52) U.S. Cl.
CPC ........ *C12N 15/907* (2013.01); *C12N 5/0696* (2013.01); *C12N 15/85* (2013.01); *C12N 15/86* (2013.01); *C12N 2510/00* (2013.01); *C12N 2740/15043* (2013.01); *C12N 2800/90* (2013.01); *C12N 2830/003* (2013.01)

(58) Field of Classification Search
None
See application file for complete search history.

(56) References Cited

U.S. PATENT DOCUMENTS

2011/0301073 A1    12/2011    Gregory et al.
2013/0137160 A1    5/2013     Zhang et al.

OTHER PUBLICATIONS

Gaj et al. ZFN, TALEN, and CRISPR/Cas-based methods for genome engineering Trends Biotechnol May 9, 2013 vol. 31 No. 7 pp. 397-405. Especially abstract, p. 399 col. 1 para 2, p. 398 col. 1 para 2. p. 399 fig 1c,d; p. 401 table 1, p. 402 box 2.
Holkers et al. Differential integrity of TALE nuclease genes following adenoviral and lentiviral vector gene transfer into human cells. Nucleic Acids Res Dec. 28, 2012 vol. 41 No. 5, pp. e63 1-14. Especially p. 2 col. 2 para 2, p. 3 col. 2 para 3, p. 5 col. 2 para 2, p. 9 col. 2 para 2 and para 3, p. 10 col. 2 para 4, p. 13 col. 1 para 1.

*Primary Examiner* — Addison D Ault
(74) *Attorney, Agent, or Firm* — Banner & Witcoff, Ltd.

(57) ABSTRACT

Methods of genome engineering in cells using a TALEN lacking repeat sequences or Cas9 is provided.

21 Claims, 40 Drawing Sheets tGFP Donor

Chromosomal reporter

SEQ ID NO: 1

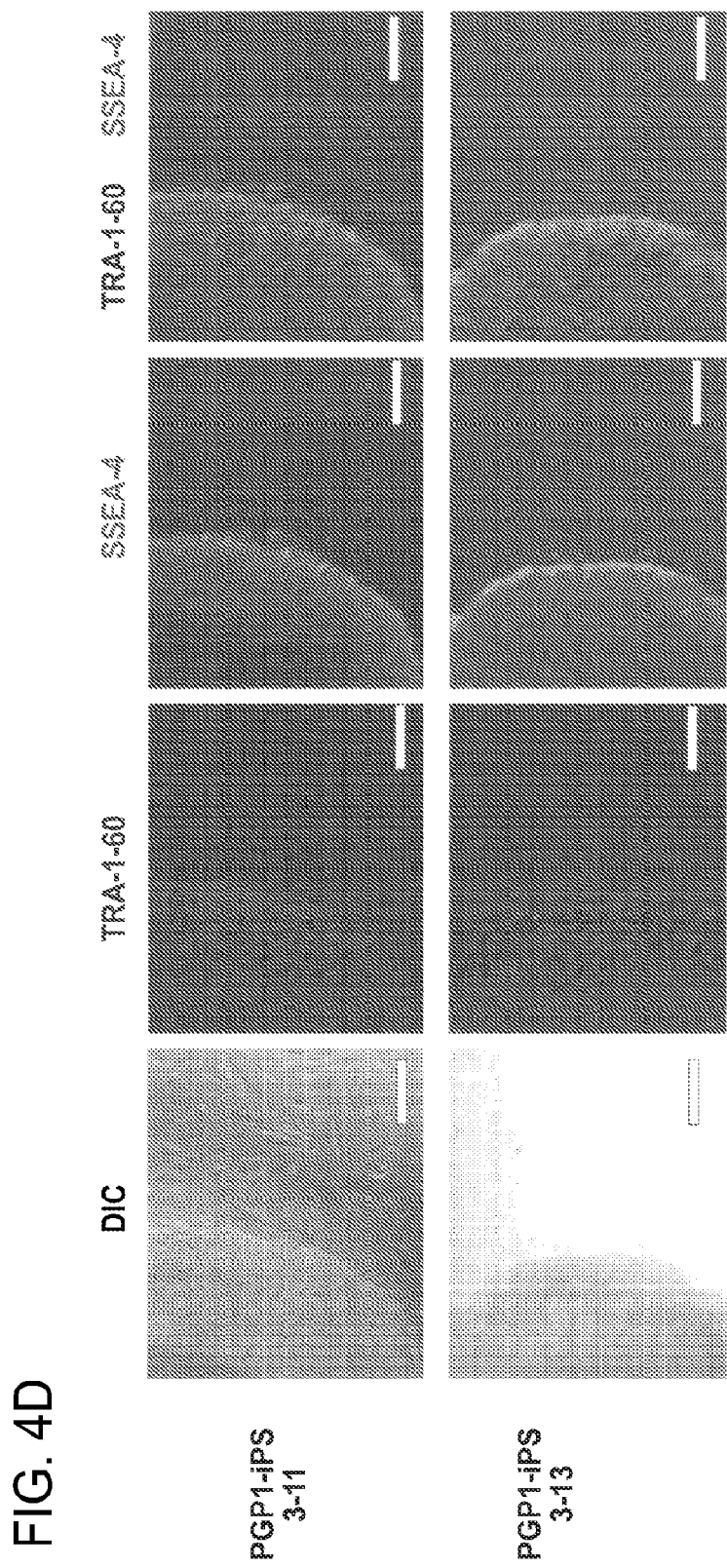

FIG. 5A

```
         L  T  P  E  Q  V  V  A  I  A  S  X  X  G  G  K  Q  A  L  E  T  V  Q  R  L  L  P  V  L  C  Q  A  H  G
TALE-MM  CTAACCCCAGAGCAAGTCGTGGCAATCGCTCNNNNNNGCGGAAAACAGGCATTGAAACAGTACAGCGGCTGCTGCCGGTGCTGTGCCAAGCGCACGGA
reTALE-M1  CTAACCCCTGAACAGTAGTCGTCGCCTATAGTTCANNNNNNNGCGGAAGCAACCAAGCACTTGAGACCACTTCAACGCACTCTGCCAGTGCTCCTGCCAAGCCCATGGA
reTALE-M2  TTGACTCCGGAGCAAGTCGTCGCCATCGCGAGCNNNNNNNGGGGGGAAGCAGGCGCTGAAACTGTTCAGAGACTTGCTGCCTACTTTGTCAGGCGATGGT
reTALE-M3  CTCACCCCGAACAGTTGTCGCAATAGCAAGTNNNNNNNGGGGTAAGCAAGCCCTAGAGACTGTGCAACCGTGCTGCCCCTGCTGTGTCAGGCTCACGGT
reTALE-M4  CTGACACCTGAACAAGTGTCGCGATAGCCAGTNNNNNNNGCGGGAAAACAAGCTTAGAAACCGTTCAAAGGTTGTGCCGTTCTGTGCCAAGCACATGGG
reTALE-M5  TTAACACCCAGAACAAGTAGTAGCGATAGCNNNNNNNGTGANNNNNNGGGGTAAACAGGCTTTGAGAGACGGTACAGCGGTGGTTATTGCCTCCTGCCAGGCCCACGGA
reTALE-M6  CTTACGCCAGAACAGTGGTTGCAATTGCCTTCNNNNNNNGCCGGAAACAAGCGTTGAAACAGTGCAGAGACTGTCCAGAGACTCCTTCCTTTTGTGTCAAGCCACGGC
reTALE-M7  TTGACGCCTGAGCAGTTGTGCCATCGCNNNNNNNGGGAGGAAGCAGGCTCTTGAAACCGTAGACGAGTTCAGCGCTTGCTCCCGGCTACTCGTCAGGCACATGGT
reTALE-M8  CTAACCCCCAGCAGTAGTTGCCATAGCAAGTNNNNNNNCCGGCAAACAGGCCATTAGAAACAGGATTCAGACCATCAGACAGTCAGACAGTCCAGTCGTCTTCCTGTGTTATGCCAAGCACACGGC
reTALE-M9  CTAACTCCGGAACAGTCGTCGCCTAGCCAGTTCCTTGCCATCGCCAGTNNNNNNGCGGCAAGCAGGCGCTAGAGACTCTCGAAACAGTCAGACAGCAAGCTCGAGACTTCGAAACAGTACAGCGGCTGTTGCCAGTCCTATGTCAAGCTCATGGA
reTALE-M10 CTCACCCCGGAGCAGTCGTCGCAATCGCATCNNNNNNNGCGGCAAGCAGGCAAGCTCCGAAACAGTCGAGAGATTGTTACCGTACTGCCTGTCTACTATGCCAAGCCATGGT
reTALE-M11 CTGAGCCCTGAGCAGTCGTGGCAGTAGTGCAAATGCCAATNNNNNNNGGAGGTAAACAAGCACTTCCTTGGAAACAGGCCCTTGGAAACAGGCTCCCGGAAAGATGTCTCCCAGTGTCTTCCTGTCGTTCTTTGCCAAGCCATGGC
reTALE-M12 TTAACCCCAGAGCAAGTCGTCGCAATAGCAAGTGTGATNNNNNNNGGGGTGCAAGCAGGCCCTGGAAACAGGCACTGGAGACCCTGACACGTCCGTCCCCAGTACTCCTTGGTTCTTTGCCCAGGCTCAAGCACACGGG
reTALE-M13 CTTACTCCTGAGCAGTCGTGGCTAGCTATCGCCAGCNNNNNNNGGTGGAAACAGGCTGGGAAACAGGGAGCCAAGCACTGGAAGCCCAACGCCTAAGCGGTTAAGCACACGCTACACGGG
reTALE-M14 TTGCACCCGGAACAAGTGGTGGCGTCGCAATAGCAAGTGCTGCNNNNNNNGGTAAGCAGGCTCCGATTGCGTCCCNNNNNNGGAGGCAGCAAGCAGGCACTGGAGGCACTGGAACGCCTATCGCCAGCACCGTCTTCTTGCCAGGCTCATGGG
reTALE-M15 CTCACGCCAGAGCAGGTGGTACAATAGCGTCGNNNNNNNGGTCGAAGCACCAGCCACATGGCTGTTAAGCAGGCGTTGAAACGGCTTGAAACGGCTTGAAACGCTTGAAGCACATGGCTGCGCCAGGCACACGGA
reTALE-M16 TTGCACCCGGAACAAGTGGTTGCTATTGCTAGTNNNNNNNCGTGNNNNNNGGTCGAAAGCAGGCCCCCGAGACGGTGCGAGAGGTTACTTCCCCTCCTGTCAAGGCACGGC
reTALE-M17 CTCACTCCAGAGCAAGTGGTTGCGATCGCTTCANNNNNNNGTGGAAGACCTGCCCTGGAA
```

SEQ ID NOS: 2-19

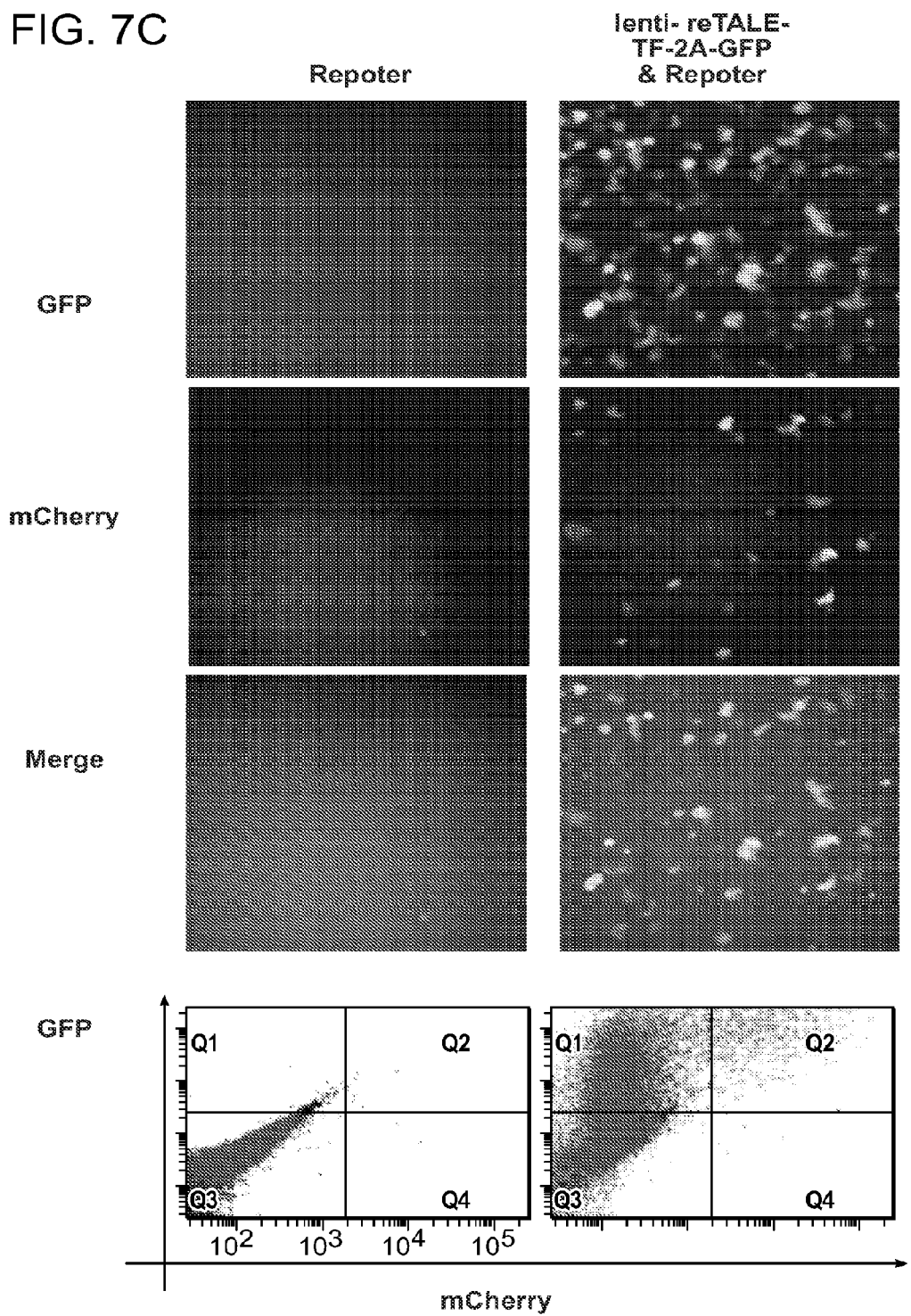

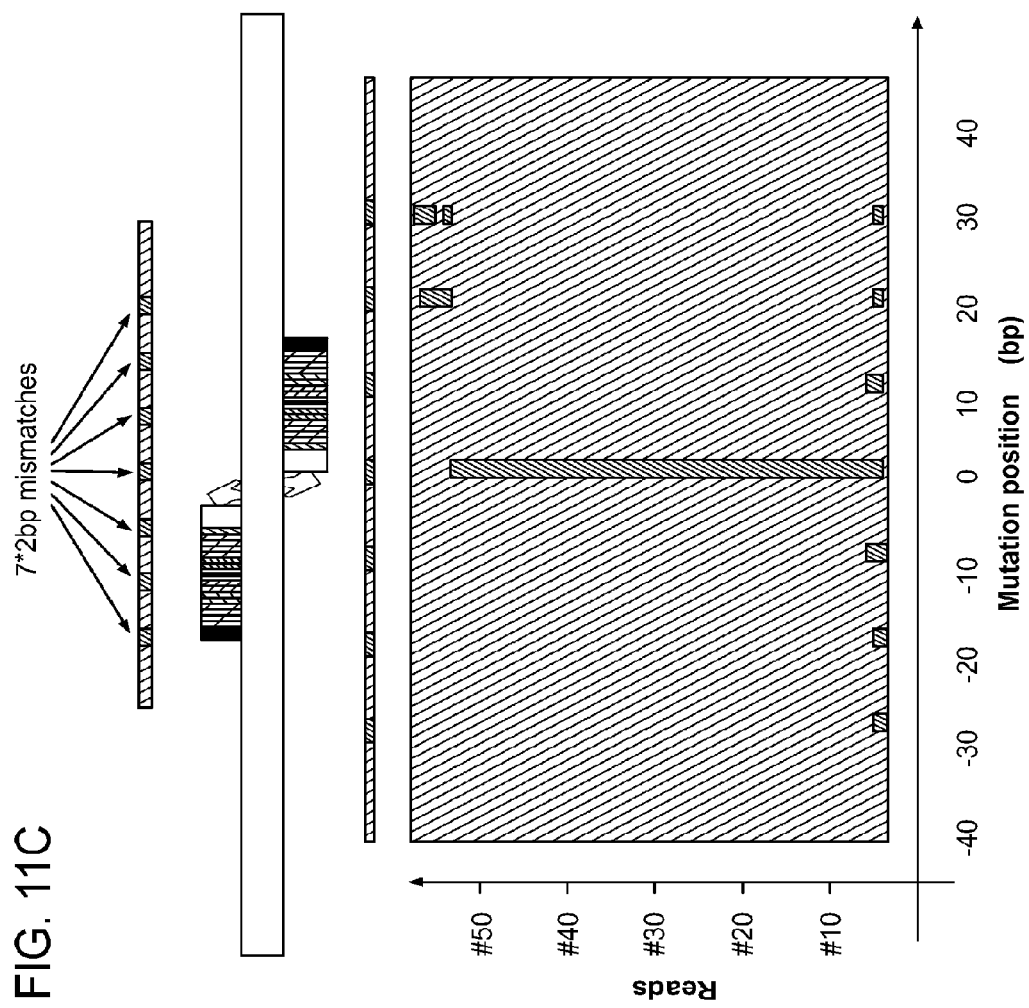

FIG. 20A   SEQ ID NO: 20 re-TALEN-backbone sequence (purple: re-TALE-N; red: SapI site; green: 0.5 monomer; blue: re-TALEN-C; orange: FokI)

ATGTCGCGGACCCGGCTCCCTTCCCCACCCGCACCCAGCCCAGCGTTTTCGGCGAC
TCGTTCTCAGACCTGCTTAGGCAGTTCGACCCCTCACTGTTAACACATCGTTGTTCG
ACTCCCTTCCTCCGTTTGGGGCCACCATACGGAGGCGCCACCGGGAGTGGGAT
GAGGTGCAGTCGGGATTGAGAGCTGCGGATGCACCACCCCAACCATGCGGGTGGC
CGTCACCGCTGCCCGACCGCGAGGGCGAAGCCCGCACCAAGGCGAGGGCAGCGC
AACCGTCCGACGCAAGCCCCGCAGCGCAAGTAGACTTTGGGATATTCA
CAGCAGCAGGAAAAGATCAAGCCCAAAGTGAGGTCGACAGTCGCGCAGCATC
ACGAAGCGCTGGTGGGTCATGGGTTTACACATGCCCACATCGTAGCCTTGTCGCAGC
ACCCTGCAGCCCTTGGCACGGTCGCCGTCAAGTACCAGGACATGATTGCGGCGTTGC
CGGAAGCCACACATGAGGCGATCGTCGTCGGTGTGGGAAACAGTGGAGCGGAGCCCG
AGCGCTTGAGGCCCTGTTGACGGTCGCGGGAGAGCTGAGAGGGCCCTCCCCTTCAGC
TGGACACGGGCCAGTTGCTGAAGATCGCGAAGCGGGAGGAGTCACGGCGGTCGAG
GCGGTGCACGCGTGGCGCAATGCGCTCACGGGAGCACCCCTCAACAGTTCACGTG
ACAGAGACCGCGGCCGCGCATTAGGCACCCCAGCTTTACACTTTATGCTTCCGGCTCG
TATAA-GTGTGGAT-TTGAGT-TAGGATCCGTCGAGATTTCAGGAGCTAAGGAAGCT
AAATGGAGAAAAAATCACTGGATATACCACCGTTGATATATCCCAATGGCATCG
TAAAGAACATTTGAGGCATTTCAGTCAGTTGCTCAATGTACCTATAACCAGACCGT
TCAGC-GGATATTACGGCCTTTTTAAAGACCGTAAAGAAAAATAAGCACAAGTTTTA
TCCGGCCTTTATTCACATTCTTGCCCGCCTGATGAATGCTCATCCGGAATTCCGTATG
GCAATGAAAGACGG-GAGCTGGTGATATGGGATAGTGTTCACCCCTTTGTTACACCGTT

FIG. 20B    SEQ ID NO: 20

```
TTCCATGAGCAAACTGAAACGTTTCATCGCTCTGGAGTGAATACCACGACGATTTC
CGGCAGTTCTACACATATATTCGCAAGATGTGGCGTGTTACGGTGAAAACCTGGCC
TATTCCCTAAAGGGTTTATTGAGAATATGTTTTCGTCTCAGCCAATCCCTGGGTGA
GTTTCACCAGTTTTGATTAAACGTGGCCAATATGGACAACTTCTTCGCCCCGTTTT
CACCATGGGCAAATATTATACGCAAGGCGACAAGGTGCTGATGCCGCTGGCGATTC
AGGTTCATCATGCCGTTTGTGATGGCTTCCATGTCGGCAGAATGCTTAATGAATTAC
AACAGTACTGCGATGAGTGGCAGGGCGGGCGTAAAGATCTGGATCCGGCTTACTA
AAAGCCAGATAACAGTATGCGTATTTGCCGCGCTGATTTTGCGGTATAAGAATATAT
ACTGATATGTATACCCGAAGTATGTCAAAAAGAGGTATGCTATGAAGCAGCGTATT
ACAGTGACAGTTGACAGCGACAGCTATCAGTTGCTCAAGGCATATATGATGTCAATA
TCTCCGGTCTGGTAAGCACAACCATGCAGAATGAAGCCCGTCGTCTGCCGAAC
GCTGGAAAGCGGAAAATCAGGAAGGGATGGCTGAGGTCGCCCGGTTTATTGAAATG
AACGGCTCTTTTGCTGACGAGAACAGGGCTGGTGAAATGCAGTTTAAGGTTTACAC
CTATAAAAGAGAGAGCCGTATCGTCTGTTTGTGAGTACAGAGTGATATTATTGA
CACGCCCGGGCGACGGATGGTGATCCCCCTGGCCAGTGCACGTGCTGTCAGATA
AAGTCTCCCGTGAACTTTACCCGGTGGTGCATATCGGGGATGAAAGCTGGCGATGA
TGACCACCGATATGCCAGTGTGCCGGTCTCCGTTATCGGGGAAGAAGTGGCTGATC
TCAGCCACCGCGAAATGACATCAAAAACGCCATTAACTTGATGTTCTGGGAATA
TAAATGTCAGGCTCCCTTATACACAGCCAGTCTGCAGGTCGACGGTCTCGACGGTCTCG GCTCTTCG
AAGGTTACTTCCCGTCCCTCCTCTGTCAAGCGCCCCTCACTCCAGAGCAAGTGGTTGC
GATCGCTTCAAACAACGGTGAAGACCCTGCCCGGAATCAATCGTGGCCCAGCTTTC
```

FIG. 20C   SEQ ID NO: 20

GAGGGCCGGACCCCGCGCTGGCCGGCACTCACTAATGATCATCTTGTAGGCGCTGGCCTG
CCTCGGGGACGACCCGCCCTTGGATGCGGTGAAGAAGGGGCTCCCGCACGCGCCTG
CATTGATTAAGCGGACCAACAGAAGGATTCCCGAGGAGGACATCACATCGAGTGGCA
GGTTCCAACTCGTGAAGAGTGAACTTGAGGAGAAAAGTCGAGCTGCGGCACAA
ATTGAAATACGTACCGCATGAATACATCGAACTATCGAAATTGCTAGGAACTCGAC
TCAAGACAGAATCCTTGAGATGAAGGTAATGGAGTTCTTTATGAAGTTTATGGATA
CCGAGGAAGCATCTCGGTGGATCACGAAAACCCGACGGAGCAATCTATACGGTGG
GGAGCCCGATTGATTACGGAGTGATCGTCGACAGAAAGCCTACAGCGGTGGGTAC
AATCTTCCCATCGGGCAGGCAGATGAGAATCAACGTTATGTCGAAGAAAATCAGAC
CAGGAACAAACACATCAAATCAAATGAGTGTATCCTTCATCAGTGA
CCGAGTTTAAGTTTTTGTTTGTCTCGGGCATTCAAAGGCAACTATAAGGCCCAGCT
CACACGGTTGAATCACATTACGAACTGCAATGGCGCGGTTTTGTCCGTAGAGGAACT
GCTCATTGGTGGAGAAATGATCAAAGCGGGAACCTGACACTGAAGAAGTCAGAC
GCAAGTTTAACAATGGCGAGATCAATTCCGC re-TALE-TF backbone sequence      SEQ ID NO: 21

(purple: re-TALE-N; red: SapI site; green: 0.5 monomer; blue: re-TALEN-C; orange: NLS-VP64; 2A-GFP is highlighted in green)

ATGTCGCGGGACCCGGCTCCCTTCCCCACCCGACACCCAGCCCAGCGTTTCGGCCGAC
TCGTTCTCAGACCTGCTTAGGCAGTTCGACCCCTCACTGTTTAACACATCGTTGTTCG

FIG. 20D    SEQ ID NO: 21

ACTCCCTTCCTCCGTTTGGGGCGCACCATACGGAGGCGGCCACCCGGGGAGTGGGAT
GAGGTGCAGTCGGGATTGAGAGCTGCGGATGCACCACCCCCAACCATGCGGGTGGC
CGTCACCGCTGCCCGACCGCCGAGGGCGAAGCCGAAGCCCGCCAAGGCGGAGGCAGCGC
AACCGTCCGACGCAAGCCCCGCAGCGCAGCGCAAGTAGATTTGAGAACTTTGGGATATTCA
CAGCAGCAGGAGGAAAAGATCAAGCCCAAAGTGAGGTCGACAGTCGCGCAGCATC
ACGAAGCGCTGGTGGGTCATGGGTTTACACATGCCCACATCGTAGCCTTGTCGCAGC
ACCCTGCAGCCCTTGGCACGGTCGCCGTCAAGTACCAGGACATGATTGCGGCGTTGC
CGGAAGCCACACATGAGGGCGATCGTCGGTGTGGGGAAACAGTGGAGCGGAGCCCG
AGCGCTTGAGGCCCTGTTGACGGTGCGCGGGAGAGCTGAGAGGGCCTCCCCTTCAGC
TGGACACGGGCCAGTTGCTGAAGATCGCGAAGCGGGGAGGAGTCACGGCGGTCGAG
GCGGTGCACGCGTGCGCGCAATGCGCTCACGGGAGCACCCCTCAACAGTTCACGCTG

ACAGAGACCGCGCGGCCGCATTAGGCACCCCAGGCTTTACACTTTATGCTTCCGGCTCG
TATAATGTGTGGATTTGAGTTAGGATCCGTCGAGATTTTCAGGAGCTAAGGAAGCT
AAAATGGAGAAAAAATCACTGGATATACCACCGTTGATATATCCCAATGGCATCG
TAAAGAACATTTTGAGGCATTTCAGTCAGTTGCTCAATGTACCTATAACCAGACCGT
TCAGCTGGATATTACGGCCTTTTTAAAGACCGTAAAGAAAAATAAGCACAAGTTTTA
TCCGGCCTTTATTCACATTCTTGCCCGCCTGATGAATGCTCATCCGGAATTCCGTATG
GCAATGAAAGACGGTGAGCTGTGAGCTGGTGATATGGATAGTGTTCACCCTTGTTACACCGTT
TTCCATGAGCAAACTGAAACGTTTTCATCGCTCTGGAGTGAATACCACGACGATTTC
CGGCAGTTTCTACACATATATTCGCAAGATGTGGCGTGTTACGGTGAAAACCTGGCC
TATTTCCCTAAAGGGTTTATTGAGAATATGTTTTTCGTCTCAGCAAGTTTTGCGGGTGA
GTTTCACCAGTTTTGATTTAAACGTGGCCAATATGGACAACTTCTTCGCCCCGTTTT

FIG. 20E    SEQ ID NO: 21

CACCATGGGCAAATATTATACGCAAGGCGACAAGGTGCTGATGCCGCTGGCGATTC
AGGTTCATCATGCCGTTTGTGATGCTTCCATGTCGGCAGAATGCTTAATGAATTAC
AACAGTACTGCGATGAGTGGCAGGGCGGGGCGTAAAGATCTGGATCCGGCTTACTA
AAAGCCAGATAACAGTATGCGTATTTGCGCGCTGATTTTGCGGTATAAGAATATAT
ACTGATATGTATACCCGAAGTATGTCAAAAAGAGGTATGCTATGAAGCAGCGTATT
ACAGTGACAGTTGACAGCGACAGCTATCAGTTGCTCAAGGCATATATGATGTCAATA
TCTCCGTCTGGTAAGCACAACCATGCAGAATGAAGCCCGTCGTCTGCGTGCCGAAC
GCTGGAAAGCGGAAAATCAGGAAGGATGGCTGAGGTCGAAATGCAGTTTAAGTTACAC
AACGGCTCTTTTGCTGACGAGAACACAGGGCTGGTGAAATGCAGTTTAAGTTTACAC
CTATAAAAGAGAGAGCCGTTATCGTCTCTGTTTGTGGATGTACAGAGTGATATATTGA
CACGCCCGGGCGACGGATGGTGATCCCCCCTGGCCAGTGCAACGTCTGCTGTCAGATA
AAGTCTCCCGTGAACTTTACCCGGTGGTGCATATCGGGGATGAAAGCTGGCGCATGA
TGACCACCGATATGGCCAGTGTGCCGGTCTCCGTTATCGGGGAAGAAGTGGCTGATC
TCAGCCACCGCGAAAATGACATCAAAAACGCCATTAACCTGATGTTCTGGGAATA
TAAATGTCAGGCTCCCTTATACACAGCCAGTCTGCAGGCCTCACTCCAGAGCAAGTGGTTGC
AAGGTTACTTCCCGTCCTCTGTCAAGGCGCACGGCCTCACTCCAGAGCAAGTGGTTGC
GATCGCTTCAAACAACGGTGGAAGACCTGCCCCTGGAATCAATCGTGGCCCAGCTTTC
GAGGCCCGACCCCGGGCCTGGCCGCCACTCACTAATGATCATCTTGTAGCGCTGGCCTG
CCTCGGGGACGACCCGGCCTTGGATGCGGTGAAGAAGGGGCTCCCGCACGCCCTG
CATTGATTAAGCGGACCAACAGAAGGATTCCCGAGAGGACATAGCCCAAGAAGAA
GAGAAAGGTGAGGCCAGCGGTTCCGGACGGCTGACGCATTGGACGATTTGATC

FIG. 20F    SEQ ID NO: 21

TGGATATGCTGGGAAGTGACGCCCCTCGATGATTTTGACCTTGACATGCTTGGTTCGG
ATGCCCTTGATGACTTTGACCTTGATTAACTCTAGAGGCAGTGGAGAGGGCAGAGAAGTCTGCTA
ACCTGGACATGCTGATAACTCTAGAGGCAGTGGAGAGGGCAGAGGAAGTCTGCTA
ACATGCGGTGACGTGGAGGAGAATCCTGGCCCAGTGAGCAAGGGCGAGGAGCTGTT
CACCGGGGTGGTGCCCATCCTGGTCGAGCTGGACGGCGACGTAAACGGCCACAAGT
TCAGCGTGTCCGGCGAGGGCGAGGGCGATGCCACCTACGGCAAGCTGACCCTGAAG
TTCATCTGCACCACCGGCAAGCTGCCCGTGCCCTGGCCCACCCTCGTGACCACCCTG
ACCTACGGCGTGCAGTGCTTCAGCCGCTACCCCGACCACATGAAGCAGCACGACTTC
TTCAAGTCCGCCATGCCCGAAGGCTACGTCGAGGAGTTCGAGGGCCACACCCTGGTG
GACCGCAACTACAAGACCCGCGCCGAGGTGAAGTTCGAGGGCGACACCCTGGTGAA
CCGCATCGAGCTGAAGGGCATCGACTTCAAGGAGGACGGCAACATCCTGGGGCACA
AGCTGGAGTACAACTACAACAGCCACAACGTCTATATCATGGCCGACAAGCAGAAG
AACGGCATCAAGGTGAACTTCAAGATCCGCCACAACATCGAGGACGGCAGCGTGCA
GCTCGCCGACCACTACCAGCAGAACACCCCCATCGGCGACGGCCCCGTGCTGCTGC
CCGACAACCACTACCTGAGCACCCAGTCCGCCCTGAGCAAAGACCCCAACGAGAAG
CGCGATCACATGGTCCTGCTGGAGTTCGTGACCGCCGCCGGGATCACTCTCGGCATG
GAGGAGGCTGTACAAAG

```
SEQUENCE LISTING

<160> NUMBER OF SEQ ID NOS: 227

<210> SEQ ID NO 1
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
tggggcaagc ttctg                                                         15

<210> SEQ ID NO 2
<211> LENGTH: 102
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
```

```
<223> OTHER INFORMATION: TALE template
<220> FEATURE:
<221> NAME/KEY: modified_base
<222> LOCATION: (34)..(39)
<223> OTHER INFORMATION: a, c, g or t

<400> SEQUENCE: 2
ctaaccccag agcaggtcgt ggcaatcgcc tccnnnnnng gcggaaaaca ggcattggaa      60
acagtacagc ggctgctgcc ggtgctgtgc aagcgcacg ga                        102

<210> SEQ ID NO 3
<211> LENGTH: 102
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: PCR primer
<220> FEATURE:
<221> NAME/KEY: modified_base
<222> LOCATION: (34)..(39)
<223> OTHER INFORMATION: a, c, g or t

<400> SEQUENCE: 3
ctaacccctg aacaggtagt cgctatagct tcannnnnng ggggcaagca agcacttgag      60
accgttcaac gactcctgcc agtgctctgc aagcccatg ga                        102

<210> SEQ ID NO 4
<211> LENGTH: 102
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: PCR primer
<220> FEATURE:
<221> NAME/KEY: modified_base
<222> LOCATION: (34)..(39)
<223> OTHER INFORMATION: a, c, g or t

<400> SEQUENCE: 4
ttgactccgg agcaagtcgt cgcgatcgcg agcnnnnnng ggggaagca ggcgctggaa       60 actgttcaga gactgctgcc tgtactttgt caggcgcatg gt                        102

<210> SEQ ID NO 5
<211> LENGTH: 102
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: PCR primer
<220> FEATURE:
<221> NAME/KEY: modified_base
<222> LOCATION: (34)..(39)
<223> OTHER INFORMATION: a, c, g or t

<400> SEQUENCE: 5 ctcaccccg aacaggttgt cgcaatagca agtnnnnnng gcggtaagca agccctagag       60
actgtgcaac gcctgctccc cgtgctgtgt caggctcacg gt                        102

<210> SEQ ID NO 6
<211> LENGTH: 102
<212> TYPE: DNA
```

```
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: PCR primer
<220> FEATURE:
<221> NAME/KEY: modified_base
<222> LOCATION: (34)..(39)
<223> OTHER INFORMATION: a, c, g or t

<400> SEQUENCE: 6
ctgacacctg aacaagttgt cgcgatagcc agtnnnnnng ggggaaaaca agctctagaa      60
acggttcaaa ggttgttgcc cgttctgtgc caagcacatg gg                        102

<210> SEQ ID NO 7
<211> LENGTH: 102
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: PCR primer
<220> FEATURE:
<221> NAME/KEY: modified_base
<222> LOCATION: (34)..(39)
<223> OTHER INFORMATION: a, c, g or t

<400> SEQUENCE: 7
ttaacacccg aacaagtagt agcgatagcg tcannnnnng ggggtaaaca ggctttggag      60
acggtacagc ggttattgcc ggtcctctgc caggcccacg ga                        102

<210> SEQ ID NO 8
<211> LENGTH: 102
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: PCR primer
<220> FEATURE:
<221> NAME/KEY: modified_base
<222> LOCATION: (34)..(39)
<223> OTHER INFORMATION: a, c, g or t

<400> SEQUENCE: 8
cttacgccag aacaggtggt tgcaattgcc tccnnnnnng gcgggaaaca agcgttggaa      60
actgtgcaga gactccttcc tgttttgtgt caagcccacg gc                        102

<210> SEQ ID NO 9
<211> LENGTH: 102
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: PCR primer
<220> FEATURE:
<221> NAME/KEY: modified_base
<222> LOCATION: (34)..(39)
<223> OTHER INFORMATION: a, c, g or t

<400> SEQUENCE: 9
ttgacgcctg agcaggttgt ggccatcgct agcnnnnnng gagggaagca ggctcttgaa      60
accgtacagc gacttctccc agttttgtgc caagctcacg gg                        102
```

<210> SEQ ID NO 10
<211> LENGTH: 102
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: PCR primer
<220> FEATURE:
<221> NAME/KEY: modified_base
<222> LOCATION: (34)..(39)
<223> OTHER INFORMATION: a, c, g or t

<400> SEQUENCE: 10 ctaaccccg agcaagtagt tgccatagca agcnnnnnng gaggaaaaca ggcattagaa    60
acagttcagc gcttgctccc ggtactctgt caggcacacg gt                     102

<210> SEQ ID NO 11
<211> LENGTH: 102
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: PCR primer
<220> FEATURE:
<221> NAME/KEY: modified_base
<222> LOCATION: (34)..(39)
<223> OTHER INFORMATION: a, c, g or t

<400> SEQUENCE: 11
ctaactccgg aacaggtcgt agccattgct tccnnnnnng gcggcaaaca ggcgctagag    60
acagtccaga ggctcttgcc tgtgttatgc caggcacatg gc                      102

<210> SEQ ID NO 12
<211> LENGTH: 102
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: PCR primer
<220> FEATURE:
<221> NAME/KEY: modified_base
<222> LOCATION: (34)..(39)
<223> OTHER INFORMATION: a, c, g or t

<400> SEQUENCE: 12
ctcaccccgg agcaggtcgt tgccatcgcc agtnnnnnng gcggaaagca agctctcgaa    60
acagtacaac ggctgttgcc agtcctatgt caagctcatg ga                      102

<210> SEQ ID NO 13
<211> LENGTH: 102
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: PCR primer
<220> FEATURE:
<221> NAME/KEY: modified_base
<222> LOCATION: (34)..(39)
<223> OTHER INFORMATION: a, c, g or t

```
<400> SEQUENCE: 13
ctgacgcccg agcaggtagt ggcaatcgca tctnnnnnng gaggtaaaca agcactcgag    60
actgtccaaa gattgttacc cgtactatgc caagcgcatg gt                      102

<210> SEQ ID NO 14
<211> LENGTH: 102
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: PCR primer
<220> FEATURE:
<221> NAME/KEY: modified_base
<222> LOCATION: (34)..(39)
<223> OTHER INFORMATION: a, c, g or t

<400> SEQUENCE: 14
ttaaccccag agcaagttgt ggctattgca tctnnnnnng gtggcaaaca agccttggag    60
acagtgcaac gattactgcc tgtcttatgt caggcccatg gc                      102

<210> SEQ ID NO 15
<211> LENGTH: 102
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: PCR primer
<220> FEATURE:
<221> NAME/KEY: modified_base
<222> LOCATION: (34)..(39)
<223> OTHER INFORMATION: a, c, g or t

<400> SEQUENCE: 15
cttactcctg agcaagtcgt agctatcgcc agcnnnnnng gtgggaaaca ggccctggaa    60
accgtacaac gtctcctccc agtactttgt caagcacacg gg                      102

<210> SEQ ID NO 16
<211> LENGTH: 102
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: PCR primer
<220> FEATURE:
<221> NAME/KEY: modified_base
<222> LOCATION: (34)..(39)
<223> OTHER INFORMATION: a, c, g or t

<400> SEQUENCE: 16
ttgacaccgg aacaagtggt ggcgattgcg tccnnnnnng gaggcaagca ggcactggag    60
accgtccaac ggcttcttcc ggttctttgc caggctcatg gg                      102

<210> SEQ ID NO 17
<211> LENGTH: 102
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: PCR primer
```

```
<220> FEATURE:
<221> NAME/KEY: modified_base
<222> LOCATION: (34)..(39)
<223> OTHER INFORMATION: a, c, g or t

<400> SEQUENCE: 17
ctcacgccag agcaggtggt agcaatagcg tcgnnnnnng gtggtaagca agcgcttgaa      60
acggtccagc gtcttctgcc ggtgttgtgc caggcgcacg ga                       102

<210> SEQ ID NO 18
<211> LENGTH: 102
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: PCR primer
<220> FEATURE:
<221> NAME/KEY: modified_base
<222> LOCATION: (34)..(39)
<223> OTHER INFORMATION: a, c, g or t

<400> SEQUENCE: 18
ctcacaccag aacaagtggt tgctattgct agtnnnnnng gtggaaagca ggccctcgag      60
acggtgcaga ggttacttcc cgtcctctgt caagcgcacg gc                       102

<210> SEQ ID NO 19
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PCR primer
<220> FEATURE:
<221> NAME/KEY: modified_base
<222> LOCATION: (34)..(39)
<223> OTHER INFORMATION: a, c, g or t

<400> SEQUENCE: 19
ctcactccag agcaagtggt tgcgatcgct tcannnnnng gtggaagacc tgccctggaa      60

<210> SEQ ID NO 20
<211> LENGTH: 5714
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Oligonucleotide sequence encoding TALEN
      backbone

<400> SEQUENCE: 20
atgtcgcgga cccggctccc ttccccaccc gcacccagcc cagcgttttc ggccgactcg      60
ttctcagacc tgcttaggca gttcgacccc tcactgttta acacatcgtt gttcgactcc     120
cttcctccgt ttggggcgca ccatacggag gcggccaccg gggagtggga tgaggtgcag     180
tcgggattga gagctgcgga tgcaccaccc ccaaccatgc gggtggccgt caccgctgcc     240
cgaccgccga gggcgaagcc cgcaccaagg cggagggcag cgcaaccgtc cgacgcaagc     300
cccgcagcgc aagtagattt gagaactttg ggatattcac agcagcagca ggaaaagatc     360
aagcccaaag tgaggtcgac agtcgcgcag catcacgaag cgctggtggg tcatgggttt     420
```

| | |
|---|---|
| acacatgccc acatcgtagc cttgtcgcag caccctgcag cccttggcac ggtcgccgtc | 480 |
| aagtaccagg acatgattgc ggcgttgccg gaagccacac atgaggcgat cgtcggtgtg | 540 |
| gggaaacagt ggagcggagc ccgagcgctt gaggccctgt tgacggtcgc gggagagctg | 600 |
| agagggcctc cccttcagct ggacacgggc cagttgctga agatcgcgaa gcggggagga | 660 |
| gtcacggcgg tcgaggcggt gcacgcgtgg cgcaatgcgc tcacgggagc acccctcaac | 720 |
| agttcacgct gacagagacc gcggccgcat taggcacccc aggctttaca ctttatgctt | 780 |
| ccggctcgta taatgtgtgg attttgagtt aggatccgtc gagattttca ggagctaagg | 840 |
| aagctaaaat ggagaaaaaa atcactggat ataccaccgt tgatatatcc caatggcatc | 900 |
| gtaaagaaca ttttgaggca tttcagtcag ttgctcaatg tacctataac cagaccgttc | 960 |
| agctggatat tacggccttt ttaaagaccg taaagaaaaa taagcacaag ttttatccgg | 1020 |
| cctttattca cattcttgcc cgcctgatga atgctcatcc ggaattccgt atggcaatga | 1080 |
| aagacggtga gctggtgata tgggatagtt tcacccttg ttacaccgtt ttccatgagc | 1140 |
| aaactgaaac gttttcatcg ctctggagtg aataccacga cgatttccgg cagtttctac | 1200 |
| acatatattc gcaagatgtg gcgtgttacg gtgaaaacct ggcctatttc cctaaagggt | 1260 |
| ttattgagaa tatgttttc gtctcagcca atccctgggt gagtttcacc agttttgatt | 1320 |
| taaacgtggc caatatggac aacttcttcg ccccgtttt caccatgggc aaatattata | 1380 |
| cgcaaggcga caaggtgctg atgccgctgg cgattcaggt tcatcatgcc gtttgtgatg | 1440 |
| gcttccatgt cggcagaatg cttaatgaat tacaacagta ctgcgatgag tggcagggcg | 1500 |
| gggcgtaaag atctggatcc ggcttactaa aagccagata acagtatgcg tatttgcgcg | 1560 |
| ctgattttg cggtataaga atatatactg atatgtatac ccgaagtatg tcaaaaagag | 1620 |
| gtatgctatg aagcagcgta ttacagtgac agttgacagc gacagctatc agttgctcaa | 1680 |
| ggcatatatg atgtcaatat ctccggtctg gtaagcacaa ccatgcagaa tgaagcccgt | 1740 |
| cgtctgcgtg ccgaacgctg gaaagcggaa aatcaggaag gatggctga ggtcgcccgg | 1800 |
| tttattgaaa tgaacggctc ttttgctgac gagaacaggg gctggtgaaa tgcagtttaa | 1860 |
| ggtttacacc tataaaagag agagccgtta tcgtctgttt gtggatgtac agagtgatat | 1920 |
| tattgacacg cccgggcgac ggatggtgat cccctggcc agtgcacgtc tgctgtcaga | 1980 |
| taaagtctcc cgtgaacttt acccggtggt gcatatcggg gatgaaagct ggcgcatgat | 2040 |
| gaccaccgat atggccagtg tgccggtctc cgttatcggg gaagaagtgg ctgatctcag | 2100 |
| ccaccgcgaa aatgacatca aaaacgccat taacctgatg ttctggggaa tataaatgtc | 2160 |
| aggctccctt atacacagcc agtctgcagg tcgacggtct cgctcttcga aggttacttc | 2220 |
| ccgtcctctg tcaagcgcac ggcctcactc cagagcaagt ggttgcgatc gcttcaaaca | 2280 |
| acggtggaag acctgccctg gaatcaatcg tggcccagct ttcgaggccg gaccccgcgc | 2340 |
| tggccgcact cactaatgat catcttgtag cgctggcctg cctcggcgga cgacccgcct | 2400 |
| tggatgcggt gaagaagggg ctcccgcacg cgcctgcatt gattaagcgg accaacagaa | 2460 |
| ggattcccga gaggacatca catcgagtgg caggttccca actcgtgaag agtgaacttg | 2520 |
| aggagaaaaa gtcggagctg cggcacaaat tgaaatacgt accgcatgaa tacatcgaac | 2580 |
| ttatcgaaat tgctaggaac tcgactcaag acagaatcct tgagatgaag gtaatggagt | 2640 |
| tctttatgaa ggtttatgga taccgaggga agcatctcgg tggatcacga aaacccgacg | 2700 |
| gagcaatcta tacggtgggg agcccgattg attacggagt gatcgtcgac acgaaagcct | 2760 |
| acagcggtgg gtacaatctt cccatcgggc aggcagatga gatgcaacgt tatgtcgaag | 2820 |

```
aaaatcagac caggaacaaa cacatcaatc caaatgagtg gtggaaagtg tatccttcat   2880
cagtgaccga gtttaagttt ttgtttgtct ctgggcattt caaaggcaac tataaggccc   2940
agctcacacg gttgaatcac attacgaact gcaatggtgc ggttttgtcc gtagaggaac   3000
tgctcattgg tggagaaatg atcaaagcgg gaactctgac actggaagaa gtcagacgca   3060
agtttaacaa tggcgagatc aatttccgca agctaaaatg gagaaaaaaa tcactggata   3120
taccaccgtt gatatatccc aatggcatcg taaagaacat tttgaggcat ttcagtcagt   3180
tgctcaatgt acctataacc agaccgttca gctggatatt acggcctttt taaagaccgt   3240
aaagaaaaat aagcacaagt tttatccggc ctttattcac attcttgccc gcctgatgaa   3300
tgctcatccg gaattccgta tggcaatgaa agacggtgag ctggtgatat gggatagtgt   3360 tcaccccttgt tacaccgttt tccatgagca aactgaaacg ttttcatcgc tctgagtga   3420 ataccacgac gatttccggc agtttctaca catatattcg caagatgtgg cgtgttacgg   3480
tgaaaacctg gcctatttcc ctaaagggtt tattgagaat atgttttttcg tctcagccaa   3540 tccctgggtg agtttcacca gttttgattt aaacgtggcc aatatggaca acttcttcgc   3600
ccccgttttc accatgggca aatattatac gcaaggcgac aaggtgctga tgccgctggc   3660
gattcaggtt catcatgccg tttgtgatgg cttccatgtc ggcagaatgc ttaatgaatt   3720
acaacagtac tgcgatgagt ggcagggcgg ggcgtaaaga tctggatccg gcttactaaa   3780
agccagataa cagtatgcgt atttgcgcgc tgattttgc ggtataagaa tatatactga   3840
tatgtatacc cgaagtatgt caaaaagagg tatgctatga agcagcgtat tacagtgaca   3900
gttgacagcg acagctatca gttgctcaag gcatatatga tgtcaatatc tccggtctgg   3960
taagcacaac catgcagaat gaagcccgtc gtctgcgtgc cgaacgctgg aaagcggaaa   4020
atcaggaagg gatggctgag gtcgcccggt ttattgaaat gaacggctct tttgctgacg   4080
agaacagggg ctggtgaaat gcagtttaag gtttacacct ataaagagag gagccgttat   4140
cgtctgtttg tggatgtaca gagtgatatt attgacacgc ccgggcgacg gatggtgatc   4200
cccctggcca gtgcacgtct gctgtcagat aaagtctccc gtgaactta cccggtggtg   4260 catatcgggg atgaaagctg gcgcatgatg accaccgata tggccagtgt gccggtctcc   4320
gttatcgggg aagaagtggc tgatctcagc caccgcgaaa atgacatcaa aaacgccatt   4380
aacctgatgt tctggggaat ataaatgtca ggctccctta tacacagcca gtctgcaggt   4440
cgacggtctc gctcttcgaa ggttacttcc cgtcctctgt caagcgcacg gcctcactcc   4500
agagcaagtg gttgcgatcg cttcaaacaa cggtggaaga cctgccctgg aatcaatcgt   4560
ggcccagctt tcgaggccgg accccgcgct ggccgcactc actaatgatc atcttgtagc   4620
gctggcctgc ctcggcggac gacccgcctt ggatgcggtg aagaaggggc tcccgcacgc   4680
gcctgcattg attaagcgga ccaacagaag gattcccgag aggacatagc cccaagaaga   4740
agagaaaggt ggaggccagc ggttccggac gggctgacgc attggacgat tttgatctgg   4800
atatgctggg aagtgacgcc ctcgatgatt ttgacctttga catgcttggt tcggatgccc   4860
ttgatgactt tgacctcgac atgctcggca gtgacgccct tgatgatttc gacctggaca   4920
tgctgattaa ctctagaggc agtggagagg gcagaggaag tctgctaaca tgcggtgacg   4980
tcgaggagaa tcctggccca gtgagcaagg gcgaggagct gttcaccggg gtggtgccca   5040
tcctggtcga gctggacggc gacgtaaacg gccacaagtt cagcgtgtcc ggcgagggcg   5100
agggcgatgc cacctacggc aagctgaccc tgaagttcat ctgcaccacc ggcaagctgc   5160
```

-continued

| | |
|---|---|
| ccgtgccctg gcccaccctc gtgaccaccc tgacctacgg cgtgcagtgc ttcagccgct | 5220 |
| acccccgacca catgaagcag cacgacttct tcaagtccgc catgcccgaa ggctacgtcc | 5280 |
| aggagcgcac catcttcttc aaggacgacg gcaactacaa gacccgcgcc gaggtgaagt | 5340 |
| tcgagggcga caccctggtg aaccgcatcg agctgaaggg catcgacttc aaggaggacg | 5400 |
| gcaacatcct ggggcacaag ctggagtaca actacaacag ccacaacgtc tatatcatgg | 5460 |
| ccgacaagca gaagaacggc atcaaggtga acttcaagat ccgccacaac atcgaggacg | 5520 |
| gcagcgtgca gctcgccgac cactaccagc agaacacccc catcggcgac ggccccgtgc | 5580 |
| tgctgcccga caaccactac ctgagcaccc agtccgccct gagcaaagac cccaacgaga | 5640 |
| agcgcgatca catggtcctg ctggagttcg tgaccgccgc cgggatcact ctcggcatgg | 5700 |
| acgagctgta caag | 5714 |

<210> SEQ ID NO 21
<211> LENGTH: 3465
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Oligonucleotide sequence encoding TALE backbone
      sequence

<400> SEQUENCE: 21

| | |
|---|---|
| atgtcgcgga cccggctccc ttccccaccc gcacccagcc cagcgttttc ggccgactcg | 60 |
| ttctcagacc tgcttaggca gttcgacccc tcactgttta acacatcgtt gttcgactcc | 120 |
| cttcctccgt ttggggcgca ccatacggag gcggccaccg gggagtggga tgaggtgcag | 180 |
| tcgggattga gagctgcgga tgcaccaccc caaccatgc gggtggccgt caccgctgcc | 240 |
| cgaccgccga gggcgaagcc cgcaccaagg cggagggcag cgcaaccgtc cgacgcaagc | 300 |
| cccgcagcgc aagtagattt gagaactttg ggatattcac agcagcagca ggaaaagatc | 360 |
| aagcccaaag tgaggtcgac agtcgcgcag catcacgaag cgctggtggg tcatgggttt | 420 |
| acacatgccc acatcgtagc cttgtcgcag caccctgcag cccttggcac ggtcgccgtc | 480 |
| aagtaccagg acatgattgc ggcgttgccg gaagccacac atgaggcgat cgtcggtgtg | 540 |
| gggaaacagt ggagcggagc ccgagcgctt gaggccctgt tgacggtcgc gggagagctg | 600 |
| agagggcctc cccttcagct ggacacgggc cagttgctga agatcgcgaa gcggggagga | 660 |
| gtcacggcgg tcgaggcggt gcacgcgtgg cgcaatgcgc tcacgggagc accccctcaac | 720 |
| agttcacgct gacagagacc gcggccgcat taggcacccc aggctttaca ctttatgctt | 780 |
| ccggctcgta taatgtgtgg attttgagtt aggatccgtc gagattttca ggagctaagg | 840 |
| aagctaaaat ggagaaaaaa atcactggat ataccaccgt tgatatatcc caatggcatc | 900 |
| gtaaagaaca ttttgaggca tttcagtcag ttgctcaatg tacctataac cagaccgttc | 960 |
| agctggatat tacggccttt ttaaagaccg taaagaaaaa taagcacaag ttttatccgg | 1020 |
| cctttattca cattcttgcc cgcctgatga atgctcatcc ggaattccgt atggcaatga | 1080 |
| aagacggtga gctggtgata tgggatagtg ttcacccttg ttacaccgtt ttccatgagc | 1140 |
| aaactgaaac gttttcatcg ctctggagtg aataccacga cgatttccgg cagtttctac | 1200 |
| acatatattc gcaagatgtg gcgtgttacg gtgaaaacct ggcctatttc cctaaagggt | 1260 |
| ttattgagaa tatgttttc gtctcagcca atccctgggt gagtttcacc agttttgatt | 1320 |
| taaacgtggc caatatggac aacttcttcg cccccgtttt caccatgggc aaatattata | 1380 |

```
cgcaaggcga caaggtgctg atgccgctgg cgattcaggt tcatcatgcc gtttgtgatg    1440
gcttccatgt cggcagaatg cttaatgaat tacaacagta ctgcgatgag tggcagggcg    1500
gggcgtaaag atctggatcc ggcttactaa aagccagata acagtatgcg tatttgcgcg    1560 ctgattttg cggtataaga atatatactg atatgtatac ccgaagtatg tcaaaaagag    1620
gtatgctatg aagcagcgta ttacagtgac agttgacagc gacagctatc agttgctcaa    1680
ggcatatatg atgtcaatat ctccggtctg gtaagcacaa ccatgcagaa tgaagcccgt    1740
cgtctgcgtg ccgaacgctg gaaagcggaa atcaggaag ggatggctga ggtcgcccgg    1800
tttattgaaa tgaacggctc ttttgctgac gagaacaggg gctggtgaaa tgcagtttaa    1860
ggtttacacc tataaagag agagccgtta tcgtctgttt gtggatgtac agagtgatat    1920
tattgacacg cccgggcgac ggatggtgat ccccctggcc agtgcacgtc tgctgtcaga    1980
taaagtctcc cgtgaacttt acccggtggt gcatatcggg gatgaaagct ggcgcatgat    2040
gaccaccgat atggccagtg tgccggtctc cgttatcggg gaagaagtgg ctgatctcag    2100
ccaccgcgaa aatgacatca aaaacgccat taacctgatg ttctggggaa tataaatgtc    2160
aggctccctt atacacagcc agtctgcagg tcgacggtct cgctcttcga aggttacttc    2220
ccgtcctctg tcaagcgcac ggcctcactc cagagcaagt ggttgcgatc gcttcaaaca    2280
acggtggaag acctgccctg gaatcaatcg tgcccagctt tcgaggccg accccgcgc    2340 tggccgcact cactaatgat catcttgtag cgctggcctg cctcggcgga cgacccgcct    2400
tggatgcggt gaagaagggg ctcccgcacg cgcctgcatt gattaagcgg accaacagaa    2460
ggattcccga gaggacatag ccccaagaag aagagaaagg tggaggccag cggttccgga    2520
cgggctgacg cattgacga ttttgatctg gatatgctgg gaagtgacgc cctcgatgat    2580
tttgaccttg acatgcttgg ttcggatgcc cttgatgact ttgacctcga catgctcggc    2640
agtgacgccc ttgatgattt cgacctggac atgctgatta actctagagg cagtggagag    2700
ggcagaggaa gtctgctaac atgcggtgac gtcgaggaga atcctggccc agtgagcaag    2760
ggcgaggagc tgttcaccgg ggtggtgccc atcctggtcg agctggacgg cgacgtaaac    2820
ggccacaagt tcagcgtgtc cggcgagggc gagggcgatg ccacctacgg caagctgacc    2880
ctgaagttca tctgcaccac cggcaagctg cccgtgccct ggcccaccct cgtgaccacc    2940
ctgacctacg gcgtgcagtg cttcagccgc taccccgacc acatgaagca gcacgacttc    3000
ttcaagtccg ccatgcccga aggctacgtc caggagcgca ccatcttctt caaggacgac    3060
ggcaactaca agacccgcgc cgaggtgaag ttcgagggcg acacccctggt gaaccgcatc    3120 gagctgaagg gcatcgactt caaggaggac ggcaacatcc tggggcacaa gctggagtac    3180
aactacaaca gccacaacgt ctatatcatg gccgacaagc agaagaacgg catcaaggtg    3240
aacttcaaga tccgccacaa catcgaggac ggcagcgtgc agctcgccga ccactaccag    3300
cagaacaccc ccatcggcga cggccccgtg ctgctgcccg acaaccacta cctgagcacc    3360
cagtccgccc tgagcaaaga ccccaacgag aagcgcgatc acatggtcct gctggagttc    3420
gtgaccgccg ccgggatcac tctcggcatg gacgagctgt acaag            3465
```

<210> SEQ ID NO 22
<211> LENGTH: 1368
<212> TYPE: PRT
<213> ORGANISM: Streptococcus pyogenes

<400> SEQUENCE: 22

```
Met Asp Lys Lys Tyr Ser Ile Gly Leu Asp Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
                100                 105                 110

His Glu Arg His Pro Ile Phe Gly Asn Ile Val Asp Glu Val Ala Tyr
                115                 120                 125

His Glu Lys Tyr Pro Thr Ile Tyr His Leu Arg Lys Lys Leu Val Asp
            130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285

Leu Phe Leu Ala Ala Lys Asn Leu Ser Asp Ala Ile Leu Leu Ser Asp
    290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
                340                 345                 350

Asp Gln Ser Lys Asn Gly Tyr Ala Gly Tyr Ile Asp Gly Gly Ala Ser
            355                 360                 365

Gln Glu Glu Phe Tyr Lys Phe Ile Lys Pro Ile Leu Glu Lys Met Asp
        370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
```

```
                420             425             430
Leu Lys Asp Asn Arg Glu Lys Ile Glu Lys Ile Leu Thr Phe Arg Ile
            435                 440                 445

Pro Tyr Tyr Val Gly Pro Leu Ala Arg Gly Asn Ser Arg Phe Ala Trp
450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
            485                 490                 495

Asn Phe Asp Lys Asn Leu Pro Asn Glu Lys Val Leu Pro Lys His Ser
            500                 505                 510

Leu Leu Tyr Glu Tyr Phe Thr Val Tyr Asn Glu Leu Thr Lys Val Lys
            515                 520                 525

Tyr Val Thr Glu Gly Met Arg Lys Pro Ala Phe Leu Ser Gly Glu Gln
            530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
            565                 570                 575

Ser Val Glu Ile Ser Gly Val Glu Asp Arg Phe Asn Ala Ser Leu Gly
            580                 585                 590

Thr Tyr His Asp Leu Leu Lys Ile Ile Lys Asp Lys Asp Phe Leu Asp
            595                 600                 605

Asn Glu Glu Asn Glu Asp Ile Leu Glu Asp Ile Val Leu Thr Leu Thr
            610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
            645                 650                 655

Thr Gly Trp Gly Arg Leu Ser Arg Lys Leu Ile Asn Gly Ile Arg Asp
            660                 665                 670

Lys Gln Ser Gly Lys Thr Ile Leu Asp Phe Leu Lys Ser Asp Gly Phe
            675                 680                 685

Ala Asn Arg Asn Phe Met Gln Leu Ile His Asp Asp Ser Leu Thr Phe
            690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
            725                 730                 735

Ile Leu Gln Thr Val Lys Val Val Asp Glu Leu Val Lys Val Met Gly
            740                 745                 750

Arg His Lys Pro Glu Asn Ile Val Ile Glu Met Ala Arg Glu Asn Gln
            755                 760                 765

Thr Thr Gln Lys Gly Gln Lys Asn Ser Arg Glu Arg Met Lys Arg Ile
            770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
            805                 810                 815

Gln Asn Gly Arg Asp Met Tyr Val Asp Gln Glu Leu Asp Ile Asn Arg
            820                 825                 830

Leu Ser Asp Tyr Asp Val Asp His Ile Val Pro Gln Ser Phe Leu Lys
            835                 840                 845
```

```
Asp Asp Ser Ile Asp Asn Lys Val Leu Thr Arg Ser Asp Lys Asn Arg
850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
                885                 890                 895

Phe Asp Asn Leu Thr Lys Ala Glu Arg Gly Gly Leu Ser Glu Leu Asp
                900                 905                 910

Lys Ala Gly Phe Ile Lys Arg Gln Leu Val Glu Thr Arg Gln Ile Thr
            915                 920                 925

Lys His Val Ala Gln Ile Leu Asp Ser Arg Met Asn Thr Lys Tyr Asp
930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
                965                 970                 975

Glu Ile Asn Asn Tyr His His Ala His Asp Ala Tyr Leu Asn Ala Val
                980                 985                 990

Val Gly Thr Ala Leu Ile Lys Lys Tyr Pro Lys Leu Glu Ser Glu Phe
            995                 1000                1005

Val Tyr Gly Asp Tyr Lys Val Tyr Asp Val Arg Lys Met Ile Ala
    1010                1015                1020

Lys Ser Glu Gln Glu Ile Gly Lys Ala Thr Ala Lys Tyr Phe Phe
    1025                1030                1035

Tyr Ser Asn Ile Met Asn Phe Phe Lys Thr Glu Ile Thr Leu Ala
    1040                1045                1050

Asn Gly Glu Ile Arg Lys Arg Pro Leu Ile Glu Thr Asn Gly Glu
    1055                1060                1065

Thr Gly Glu Ile Val Trp Asp Lys Gly Arg Asp Phe Ala Thr Val
    1070                1075                1080

Arg Lys Val Leu Ser Met Pro Gln Val Asn Ile Val Lys Lys Thr
    1085                1090                1095

Glu Val Gln Thr Gly Gly Phe Ser Lys Glu Ser Ile Leu Pro Lys
    1100                1105                1110

Arg Asn Ser Asp Lys Leu Ile Ala Arg Lys Lys Asp Trp Asp Pro
    1115                1120                1125

Lys Lys Tyr Gly Gly Phe Asp Ser Pro Thr Val Ala Tyr Ser Val
    1130                1135                1140

Leu Val Val Ala Lys Val Glu Lys Gly Lys Ser Lys Lys Leu Lys
    1145                1150                1155

Ser Val Lys Glu Leu Leu Gly Ile Thr Ile Met Glu Arg Ser Ser
    1160                1165                1170

Phe Glu Lys Asn Pro Ile Asp Phe Leu Glu Ala Lys Gly Tyr Lys
    1175                1180                1185

Glu Val Lys Lys Asp Leu Ile Ile Lys Leu Pro Lys Tyr Ser Leu
    1190                1195                1200

Phe Glu Leu Glu Asn Gly Arg Lys Arg Met Leu Ala Ser Ala Gly
    1205                1210                1215

Glu Leu Gln Lys Gly Asn Glu Leu Ala Leu Pro Ser Lys Tyr Val
    1220                1225                1230

Asn Phe Leu Tyr Leu Ala Ser His Tyr Glu Lys Leu Lys Gly Ser
    1235                1240                1245
```

-continued

```
Pro  Glu  Asp  Asn  Glu  Gln  Lys  Gln  Leu  Phe  Val  Glu  Gln  His  Lys
   1250                1255                1260

His  Tyr  Leu  Asp  Glu  Ile  Ile  Glu  Gln  Ile  Ser  Glu  Phe  Ser  Lys
   1265                1270                1275

Arg  Val  Ile  Leu  Ala  Asp  Ala  Asn  Leu  Asp  Lys  Val  Leu  Ser  Ala
   1280                1285                1290

Tyr  Asn  Lys  His  Arg  Asp  Lys  Pro  Ile  Arg  Glu  Gln  Ala  Glu  Asn
   1295                1300                1305

Ile  Ile  His  Leu  Phe  Thr  Leu  Thr  Asn  Leu  Gly  Ala  Pro  Ala  Ala
   1310                1315                1320

Phe  Lys  Tyr  Phe  Asp  Thr  Thr  Ile  Asp  Arg  Lys  Arg  Tyr  Thr  Ser
   1325                1330                1335

Thr  Lys  Glu  Val  Leu  Asp  Ala  Thr  Leu  Ile  His  Gln  Ser  Ile  Thr
   1340                1345                1350

Gly  Leu  Tyr  Glu  Thr  Arg  Ile  Asp  Leu  Ser  Gln  Leu  Gly  Gly  Asp
   1355                1360                1365
```

<210> SEQ ID NO 23
<211> LENGTH: 82
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (41)..(41)
<223> OTHER INFORMATION: a, c, g or t

<400> SEQUENCE: 23
ttcttggctt tatatatctt gtggaaagga cgaaacaccg ngttttagag ctagaaatag     60
caagttaaaa taaggctagt cc                                              82

<210> SEQ ID NO 24
<211> LENGTH: 1692
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Oligonucleotide sequence encoding re-TALE

<400> SEQUENCE: 24
ctaacccctg aacaggtagt cgctatagct tcaaatatcg ggggcaagca agcacttgag     60
accgttcaac gactcctgcc agtgctctgc caagcccatg gattgactcc ggagcaagtc    120
gtcgcgatcg cgagcaacgg cggggggaag caggcgctgg aaactgttca gagactgctg    180
cctgtacttt gtcaggcgca tggtctcacc cccgaacagg ttgtcgcaat agcaagtaat    240
ataggcggta agcaagccct agagactgtg caacgcctgc tccccgtgct gtgtcaggct    300
cacggtctga cacctgaaca agttgtcgcg atagccagtc acgacggggg aaaacaagct    360
ctagaaacgg ttcaaaggtt gttgcccgtt ctgtgccaag cacatgggtt aacacccgaa    420
caagtagtag cgatagcgtc aaataacggg ggtaaacagg ctttggagac ggtacagcgg    480
ttattgccgg tcctctgcca ggcccacgga cttacgccag aacaggtggt tgcaattgcc    540
tccaacatcg gcgggaaaca agcgttggaa actgtgcaga gactccttcc tgttttgtgt    600
caagcccacg gcttgacgcc tgagcaggtt gtggccatcg ctagccacga cggagggaag    660
caggctcttg aaaccgtaca gcgacttctc ccagtttttgt gccaagctca cgggctaacc    720

-continued

```
cccgagcaag tagttgccat agcaagcaac ggaggaggaa acaggcatt agaaacagtt       780 cagcgcttgc tcccggtact ctgtcaggca cacggtctaa ctccggaaca ggtcgtagcc       840
attgcttccc atgatggcgg caaacaggcg ctagagacag tccagaggct cttgcctgtg       900
ttatgccagg cacatggcct cacccggag caggtcgttg ccatcgccag taatatcggc       960
ggaaagcaag ctctcgaaac agtacaacgg ctgttgccag tcctatgtca agctcatgga      1020
ctgacgcccg agcaggtagt ggcaatcgca tctcacgatg gaggtaaaca agcactcgag      1080
actgtccaaa gattgttacc cgtactatgc caagcgcatg gtttaacccc agagcaagtt     1140
gtggctattg catctaacgg cggtggcaaa caagccttgg agacagtgca acgattactg     1200
cctgtcttat gtcaggccca tggccttact cctgagcaag tcgtagctat cgccagcaac    1260
ataggtggga acaggccct ggaaaccgta acgtctcc tcccagtact ttgtcaagca       1320
cacgggttga caccggaaca agtggtggcg attgcgtcca acggcggagg caagcaggca    1380
ctggagaccg tccaacggct tcttccggtt ctttgccagg ctcatgggct cacgccagag    1440
caggtggtag caatagcgtc gaacatcggt ggtaagcaag cgcttgaaac ggtccagcgt    1500
cttctgccgg tgttgtgcca ggcgcacgga ctcacaccag aacaagtggt tgctattgct    1560
agtaacaacg gtggaaagca ggccctcgag acggtgcaga ggttacttcc cgtcctctgt    1620
caagcgcacg gcctcactcc agagcaagtg gttgcgatcg cttcaaacaa tggtggaaga    1680
cctgccctgg aa                                                         1692

<210> SEQ ID NO 25
<211> LENGTH: 237
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Template sequence
<220> FEATURE:
<221> NAME/KEY: modified_base
<222> LOCATION: (64)..(69)
<223> OTHER INFORMATION: a, c, g or t
<220> FEATURE:
<221> NAME/KEY: modified_base
<222> LOCATION: (166)..(171)
<223> OTHER INFORMATION: a, c, g or t

<400> SEQUENCE: 25
cgcaatgcgc tcacgggagc acccctcaac ctaaccctg aacaggtagt cgctatagct        60
tcannnnnng ggggcaagca agcacttgag accgttcaac gactcctgcc agtgctctgc     120
caagcccatg gattgactcc ggagcaagtc gtcgcgatcg cgagcnnnnn ngggggaag      180 caggcgctgg aaactgttca gagactgctg cctgtacttt gtcaggcgca tggtctc         237

<210> SEQ ID NO 26
<211> LENGTH: 240
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Template sequence
<220> FEATURE:
<221> NAME/KEY: modified_base
<222> LOCATION: (67)..(72)
<223> OTHER INFORMATION: a, c, g or t
<220> FEATURE:
```

```
<221> NAME/KEY: modified_base
<222> LOCATION: (169)..(174)
<223> OTHER INFORMATION: a, c, g or t

<400> SEQUENCE: 26
agactgctgc ctgtactttg tcaggcgcat ggtctcaccc ccgaacaggt tgtcgcaata      60
gcaagtnnnn nnggcggtaa gcaagccta gagactgtgc aacgcctgct ccccgtgctg     120
tgtcaggctc acggtctgac acctgaacaa gttgtcgcga tagccagtnn nnnnggggga    180
aaacaagctc tagaaacggt tcaaaggttg ttgcccgttc tgtgccaagc acatgggtta    240

<210> SEQ ID NO 27
<211> LENGTH: 232
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Template sequence
<220> FEATURE:
<221> NAME/KEY: modified_base
<222> LOCATION: (59)..(64)
<223> OTHER INFORMATION: a, c, g or t
<220> FEATURE:
<221> NAME/KEY: modified_base
<222> LOCATION: (161)..(166)
<223> OTHER INFORMATION: a, c, g or t

<400> SEQUENCE: 27
tgcgctcacg ggagcacccc tcaacctcac ccccgaacag gttgtcgcaa tagcaagtnn     60
nnnnggcggt aagcaagccc tagagactgt gcaacgcctg ctccccgtgc tgtgtcaggc    120
tcacggtctg acacctgaac aagttgtcgc gatagccagt nnnnnnggg gaaaacaagc    180 tctagaaacg gttcaaaggt tgttgcccgt tctgtgccaa gcacatgggt ta           232

<210> SEQ ID NO 28
<211> LENGTH: 246
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Template sequence
<220> FEATURE:
<221> NAME/KEY: modified_base
<222> LOCATION: (67)..(72)
<223> OTHER INFORMATION: a, c, g or t
<220> FEATURE:
<221> NAME/KEY: modified_base
<222> LOCATION: (169)..(174)
<223> OTHER INFORMATION: a, c, g or t

<400> SEQUENCE: 28
aggttgttgc ccgttctgtg ccaagcacat gggttaacac ccgaacaagt agtagcgata     60
gcgtcannnn nngggggtaa acaggctttg gagacggtac agcggttatt gccggtcctc    120
tgccaggccc acggacttac gccagaacag gtggttgcaa ttgcctccnn nnnnggcggg    180
aaacaagcgt tggaaactgt gcagagactc cttcctgttt tgtgtcaagc ccacggcttg    240
acgcct                                                               246

<210> SEQ ID NO 29
<211> LENGTH: 240
<212> TYPE: DNA
<213> ORGANISM: Artificial Sequence
```

<220> FEATURE:
<223> OTHER INFORMATION: Description of Artificial Sequence: Synthetic
      polynucleotide
<220> FEATURE:
<223> OTHER INFORMATION: Template sequence
<220> FEATURE:
<221> NAME/KEY: modified_base
<222> LOCATION: (67)..(72)
<223> OTHER INFORMATION: a, c, g or t
<220> FEATURE:
<221> NAME/KEY: modified_base
<222> LOCATION: (169)..(174)
<223> OTHER INFORMATION: a, c, g or t

<400> SEQUENCE: 29
agactccttc ctgttttgtg tcaagcccac ggcttgacgc ctgagcaggt tgtggccatc    60
gctagcnnnn nnggagggaa gcaggctctt gaaaccgtac agcgacttct cccagttttg   120
tgccaagctc acgggctaac ccccgagcaa gtagttgcca tagcaagcnn nnnnggagga   180
aaacaggcat tagaaacagt tcagcgcttg ctcccggtac tctgtcaggc acacggtcta   240

<210> SEQ ID NO 30
<211> LENGTH: 240
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Template sequence
<220> FEATURE:
<221> NAME/KEY: modified_base
<222> LOCATION: (67)..(72)
<223> OTHER INFORMATION: a, c, g or t
<220> FEATURE:
<221> NAME/KEY: modified_base
<222> LOCATION: (169)..(174)
<223> OTHER INFORMATION: a, c, g or t

<400> SEQUENCE: 30
cgcttgctcc cggtactctg tcaggcacac ggtctaactc cggaacaggt cgtagccatt    60
gcttccnnnn nnggcggcaa acaggcgcta gagaccgtcc agaggctctt gcctgtgtta   120
tgccaggcac atggcctcac cccggagcag gtcgttgcca tcgccagtnn nnnnggcgga   180
aagcaagctc tcgaaacagt acaacggctg ttgccagtcc tatgtcaagc tcatggactg   240

<210> SEQ ID NO 31
<211> LENGTH: 240
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Template sequence
<220> FEATURE:
<221> NAME/KEY: modified_base
<222> LOCATION: (67)..(72)
<223> OTHER INFORMATION: a, c, g or t
<220> FEATURE:
<221> NAME/KEY: modified_base
<222> LOCATION: (169)..(174)
<223> OTHER INFORMATION: a, c, g or t

<400> SEQUENCE: 31
cggctgttgc cagtcctatg tcaagctcat ggactgacgc ccgagcaggt agtggcaatc    60
gcatctnnnn nnggaggtaa acaagcactc gagactgtcc aaagattgtt acccgtacta   120
tgccaagcgc atggtttaac cccagagcaa gttgtggcta ttgcatctnn nnnnggtggc   180
aaacaagcct tggagaccgt gcaacgatta ctgcctgtct tatgtcaggc ccatggcctt    240

<210> SEQ ID NO 32
<211> LENGTH: 240
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Template sequence
<220> FEATURE:
<221> NAME/KEY: modified_base
<222> LOCATION: (67)..(72)
<223> OTHER INFORMATION: a, c, g or t
<220> FEATURE:
<221> NAME/KEY: modified_base
<222> LOCATION: (169)..(174)
<223> OTHER INFORMATION: a, c, g or t

<400> SEQUENCE: 32
cgattactgc ctgtcttatg tcaggcccat ggccttactc ctgagcaggt ggtcgctatc    60
gccagcnnnn nnggggcaa gcaagcactg gaaacagtcc agcgtttgct tccagtactt    120
tgtcaggcgc atggattgac accggaacaa gtggtggcta tagcctcann nnnnggagga    180
aagcaggcgc tggaaaccgt ccaacgtctt ttaccggtgc tttgccaggc gcacgggctc    240

<210> SEQ ID NO 33
<211> LENGTH: 240
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Template sequence
<220> FEATURE:
<221> NAME/KEY: modified_base
<222> LOCATION: (67)..(72)
<223> OTHER INFORMATION: a, c, g or t
<220> FEATURE:
<221> NAME/KEY: modified_base
<222> LOCATION: (169)..(174)
<223> OTHER INFORMATION: a, c, g or t

<400> SEQUENCE: 33
cgattactgc ctgtcttatg tcaggcccat ggccttactc ctgagcaagt cgtagctatc    60
gccagcnnnn nnggtgggaa acaggccctg gaaaccgtac aacgtctcct cccagtactt    120
tgtcaagcac acgggttgac accggaacaa gtggtggcga ttgcgtccnn nnnnggaggc    180
aagcaggcac tggagaccgt ccaacggctt cttccggttc tttgccaggc tcatgggctc    240

<210> SEQ ID NO 34
<211> LENGTH: 240
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Template sequence
<220> FEATURE:
<221> NAME/KEY: modified_base
<222> LOCATION: (67)..(72)
<223> OTHER INFORMATION: a, c, g or t
<220> FEATURE:
<221> NAME/KEY: modified_base
<222> LOCATION: (169)..(174)
<223> OTHER INFORMATION: a, c, g or t

<400> SEQUENCE: 34
cggcttcttc cggttctttg ccaggctcat gggctcacgc cagagcaggt ggtagcaata      60
gcgtcgnnnn nnggtggtaa gcaagcgctt gaaacggtcc agcgtcttct gccggtgttg     120
tgccaggcgc acggactcac accagaacaa gtggttgcta ttgctagtnn nnnnggtgga     180
aagcaggccc tcgagacggt gcagaggtta cttcccgtcc tctgtcaagc gcacggcctc     240

<210> SEQ ID NO 35
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Primer sequence

<400> SEQUENCE: 35
cgcaatgcgc tcacgggagc acccctcaac ctaacccctg aacaggtag                   49

<210> SEQ ID NO 36
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Primer sequence

<400> SEQUENCE: 36
gagaccatgc gcctgacaaa gtacaggcag cagtctctga acagtt                      46

<210> SEQ ID NO 37
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Primer sequence

<400> SEQUENCE: 37
tggcgcaatg cgctcacggg agcacccctc aac                                    33

<210> SEQ ID NO 38
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Primer sequence

<400> SEQUENCE: 38
agactgctgc ctgtactttg tcaggcgcat ggtctcaccc ccgaacagg                   49

<210> SEQ ID NO 39
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide <220> FEATURE:
<223> OTHER INFORMATION: Primer sequence

<400> SEQUENCE: 39
taacccatgt gcttggcaca gaacgggcaa caacctttga accgtt          46

<210> SEQ ID NO 40
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Primer sequence

<400> SEQUENCE: 40
aggttgttgc ccgttctgtg ccaagcacat gggttaacac ccgaacaa          48

<210> SEQ ID NO 41
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Primer sequence

<400> SEQUENCE: 41
aggcgtcaag ccgtgggctt gacacaaaac aggaaggagt ctctgcacag tt          52

<210> SEQ ID NO 42
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Primer sequence

<400> SEQUENCE: 42
agactccttc ctgttttgtg tcaagcccac ggcttgacgc ctgag          45

<210> SEQ ID NO 43
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Primer sequence

<400> SEQUENCE: 43
tagaccgtgt gcctgacaga gtaccgggag caagcgctga          40

<210> SEQ ID NO 44
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Primer sequence

<400> SEQUENCE: 44
cgcttgctcc cggtactctg tcaggcacac ggtctaact                                39

<210> SEQ ID NO 45
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Primer sequence

<400> SEQUENCE: 45
cagtccatga gcttgacata ggactggcaa cagccgttgt                               40

<210> SEQ ID NO 46
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Primer sequence

<400> SEQUENCE: 46
cggctgttgc cagtcctatg tcaagctcat ggactgacg                                39

<210> SEQ ID NO 47
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Primer sequence

<400> SEQUENCE: 47
aaggccatgg gcctgacata agacaggcag taatcgttgc                               40

<210> SEQ ID NO 48
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Primer sequence

<400> SEQUENCE: 48
cgattactgc ctgtcttatg tcaggcccat ggccttact                                39

<210> SEQ ID NO 49
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Primer sequence

<400> SEQUENCE: 49
gagcccgtgc gcctggcaaa gcaccggtaa aagacgttgg acg                           43

```
<210> SEQ ID NO 50
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Primer sequence

<400> SEQUENCE: 50
cgattactgc ctgtcttatg tcaggcccat ggccttactc ctgagcaagt              50

<210> SEQ ID NO 51
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Primer sequence

<400> SEQUENCE: 51
gagcccatga gcctggcaaa gaaccggaag aagccgttgg                         40

<210> SEQ ID NO 52
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Primer sequence

<400> SEQUENCE: 52
cggcttcttc cggttctttg ccaggctcat gggctcacgc cagagcaggt g            51

<210> SEQ ID NO 53
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Primer sequence

<400> SEQUENCE: 53
gaggccgtgc gcttgacaga ggacgggaag taacctctgc                         40

<210> SEQ ID NO 54
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Targeting sequence

<400> SEQUENCE: 54
tccccacttt cttgtgaa                                                 18

<210> SEQ ID NO 55
<211> LENGTH: 18
<212> TYPE: DNA
<213> ORGANISM: Artificial Sequence
```

```
<220> FEATURE:
<223> OTHER INFORMATION: Description of Artificial Sequence: Synthetic
      oligonucleotide
<220> FEATURE:
<223> OTHER INFORMATION: Targeting sequence

<400> SEQUENCE: 55
taaccactca ggacaggg                                                        18

<210> SEQ ID NO 56
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Targeting sequence

<400> SEQUENCE: 56
cactttcttg tgaatccctt                                                      19

<210> SEQ ID NO 57
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Targeting sequence

<400> SEQUENCE: 57
tcacacagca agtcagca                                                        18

<210> SEQ ID NO 58
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Targeting sequence

<400> SEQUENCE: 58
tagcggagca ggctcgga                                                        18

<210> SEQ ID NO 59
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Targeting sequence

<400> SEQUENCE: 59
tgggctagcg gagcaggct                                                       19

<210> SEQ ID NO 60
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
```

<223> OTHER INFORMATION: Targeting sequence

<400> SEQUENCE: 60
tacccagacg agaaagct                                                      18

<210> SEQ ID NO 61
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Targeting sequence

<400> SEQUENCE: 61
tcagactgcc aagcttga                                                      18

<210> SEQ ID NO 62
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Targeting sequence

<400> SEQUENCE: 62
acccagacga gaaagctga                                                     19

<210> SEQ ID NO 63
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Targeting sequence

<400> SEQUENCE: 63
tcttgtggct cgggagta                                                      18

<210> SEQ ID NO 64
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Targeting sequence

<400> SEQUENCE: 64
tattgtcagc agagctga                                                      18

<210> SEQ ID NO 65
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Targeting sequence

<400> SEQUENCE: 65
agagggcatc ttgtggctc                                              19

<210> SEQ ID NO 66
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Targeting sequence

<400> SEQUENCE: 66
ttgagatttt cagatgtc                                               18

<210> SEQ ID NO 67
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Targeting sequence

<400> SEQUENCE: 67
tatacagtca tatcaagc                                               18

<210> SEQ ID NO 68
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Targeting sequence

<400> SEQUENCE: 68
atcaagctct cttggcggt                                              19

<210> SEQ ID NO 69
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Targeting sequence

<400> SEQUENCE: 69
ttcagataga ttatatct                                               18

<210> SEQ ID NO 70
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Targeting sequence

<400> SEQUENCE: 70
tgccagatac ataggtgg                                               18

<210> SEQ ID NO 71

```
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Targeting sequence

<400> SEQUENCE: 71
gcttcagata gattatatc                                              19

<210> SEQ ID NO 72
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Targeting sequence

<400> SEQUENCE: 72
ttatactgtc tatatgat                                               18

<210> SEQ ID NO 73
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Targeting sequence

<400> SEQUENCE: 73
tcagctcttc tggccaga                                               18

<210> SEQ ID NO 74
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Targeting sequence

<400> SEQUENCE: 74
acggatgtct cagctcttc                                              19

<210> SEQ ID NO 75
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Targeting sequence

<400> SEQUENCE: 75
tggccagaag agctgaga                                               18

<210> SEQ ID NO 76
<211> LENGTH: 18
<212> TYPE: DNA
<213> ORGANISM: Artificial Sequence
<220> FEATURE:
```

```
<223> OTHER INFORMATION: Description of Artificial Sequence: Synthetic
      oligonucleotide
<220> FEATURE:
<223> OTHER INFORMATION: Targeting sequence

<400> SEQUENCE: 76
ttaccgggga gagtttct                                                        18

<210> SEQ ID NO 77
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Targeting sequence

<400> SEQUENCE: 77
ccggggagag tttcttgta                                                       19

<210> SEQ ID NO 78
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Targeting sequence

<400> SEQUENCE: 78
tttgcagaga gatgagtc                                                        18

<210> SEQ ID NO 79
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Targeting sequence

<400> SEQUENCE: 79
ttagcagaag ataagatt                                                        18

<210> SEQ ID NO 80
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Targeting sequence

<400> SEQUENCE: 80
gaaatcttat cttctgcta                                                       19

<210> SEQ ID NO 81
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Targeting sequence
```

-continued

```
<400> SEQUENCE: 81
tataagacta aactaccc                                                 18

<210> SEQ ID NO 82
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Targeting sequence

<400> SEQUENCE: 82
tcgtctgcca ccacagat                                                 18

<210> SEQ ID NO 83
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Targeting sequence

<400> SEQUENCE: 83
aatgcatgac attcatctg                                                19

<210> SEQ ID NO 84
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Targeting sequence

<400> SEQUENCE: 84
taaaacagtt tgcattca                                                 18

<210> SEQ ID NO 85
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Targeting sequence

<400> SEQUENCE: 85
tataaagtcc tagaatgt                                                 18

<210> SEQ ID NO 86
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Targeting sequence

<400> SEQUENCE: 86
aacagtttgc attcatgga                                                19
```

<210> SEQ ID NO 87
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Targeting sequence

<400> SEQUENCE: 87
tggccatctc tgacctgt                                                 18

<210> SEQ ID NO 88
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Targeting sequence

<400> SEQUENCE: 88
tagtgagccc agaagggg                                                 18

<210> SEQ ID NO 89
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Targeting sequence

<400> SEQUENCE: 89
ccagaagggg acagtaaga                                                19

<210> SEQ ID NO 90
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Targeting sequence

<400> SEQUENCE: 90
taggtacctg gctgtcgt                                                 18

<210> SEQ ID NO 91
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Targeting sequence

<400> SEQUENCE: 91
tgaccgtcct ggctttta                                                 18

<210> SEQ ID NO 92
<211> LENGTH: 19

```
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Targeting sequence

<400> SEQUENCE: 92
ctgacaatcg ataggtacc                                                19

<210> SEQ ID NO 93
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Targeting sequence

<400> SEQUENCE: 93
tgtcatggtc atctgcta                                                 18

<210> SEQ ID NO 94
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Targeting sequence

<400> SEQUENCE: 94
tcgacaccga agcagagt                                                 18

<210> SEQ ID NO 95
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Targeting sequence

<400> SEQUENCE: 95
acaccgaagc agagttttt                                                19

<210> SEQ ID NO 96
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Targeting sequence

<400> SEQUENCE: 96
tgcccccgcg aggccaca                                                 18

<210> SEQ ID NO 97
<211> LENGTH: 18
<212> TYPE: DNA
<213> ORGANISM: Artificial Sequence
<220> FEATURE:
<223> OTHER INFORMATION: Description of Artificial Sequence: Synthetic
```

```
            oligonucleotide
<220> FEATURE:
<223> OTHER INFORMATION: Targeting sequence

<400> SEQUENCE: 97
tctggaagtt gaacaccc                                                 18

<210> SEQ ID NO 98
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Targeting sequence

<400> SEQUENCE: 98
ggaagttgaa cacccttgc                                                19

<210> SEQ ID NO 99
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Target sequence

<400> SEQUENCE: 99
ctactgtcat tcagggcaat acccagacga gaaagctgag ggtataacag gtttcaagct    60
tggcagtctg actacagagg ccactggctt                                    90

<210> SEQ ID NO 100
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Target sequence

<400> SEQUENCE: 100
ctactgtcat tcagcccaat accctaacga gaaagctgag ggtataacag gtttcaagct    60
tggcagtctg actacagagg ccactggctt                                    90

<210> SEQ ID NO 101
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Target sequence

<400> SEQUENCE: 101
ctactgtcat tcagcccaat acccagacga gaaaagtgag ggtataacag gtttcaagct    60
tggcagtctg actacagagg ccactggctt                                    90

<210> SEQ ID NO 102
<211> LENGTH: 90
<212> TYPE: DNA
<213> ORGANISM: Artificial Sequence
```

<220> FEATURE:
<223> OTHER INFORMATION: Description of Artificial Sequence: Synthetic
      oligonucleotide
<220> FEATURE:
<223> OTHER INFORMATION: Target sequence

<400> SEQUENCE: 102
ctactgtcat tcagcccaat acccagacga gaaagctgag ggtataacag gtttcaagct    60
tggcagtctg actacagagg ccactggctt                                    90

<210> SEQ ID NO 103
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Target sequence

<400> SEQUENCE: 103
ctactgtcat tcagcccaat acccagacga gaaagctgag ggtataacag gtttgtagct    60
tggcagtctg actacagagg ccactggctt                                    90

<210> SEQ ID NO 104
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Target sequence

<400> SEQUENCE: 104
ctactgtcat tcagcccaat acccagacga gaaagctgag ggtataacag gtttcaagct    60
tggctctctg actacagagg ccactggctt                                    90

<210> SEQ ID NO 105
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Target sequence

<400> SEQUENCE: 105
ctactgtcat tcagcccaat acccagacga gaaagctgag ggtataacag gtttcaagct    60
tggcagtctg actagtgagg ccactggctt                                    90

<210> SEQ ID NO 106
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Target sequence

<400> SEQUENCE: 106
cactttatat ttccctgctt aaacagtccc ccgagggtgg gtgcggaaaa ggctctacac    60
ttgttatcat tccctctcca ccacaggcat                                    90

<210> SEQ ID NO 107
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Target sequence

<400> SEQUENCE: 107
tttgtatttg ggttttttta aaacctccac tctacagtta agaattctaa ggcacagagc      60
ttcaataatt tggtcagagc caagtagcag                                      90

<210> SEQ ID NO 108
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Target sequence

<400> SEQUENCE: 108
ggaggttaaa cccagcagca tgactgcagt tcttaatcaa tgccccttga attgcacata      60
tgggatgaac tagaacattt tctcgatgat                                      90

<210> SEQ ID NO 109
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Target sequence

<400> SEQUENCE: 109
ctcgatgatt cgctgtcctt gttatgatta tgttactgag ctctactgta gcacagacat      60
atgtccctat atgggcggg ggtggggtg                                        90

<210> SEQ ID NO 110
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Taregt sequence

<400> SEQUENCE: 110
ggtgtcttga tcgctgggct atttctatac tgttctggct tttcggaagc agtcatttct      60
ttctattctc caagcaccag caattagctt                                      90

<210> SEQ ID NO 111
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Target sequence

<400> SEQUENCE: 111
gcttctagtt tgctgaaact aatctgctat agacagagac tccgacgaac caattttatt      60
aggatttgat caaataaact ctctctgaca                                        90

<210> SEQ ID NO 112
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Target sequence

<400> SEQUENCE: 112
gaaagagtaa ctaagagttt gatgtttact gagtgcatag tatgcactag atgctggccg      60
tggatgcctc atagaatcct cccaacaact                                        90

<210> SEQ ID NO 113
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Target sequence

<400> SEQUENCE: 113
gctagatgct ggccgtggat gcctcataga atcctcccaa caaccgatga aatgactact      60
gtcattcagc ccaataccca gacgagaaag                                        90

<210> SEQ ID NO 114
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Target sequence

<400> SEQUENCE: 114
acaggtttca agcttggcag tctgactaca gaggccactg gctttacccc tgggttagtc      60
tgcctctgta ggattggggg cacgtaattt                                        90

<210> SEQ ID NO 115
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Target sequence

<400> SEQUENCE: 115
ttagtctgcc tctgtaggat tgggggcacg taattttgct gtttaaggtc tcatttgcct      60
tcttagagat cacaagccaa agcttttat                                         90

<210> SEQ ID NO 116
<211> LENGTH: 90
<212> TYPE: DNA

<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Target sequence

<400> SEQUENCE: 116

```
ggaagcccag agggcatctt gtggctcggg agtagctctc tgctaccttc tcagctctgc    60
tgacaatact tgagattttc agatgtcacc                                     90
```

<210> SEQ ID NO 117
<211> LENGTH: 90
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Target sequence

<400> SEQUENCE: 117

```
tcagctctgc tgacaatact tgagattttc agatgtcacc aaccagcaag agagcttgat    60
atgactgtat atagtatagt cataaagaac                                     90
```

<210> SEQ ID NO 118
<211> LENGTH: 90
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Target sequence

<400> SEQUENCE: 118

```
cataaagaac ctgaacttga ccatatactt atgtcatgtg gaaatcttct catagcttca    60
gatagattat atctggagtg aagaatcctg                                     90
```

<210> SEQ ID NO 119
<211> LENGTH: 90
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Target sequence

<400> SEQUENCE: 119

```
gtggaaaatt tctcatagct tcagatagat tatatctgga gtgagcaatc ctgccaccta    60
tgtatctggc atagtgtgag tcctcataaa                                     90
```

<210> SEQ ID NO 120
<211> LENGTH: 90
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Target sequence

<400> SEQUENCE: 120

```
ggtttgaagg gcaacaaaat agtgaacaga gtgaaaatcc ccacctagat cctgggtcca    60
```
gaaaaagatg ggaaacctgt ttagctcacc                                         90

<210> SEQ ID NO 121
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Target sequence

<400> SEQUENCE: 121
ggccactagg gacaaaattg gtgacagaaa                                         30

<210> SEQ ID NO 122
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Target sequence

<400> SEQUENCE: 122
cccacagtgg ggccactagg gacaaaattg gtgacagaaa agccccatcc                   50

<210> SEQ ID NO 123
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Target sequence

<400> SEQUENCE: 123
tcccctccac cccacagtgg ggccactagg gacaaaattg gtgacagaaa agccccatcc        60
ttaggcctcc                                                               70

<210> SEQ ID NO 124
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Target sequence

<400> SEQUENCE: 124
cttttatctg tccctccac cccacagtgg ggccactagg gacaaaattg gtgacagaaa         60
agccccatcc ttaggcctcc tccttcctag                                         90

<210> SEQ ID NO 125
<211> LENGTH: 110
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Target sequence

<400> SEQUENCE: 125
gttctgggta cttttatctg tcccctccac cccacagtgg ggccactagg gacaaaattg    60
gtgacagaaa agccccatcc ttaggcctcc tccttcctag tctcctgata              110

<210> SEQ ID NO 126
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Target sequence

<400> SEQUENCE: 126
tttctgtcac caatggtgtc cctagtggcc                                    30

<210> SEQ ID NO 127
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Target sequence

<400> SEQUENCE: 127
ggatggggct tttctgtcac caatggtgtc cctagtggcc ccactgtggg              50

<210> SEQ ID NO 128
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Target sequence

<400> SEQUENCE: 128
ggaggcctaa ggatggggct tttctgtcac caatggtgtc cctagtggcc ccactgtggg   60
gtggagggga                                                          70

<210> SEQ ID NO 129
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Target sequence

<400> SEQUENCE: 129
ctaggaagga ggaggcctaa ggatggggct tttctgtcac caatggtgtc cctagtggcc   60
ccactgtggg gtggagggga cagataaaag                                    90

<210> SEQ ID NO 130
<211> LENGTH: 110
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Target sequence

```
<400> SEQUENCE: 130
tatcaggaga ctaggaagga ggaggcctaa ggatggggct tttctgtcac caatggtgtc    60
cctagtggcc ccactgtggg gtggagggga cagataaaag tacccagaac              110

<210> SEQ ID NO 131
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Target sequence

<400> SEQUENCE: 131
ttctagtaac cactcaggac aggggggttc agcccaaaaa ttcacaagaa agtggggacc    60
catgggaaat                                                          70

<210> SEQ ID NO 132
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Target sequence

<400> SEQUENCE: 132
cagcaagtca gcagcacagc gtgtgtgact ccgagggtgc tccgctagcc cacattgccc    60
tctgggggtg                                                          70

<210> SEQ ID NO 133
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Target sequence

<400> SEQUENCE: 133
gtcagactgc caagcttgaa acctgtctta ccctctactt tctcgtctgg gtattgggct    60
gaatgacagt                                                          70

<210> SEQ ID NO 134
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Target sequence

<400> SEQUENCE: 134
cagagctgag aagacagcag agagctactc ccgaagcaca agatgccctc tgggcttccg    60
tgaccttggc                                                          70

<210> SEQ ID NO 135
<211> LENGTH: 70
<212> TYPE: DNA
<213> ORGANISM: Artificial Sequence
```

```
<220> FEATURE:
<223> OTHER INFORMATION: Description of Artificial Sequence: Synthetic
      oligonucleotide
<220> FEATURE:
<223> OTHER INFORMATION: Target sequence

<400> SEQUENCE: 135
ctgacaatac ttgagatttt cagatgtcac caacgaccaa gagagcttga tatgactgta    60
tatagtatag                                                           70

<210> SEQ ID NO 136
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Target sequence

<400> SEQUENCE: 136
cagatacata ggtggcagga ttcttcactc cagacttaat ctatctgaag ctatgagaaa    60
ttttccacat                                                           70

<210> SEQ ID NO 137
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Target sequence

<400> SEQUENCE: 137
tatatgattg atttgcacag ctcatctggc cagataagct gagacatccg ttcccctaca    60
agaaactctc                                                           70

<210> SEQ ID NO 138
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Target sequence

<400> SEQUENCE: 138
atctggccag aagagctgag acatccgttc cccttgaaga aactctcccc ggtaagtaac    60
ctctcagctg                                                           70

<210> SEQ ID NO 139
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Target sequence

<400> SEQUENCE: 139
aggcatctca ctggagaggg tttagttctc cttaagagaa gataagattt caagagggaa    60
gctaagactc                                                           70
```

<210> SEQ ID NO 140
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Target sequence

<400> SEQUENCE: 140
ataatataat aaaaaatgtt tcgtctgcca ccactaatga atgtcatgca ttctgggtag    60
tttagtctta                                                          70

<210> SEQ ID NO 141
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Target sequence

<400> SEQUENCE: 141
tttataaagt cctagaatgt atttagttgc cctcgttgaa tgcaaactgt tttatacatc    60
aataggtttt                                                          70

<210> SEQ ID NO 142
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Target sequence

<400> SEQUENCE: 142
gctcaacctg gccatctctg acctgttttt ccttcccact gtccccttct gggctcacta    60
tgctgccgcc                                                          70

<210> SEQ ID NO 143
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Target sequence

<400> SEQUENCE: 143
ttttaaagca aacacagcat ggacgacagc caggctccta tcgattgtca ggaggatgat    60
gaagaagatt                                                          70

<210> SEQ ID NO 144
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Target sequence

<400> SEQUENCE: 144
gcttgtcatg gtcatctgct actcgggaat cctaattact ctgcttcggt gtcgaaatga    60
gaagaagagg                                                           70

<210> SEQ ID NO 145
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Target sequence

<400> SEQUENCE: 145
atactgcccc cgcgaggcca cattggcaaa ccagcttggg tgttcaactt ccagacttgg    60
ccatggagaa                                                           70

<210> SEQ ID NO 146
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Target sequence

<400> SEQUENCE: 146
ctgaagaatt tcccatgggt ccccactttc ttgtgaatcc ttggagtgaa ccccctgtc     60 ctgagtggtt actagaacac acctctggac                                    90

<210> SEQ ID NO 147
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Target sequence

<400> SEQUENCE: 147
tggaagtatc ttgccgaggt cacacagcaa gtcagcagca cagccagtgt gactccgagc    60
ctgctccgct agcccacatt gccctctggg                                    90

<210> SEQ ID NO 148
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Target sequence

<400> SEQUENCE: 148
ctactgtcat tcagcccaat acccagacga gaaagctgag ggtataacag gtttcaagct    60
tggcagtctg actacagagg ccactggctt                                    90

<210> SEQ ID NO 149
<211> LENGTH: 90
<212> TYPE: DNA

<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Target sequence

<400> SEQUENCE: 149
ggaagcccag agggcatctt gtggctcggg agtagctctc tgctaccttc tcagctctgc    60
tgacaatact tgagattttc agatgtcacc                                     90

<210> SEQ ID NO 150
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Target sequence

<400> SEQUENCE: 150
tcagctctgc tgacaatact tgagattttc agatgtcacc aacgcccaag agagcttgat    60
atgactgtat atagtatagt cataaagaac                                     90

<210> SEQ ID NO 151
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Target sequence

<400> SEQUENCE: 151
gtggaaaatt tctcatagct tcagatagat tatatctgga gtgagcaatc ctgccaccta    60
tgtatctggc atagtgtgag tcctcataaa                                     90

<210> SEQ ID NO 152
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Target sequence

<400> SEQUENCE: 152
gaaacagcat ttcctacttt tatactgtct atatgattga tttggtcagc tcatctggcc    60
agaagagctg agacatccgt tccctacaa                                      90

<210> SEQ ID NO 153
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Target sequence

<400> SEQUENCE: 153
ttgatttgca cagctcatct ggccagaaga gctgagacat ccgtatccct acaagaaact    60

```
ctccccggta agtaacctct cagctgcttg                                      90
```

<210> SEQ ID NO 154
<211> LENGTH: 90
<212> TYPE: DNA
<213> ORGANISM: Artificial Sequence
<220> FEATURE:
<223> OTHER INFORMATION: Description of Artificial Sequence: Synthetic
     oligonucleotide
<220> FEATURE:
<223> OTHER INFORMATION: Target sequence

<400> SEQUENCE: 154

```
ggagagggtt tagttctcct tagcagaaga taagatttca agatgagagc taagactcat    60
ctctctgcaa atctttcttt tgagaggtaa                                      90
```

<210> SEQ ID NO 155
<211> LENGTH: 90
<212> TYPE: DNA
<213> ORGANISM: Artificial Sequence
<220> FEATURE:
<223> OTHER INFORMATION: Description of Artificial Sequence: Synthetic
     oligonucleotide
<220> FEATURE:
<223> OTHER INFORMATION: Target sequence

<400> SEQUENCE: 155

```
taatataata aaaaatgttt cgtctgccac cacagatgaa tgtcgagcat tctgggtagt    60
ttagtcttat aaccagctgt cttgcctagt                                      90
```

<210> SEQ ID NO 156
<211> LENGTH: 90
<212> TYPE: DNA
<213> ORGANISM: Artificial Sequence
<220> FEATURE:
<223> OTHER INFORMATION: Description of Artificial Sequence: Synthetic
     oligonucleotide
<220> FEATURE:
<223> OTHER INFORMATION: Target sequence

<400> SEQUENCE: 156

```
ttaaaaacct attgatgtat aaaacagttt gcattcatgg agggtgacta aatacattct    60
aggactttat aaaagatcac ttttattta                                      90
```

<210> SEQ ID NO 157
<211> LENGTH: 90
<212> TYPE: DNA
<213> ORGANISM: Artificial Sequence
<220> FEATURE:
<223> OTHER INFORMATION: Description of Artificial Sequence: Synthetic
     oligonucleotide
<220> FEATURE:
<223> OTHER INFORMATION: Target sequence

<400> SEQUENCE: 157

```
gacatctacc tgctcaacct ggccatctct gacctgtttt tcctatttac tgtccccttc    60
tgggctcact atgctgccgc ccagtgggac                                      90
```

<210> SEQ ID NO 158
<211> LENGTH: 90
<212> TYPE: DNA
<213> ORGANISM: Artificial Sequence
<220> FEATURE:
<223> OTHER INFORMATION: Description of Artificial Sequence: Synthetic
     oligonucleotide
<220> FEATURE:

-continued

<223> OTHER INFORMATION: Target sequence

<400> SEQUENCE: 158
tcatcctcct gacaatcgat aggtacctgg ctgtcgtcca tgctacgttt gctttaaaag    60
ccaggacggt cacctttggg gtggtgacaa                                     90

<210> SEQ ID NO 159
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Target sequence

<400> SEQUENCE: 159
ggctggtcct gccgctgctt gtcatggtca tctgctactc gggagaccta aaaactctgc    60
ttcggtgtcg aaatgagaag aagaggcaca                                     90

<210> SEQ ID NO 160
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Target sequence

<400> SEQUENCE: 160
ggcaagcctt gggtcatact gcccccgcga ggccacattg gcaagtcagc aagggtgttc    60
aacttccaga cttggccatg gagaagacat                                     90

<210> SEQ ID NO 161
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PCR primer

<400> SEQUENCE: 161
acactctttc cctacacgac gctcttccga tctcgtgatt ttgcagtgtg cgttactcc     59

<210> SEQ ID NO 162
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PCR primer

<400> SEQUENCE: 162
acactctttc cctacacgac gctcttccga tctacatcgt ttgcagtgtg cgttactcc     59

<210> SEQ ID NO 163
<211> LENGTH: 59
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: PCR primer

<400> SEQUENCE: 163
acactctttc cctacacgac gctcttccga tctgcctaat ttgcagtgtg cgttactcc      59

<210> SEQ ID NO 164
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PCR primer

<400> SEQUENCE: 164
acactctttc cctacacgac gctcttccga tcttggtcat ttgcagtgtg cgttactcc      59

<210> SEQ ID NO 165
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PCR primer

<400> SEQUENCE: 165
ctcggcattc ctgctgaacc gctcttccga tctccaagca actaagtcac agca           54

<210> SEQ ID NO 166
<211> LENGTH: 58
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PCR primer

<400> SEQUENCE: 166
acactctttc cctacacgac gctcttccga tctcgtgata tgaggaaatg gaagcttg       58

<210> SEQ ID NO 167
<211> LENGTH: 58
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PCR primer

<400> SEQUENCE: 167
acactctttc cctacacgac gctcttccga tctacatcga tgaggaaatg gaagcttg       58

<210> SEQ ID NO 168
<211> LENGTH: 58
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PCR primer

```
<400> SEQUENCE: 168
acactctttc cctacacgac gctcttccga tctgcctaaa tgaggaaatg gaagcttg          58

<210> SEQ ID NO 169
<211> LENGTH: 58
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PCR primer

<400> SEQUENCE: 169
acactctttc cctacacgac gctcttccga tcttggtcaa tgaggaaatg gaagcttg          58

<210> SEQ ID NO 170
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PCR primer

<400> SEQUENCE: 170
ctcggcattc tgctgaacc gctcttccga tctcattagg gtattggagg a                  51

<210> SEQ ID NO 171
<211> LENGTH: 58
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PCR primer

<400> SEQUENCE: 171
acactctttc cctacacgac gctcttccga tctcgtgata atcctcccaa caactcat         58

<210> SEQ ID NO 172
<211> LENGTH: 58
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PCR primer

<400> SEQUENCE: 172
acactctttc cctacacgac gctcttccga tctacatcga atcctcccaa caactcat         58

<210> SEQ ID NO 173
<211> LENGTH: 58
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PCR primer

<400> SEQUENCE: 173
acactctttc cctacacgac gctcttccga tctgcctaaa atcctcccaa caactcat         58
```

<210> SEQ ID NO 174
<211> LENGTH: 58
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: PCR primer

<400> SEQUENCE: 174
acactctttc cctacacgac gctcttccga tcttggtcaa atcctcccaa caactcat        58

<210> SEQ ID NO 175
<211> LENGTH: 52
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: PCR primer

<400> SEQUENCE: 175
ctcggcattc ctgctgaacc gctcttccga tctcccaatc ctacagaggc ag              52

<210> SEQ ID NO 176
<211> LENGTH: 58
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: PCR primer

<400> SEQUENCE: 176
acactctttc cctacacgac gctcttccga tctcgtgata agccaaagct ttttattc        58

<210> SEQ ID NO 177
<211> LENGTH: 58
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: PCR primer

<400> SEQUENCE: 177
acactctttc cctacacgac gctcttccga tctacatcga agccaaagct ttttattc        58

<210> SEQ ID NO 178
<211> LENGTH: 58
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: PCR primer

<400> SEQUENCE: 178
acactctttc cctacacgac gctcttccga tctgcctaaa agccaaagct ttttattc        58

<210> SEQ ID NO 179
<211> LENGTH: 58
<212> TYPE: DNA

```
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PCR primer

<400> SEQUENCE: 179
acactctttc cctacacgac gctcttccga tcttggtcaa agccaaagct ttttattc      58

<210> SEQ ID NO 180
<211> LENGTH: 53
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PCR primer

<400> SEQUENCE: 180
acactctttc cctacacgac gctcttccga tctaagccaa agctttttat tct           53

<210> SEQ ID NO 181
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PCR primer

<400> SEQUENCE: 181
acactctttc cctacacgac gctcttccga tctcgtgata tcttgtggct cgggagtag     59

<210> SEQ ID NO 182
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PCR primer

<400> SEQUENCE: 182
acactctttc cctacacgac gctcttccga tctacatcga tcttgtggct cgggagtag     59

<210> SEQ ID NO 183
<211> LENGTH: 53
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PCR primer

<400> SEQUENCE: 183
ctcggcattc ctgctgaacc gctcttccga tcttggcagg attcttcact cca           53

<210> SEQ ID NO 184
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide
```

-continued

```
<220> FEATURE:
<223> OTHER INFORMATION: PCR primer

<400> SEQUENCE: 184
acactctttc cctacacgac gctcttccga tctcgtgatc tattttgttg cccttcaaa      59

<210> SEQ ID NO 185
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PCR primer

<400> SEQUENCE: 185
acactctttc cctacacgac gctcttccga tctacatcgc tattttgttg cccttcaaa      59

<210> SEQ ID NO 186
<211> LENGTH: 55
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PCR primer

<400> SEQUENCE: 186
ctcggcattc ctgctgaacc gctcttccga tctaacctga acttgaccat atact      55

<210> SEQ ID NO 187
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PCR primer

<400> SEQUENCE: 187
acactctttc cctacacgac gctcttccga tctcgtgatc agctgagagg ttacttacc      59

<210> SEQ ID NO 188
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PCR primer

<400> SEQUENCE: 188
acactctttc cctacacgac gctcttccga tctacatcgc agctgagagg ttacttacc      59

<210> SEQ ID NO 189
<211> LENGTH: 53
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PCR primer

<400> SEQUENCE: 189
```

```
ctcggcattc ctgctgaacc gctcttccga tctaatgatt taactccacc ctc          53
```

<210> SEQ ID NO 190
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PCR primer

<400> SEQUENCE: 190

```
acactctttc cctacacgac gctcttccga tctcgtgata ctccaccctc cttcaaaaga   60
```

<210> SEQ ID NO 191
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PCR primer

<400> SEQUENCE: 191

```
acactctttc cctacacgac gctcttccga tctacatcga ctccaccctc cttcaaaaga   60
```

<210> SEQ ID NO 192
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PCR primer

<400> SEQUENCE: 192

```
ctcggcattc ctgctgaacc gctcttccga tcttggtgtt tgccaaatgt ct           52
```

<210> SEQ ID NO 193
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PCR primer

<400> SEQUENCE: 193

```
acactctttc cctacacgac gctcttccga tctcgtgatg ggcacatatt cagaaggca    59
```

<210> SEQ ID NO 194
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PCR primer

<400> SEQUENCE: 194

```
acactctttc cctacacgac gctcttccga tctacatcgg ggcacatatt cagaaggca    59
```

```
<210> SEQ ID NO 195
<211> LENGTH: 56
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PCR primer

<400> SEQUENCE: 195
ctcggcattc ctgctgaacc gctcttccga tctagtgaaa gactttaaag ggagca         56

<210> SEQ ID NO 196
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PCR primer

<400> SEQUENCE: 196
acactctttc cctacacgac gctcttccga tctcgtgatc acaattaaga gttgtcata         59

<210> SEQ ID NO 197
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PCR primer

<400> SEQUENCE: 197
acactctttc cctacacgac gctcttccga tctacatcgc acaattaaga gttgtcata         59

<210> SEQ ID NO 198
<211> LENGTH: 53
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PCR primer

<400> SEQUENCE: 198
ctcggcattc ctgctgaacc gctcttccga tctctcagct agagcagctg aac               53

<210> SEQ ID NO 199
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PCR primer

<400> SEQUENCE: 199
ctcggcattc ctgctgaacc gctcttccga tctgacactt gataatccat c                 51

<210> SEQ ID NO 200
<211> LENGTH: 60
<212> TYPE: DNA
<213> ORGANISM: Artificial Sequence
```

```
<220> FEATURE:
<223> OTHER INFORMATION: Description of Artificial Sequence: Synthetic
      oligonucleotide
<220> FEATURE:
<223> OTHER INFORMATION: PCR primer

<400> SEQUENCE: 200
acactctttc cctacacgac gctcttccga tctacatcgt caatgtagac atctatgtag    60

<210> SEQ ID NO 201
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PCR primer

<400> SEQUENCE: 201
acactctttc cctacacgac gctcttccga tctcgtgatt caatgtagac atctatgtag    60

<210> SEQ ID NO 202
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PCR primer

<400> SEQUENCE: 202
acactctttc cctacacgac gctcttccga tctcgtgata ctgcaaaagg ctgaagagc     59

<210> SEQ ID NO 203
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PCR primer

<400> SEQUENCE: 203
acactctttc cctacacgac gctcttccga tctacatcga ctgcaaaagg ctgaagagc     59

<210> SEQ ID NO 204
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PCR primer

<400> SEQUENCE: 204
acactctttc cctacacgac gctcttccga tctgcctaaa ctgcaaaagg ctgaagagc     59

<210> SEQ ID NO 205
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
```

<223> OTHER INFORMATION: PCR primer

<400> SEQUENCE: 205
acactctttc cctacacgac gctcttccga tcttggtcaa ctgcaaaagg ctgaagagc    59

<210> SEQ ID NO 206
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PCR primer

<400> SEQUENCE: 206
ctcggcattc tgctgaacc gctcttccga tctgcctata aaatagagcc ctgtcaa    57

<210> SEQ ID NO 207
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PCR primer

<400> SEQUENCE: 207
acactctttc cctacacgac gctcttccga tctcgtgatc tctattttat aggcttcttc    60

<210> SEQ ID NO 208
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PCR primer

<400> SEQUENCE: 208
acactctttc cctacacgac gctcttccga tctacatcgc tctattttat aggcttcttc    60

<210> SEQ ID NO 209
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PCR primer

<400> SEQUENCE: 209
ctcggcattc tgctgaacc gctcttccga tctagccacc acccaagtga tc    52

<210> SEQ ID NO 210
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PCR primer

<400> SEQUENCE: 210
acactctttc cctacacgac gctcttccga tctacatcgt tccagacatt aaagatagtc    60

<210> SEQ ID NO 211
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PCR primer

<400> SEQUENCE: 211
acactctttc cctacacgac gctcttccga tctcgtgatt tccagacatt aaagatagtc    60

<210> SEQ ID NO 212
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PCR primer

<400> SEQUENCE: 212
ctcggcattc ctgctgaacc gctcttccga tctaatcatg atggtgaaga taag           54

<210> SEQ ID NO 213
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PCR primer

<400> SEQUENCE: 213
acactctttc cctacacgac gctcttccga tctcgtgatc cggcagagac aaacattaaa    60

<210> SEQ ID NO 214
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PCR primer

<400> SEQUENCE: 214
acactctttc cctacacgac gctcttccga tctccggcag agacaaacat taaa            54

<210> SEQ ID NO 215
<211> LENGTH: 53
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PCR primer

<400> SEQUENCE: 215
ctcggcattc ctgctgaacc gctcttccga tctagctagg aagccatggc aag             53

<210> SEQ ID NO 216

```
<211> LENGTH: 47
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PCR primer

<400> SEQUENCE: 216
aatgatacgg cgaccaccga gatctacact ctttccctac acgacgc           47

<210> SEQ ID NO 217
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PCR primer

<400> SEQUENCE: 217
caagcagaag acggcatacg agatcggtct cggcattcct gctgaaccgc         50

<210> SEQ ID NO 218
<211> LENGTH: 58
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PCR primer

<400> SEQUENCE: 218
acactctttc cctacacgac gctcttccga tctagtgcat agtatgtgct agatgctg    58

<210> SEQ ID NO 219
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PCR primer

<400> SEQUENCE: 219
gtgactggag ttcagacgtg tgctcttccg atcttgatct ctaagaaggc aaatgagac   59

<210> SEQ ID NO 220
<211> LENGTH: 64
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PCR primer
<220> FEATURE:
<221> NAME/KEY: modified_base
<222> LOCATION: (25)..(30)
<223> OTHER INFORMATION: a, c, g or t

<400> SEQUENCE: 220
caagcagaag acggcatacg agatnnnnnn gtgactggag ttcagacgtg tgctcttccg   60
atct                                                               64
```

<210> SEQ ID NO 221
<211> LENGTH: 58
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PCR primer

<400> SEQUENCE: 221
aatgatacgg cgaccaccga gatctacact ctttccctac acgacgctct tccgatct         58

<210> SEQ ID NO 222
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Deduced TALE template amino acid sequence
<220> FEATURE:
<221> NAME/KEY: MOD_RES
<222> LOCATION: (12)..(13)
<223> OTHER INFORMATION: Any naturally occurring amino acid

<400> SEQUENCE: 222

Leu Thr Pro Glu Gln Val Val Ala Ile Ala Ser Xaa Xaa Gly Gly Lys
1               5                   10                  15

Gln Ala Leu Glu Thr Val Gln Arg Leu Leu Pro Val Leu Cys Gln Ala
            20                  25                  30

His Gly

<210> SEQ ID NO 223
<211> LENGTH: 246
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: TALE dimer nucleotide sequence

<400> SEQUENCE: 223
cgattactgc ctgtcttatg tcaggcccat ggccttactc ctgagcaagt cgtagctatc         60
gccagcaaca taggtgggaa acaggccctg gaaaccgtac aacgtctcct cccagtactt        120
tgtcaagcac acgggttgac accggaacaa gtggtggcga ttgcgtccca cgatggaggc        180
aagcaggcac tggagaccgt ccaacggctt cttccggttc tttgccaggc tcatgggctc        240
acgcca                                                                  246

<210> SEQ ID NO 224
<211> LENGTH: 82
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Deduced TALE dimer amino acid sequence

<400> SEQUENCE: 224

Arg Leu Leu Pro Val Leu Cys Gln Ala His Gly Leu Thr Pro Glu Gln
1               5                   10                  15

```
Val Val Ala Ile Ala Ser Asn Ile Gly Gly Lys Gln Ala Leu Glu Thr
            20                  25                  30

Val Gln Arg Leu Leu Pro Val Leu Cys Gln Ala His Gly Leu Thr Pro
        35                  40                  45

Glu Gln Val Val Ala Ile Ala Ser His Asp Gly Gly Lys Gln Ala Leu
 50                  55                  60

Glu Thr Val Gln Arg Leu Leu Pro Val Leu Cys Gln Ala His Gly Leu
65                  70                  75                  80

Thr Pro

<210> SEQ ID NO 225
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: target nucleotide sequence

<400> SEQUENCE: 225
gctcaaccat ggggactggg tg                                                22

<210> SEQ ID NO 226
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: target nucleotide sequence

<400> SEQUENCE: 226
gctcaaccat gggactgggt                                                   20

<210> SEQ ID NO 227
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: target nucleotide sequence

<400> SEQUENCE: 227
gctcaaccat actgggt                                                      17
```

GENOME ENGINEERING

RELATED APPLICATION DATA

This application is a National Stage application under 35 U.S.C. 371 of co-pending PCT application number PCT/US2014/048140 designating the United States and filed Jul. 25, 2014; which claims priority to U.S. Provisional Patent Application No. 61/858,866 filed on Jul. 26, 2013 and is hereby incorporated herein by reference in its entirety for all purposes.

STATEMENT OF GOVERNMENT INTERESTS

This invention was made with government support under P50 HG003170 from the National Human Genome Research Center for Excellence in Genomics Science. The government has certain rights in the invention.

BACKGROUND

Genome editing via sequence-specific nucleases is known. See references 1, 2, and 3 hereby incorporated by reference in their entireties. A nuclease-mediated double-stranded DNA (dsDNA) break in the genome can be repaired by two main mechanisms: Non-Homologous End Joining (NHEJ), which frequently results in the introduction of non-specific insertions and deletions (indels), or homology directed repair (HDR), which incorporates a homologous strand as a repair template. See reference 4 hereby incorporated by reference in its entirety. When a sequence-specific nuclease is delivered along with a homologous donor DNA construct containing the desired mutations, gene targeting efficiencies are increased by 1000-fold compared to just the donor construct alone. See reference 5 hereby incorporated by reference in its entirety. Use of single stranded oligodeoxyribonucleotides ("ssODNs") as DNA donors has been reported. See references 21 and 22 hereby incorporated by reference in their entireties.

Despite large advances in gene editing tools, many challenges and questions remain regarding the use of custom-engineered nucleases in human induced pluripotent stem cell ("hiPSC") engineering. First, despite their design simplicity, Transcription Activator-Like Effectors Nucleases (TALENs) target particular DNA sequences with tandem copies of Repeat Variable Diresidue (RVD) domains. See reference 6 hereby incorporated by reference in its entirtety. While the modular nature of RVDs simplifies TALEN design, their repetitive sequences complicate methods for synthesizing their DNA constructs (see references 2, 9, and 15-19 hereby incorporated by reference in their entireties) and also impair their use with lentiviral gene delivery vehicles. See reference 13 hereby incorporated by reference in its entirety.

In current practice, NHEJ and HDR are frequently evaluated using separate assays. Mismatch-sensitive endonuclease assays (see reference 14 hereby incorporated by reference in its entirety) are often used for assessing NHEJ, but the quantitative accuracy of this method is variable and the sensitivity is limited to NHEJ frequencies greater than ~3%. See reference 15 hereby incorporated by reference in its entirety. HDR is frequently assessed by cloning and sequencing, a completely different and often cumbersome procedure. Sensitivity is still an issue because, while high editing frequencies on the order of 50% are frequently reported for some cell types, such as U2OS and K562 (see references 12 and 14 hereby incorporated by reference in their entireties), frequencies are generally lower in hiPSCs. See reference 10 hereby incorporated by reference in its entirety. Recently, high editing frequencies have been reported in hiPSC and hESC using TALENs (see reference 9 hereby incorporated by reference in its entirety), and even higher frequencies with the CRISPR Cas9-gRNA system (see references 16-19 hereby incorporated by reference in their entireties. However, editing rates at different sites appear to vary widely (see reference 17 hereby incorporated by reference in its entirety), and editing is sometimes not detectable at all at some sites (see reference 20 hereby incorporated by reference in its entirety).

Bacterial and archaeal CRISPR-Cas systems rely on short guide RNAs in complex with Cas proteins to direct degradation of complementary sequences present within invading foreign nucleic acid. See Deltcheva, E. et al. CRISPR RNA maturation by trans-encoded small RNA and host factor RNase III. Nature 471, 602-607 (2011); Gasiunas, G., Barrangou, R., Horvath, P. & Siksnys, V. Cas9-crRNA ribonucleoprotein complex mediates specific DNA cleavage for adaptive immunity in bacteria. Proceedings of the National Academy of Sciences of the United States of America 109, E2579-2586 (2012); Jinek, M. et al. A programmable dual-RNA-guided DNA endonuclease in adaptive bacterial immunity Science 337, 816-821 (2012); Sapranauskas, R. et al. The *Streptococcus thermophilus* CRISPR/Cas system provides immunity in *Escherichia coli*. Nucleic acids research 39, 9275-9282 (2011); and Bhaya, D., Davison, M. & Barrangou, R. CRISPR-Cas systems in bacteria and archaea: versatile small RNAs for adaptive defense and regulation. Annual review of genetics 45, 273-297 (2011). A recent in vitro reconstitution of the *S. pyogenes* type II CRISPR system demonstrated that crRNA ("CRISPR RNA") fused to a normally trans-encoded tracrRNA ("trans-activating CRISPR RNA") is sufficient to direct Cas9 protein to sequence-specifically cleave target DNA sequences matching the crRNA. Expressing a gRNA homologous to a target site results in Cas9 recruitment and degradation of the target DNA. See H. Deveau et al., Phage response to CRISPR-encoded resistance in *Streptococcus thermophilus*. Journal of Bacteriology 190, 1390 (February, 2008).

SUMMARY

Aspects of the present disclosure are directed to the use of modified Transcription Activator-Like Effector Nucleases (TALENs) for genetically modifying a cell, such as a somatic cell or a stem cell. TALENs are known to include repeat sequences. Aspects of the present disclosure are directed to a method of altering target DNA in a cell including introducing into a cell a TALEN lacking repeat sequences 100 bp or longer wherein the TALEN cleaves the target DNA and the cell undergoes nonhomologous end joining to produce altered DNA in the cell. According to certain aspects, repeat sequences of desired length have been removed from a TALEN. According to certain aspects, the TALEN is devoid of repeat sequences of certain desired length. According to certain aspects, a TALEN is provided with repeat sequences of desired length removed. According to certain aspects, a TALEN is modified to remove repeat sequences of desired length. According to certain aspects, a TALEN is engineered to remove repeat sequences of desired length.

Aspects of the present disclosure include methods of altering target DNA in a cell including combining within a cell a TALEN lacking repeat sequences 100 bp or longer and a donor nucleic acid sequence wherein the TALEN cleaves the target DNA and the donor nucleic acid sequence is inserted into the DNA in the cell. Aspects of the present disclosure are directed to a virus including a nucleic acid sequence encoding a TALEN lacking repeat sequences 100 bp or longer. Aspects of the present disclosure are directed to a cell including a nucleic acid sequence encoding a TALEN lacking repeat sequences 100 bp or longer. According to certain aspects described herein, the TALEN lacks repeat sequences 100 bp or longer, 90 bp or longer, 80 bp or longer, 70 bp or longer, 60 bp or longer, 50 bp or longer, 40 bp or longer, 30 bp or longer, 20 bp or longer, 19 bp or longer, 18 bp or longer, 17 bp or longer, 16 bp or longer, 15 bp or longer, 14 bp or longer, 13 bp or longer, 12 bp or longer, 11 bp or longer, or 10 bp or longer.

Aspects of the present disclosure are directed to making a TALE including combining an endonuclease, a DNA polymerase, a DNA ligase, an exonuclease, a plurality of nucleic acid dimer blocks encoding repeat variable diresidue domains and a TALE-N/TF backbone vector including an endonuclease cutting site, activating the endonuclease to cut the TALE-N/TF backbone vector at the endonuclease cutting site to produce a first end and a second end, activating the exonuclease to create a 3' and a 5' overhang on the TALE-N/TF backbone vector and the plurality of nucleic acid dimer blocks and to anneal the TALE-N/TF backbone vector and the plurality of nucleic acid dimer blocks in a desired order, activating the DNA polymerase and the DNA ligase to connect the TALE-N/TF backbone vector and the plurality of nucleic acid dimer blocks. One of skill in the art will readily based on the present disclosure be able to identify suitable endonucleases, DNA polymerases, DNA ligases, exonucleases, nucleic acid dimer blocks encoding repeat variable diresidue domains and TALE-N/TF backbone vectors.

Aspects of the present disclosure are directed to a method of altering target DNA in a stem cell expressing an enzyme that forms a co-localization complex with RNA complementary to the target DNA and that cleaves the target DNA in a site specific manner including (a) introducing into the stem cell a first foreign nucleic acid encoding an RNA complementary to the target DNA and which guides the enzyme to the target DNA, wherein the RNA and the enzyme are members of a co-localization complex for the target DNA, introducing into the stem cell a second foreign nucleic acid encoding a donor nucleic acid sequence, wherein the RNA and the donor nucleic acid sequences are expressed, wherein the RNA and the enzyme co-localize to the target DNA, the enzyme cleaves the target DNA and the donor nucleic acid is inserted into the target DNA to produce altered DNA in the stem cell.

Aspects of the present disclosure are directed to a stem cell including a first foreign nucleic acid encoding for an enzyme that forms a co-localization complex with RNA complementary to target DNA and that cleaves the target DNA in a site specific manner.

Aspects of the present disclosure are directed to a cell including a first foreign nucleic acid encoding for an enzyme that forms a co-localization complex with RNA complementary to target DNA and that cleaves the target DNA in a site specific manner and including an inducible promoter for promoting expression of the enzyme. In this manner, expression can be regulated, for example, it can be started and it can be stopped.

Aspects of the present disclosure are directed to a cell including a first foreign nucleic acid encoding for an enzyme that forms a co-localization complex with RNA complementary to target DNA and that cleaves the target DNA in a site specific manner, wherein the first foreign nucleic acid is removable from genomic DNA of the cell using a removal enzyme, such as a transposase. Aspects of the present disclosure are directed to a method of altering target DNA in a cell expressing an enzyme that forms a co-localization complex with RNA complementary to the target DNA and that cleaves the target DNA in a site specific manner including (a) introducing into the cell a first foreign nucleic acid encoding a donor nucleic acid sequence, introducing into the cell from media surrounding the cell an RNA complementary to the target DNA and which guides the enzyme to the target DNA, wherein the RNA and the enzyme are members of a co-localization complex for the target DNA, wherein the donor nucleic acid sequence is expressed, wherein the RNA and the enzyme co-localize to the target DNA, the enzyme cleaves the target DNA and the donor nucleic acid is inserted into the target DNA to produce altered DNA in the cell.

Aspects of the present disclosure are directed to the use of an RNA guided DNA binding protein for genetically modifying a stem cell. In one aspect, the stem cell has been genetically modified to include a nucleic acid encoding for the RNA guided DNA binding protein and the stem cell expresses the RNA guided DNA binding protein. According to a certain aspect, donor nucleic acids for introducing specific mutations are optimized for genome editing using either the modified TALENs or the RNA guided DNA binding protein.

Aspects of the present disclosure are directed to the modification of DNA, such as multiplex modification of DNA, in a stem cell using one or more guide RNAs (ribonucleic acids) to direct an enzyme having nuclease activity expressed by the stem cell, such as a DNA binding protein having nuclease activity, to a target location on the DNA (deoxyribonucleic acid) wherein the enzyme cuts the DNA and an exogenous donor nucleic acid is inserted into the DNA, such as by homologous recombination. Aspects of the present disclosure include cycling or repeating steps of DNA modification on a stem cell to create a stem cell having multiple modifications of DNA within the cell. Modifications may include insertion of exogenous donor nucleic acids.

Multiple exogenous nucleic acid insertions can be accomplished by a single step of introducing into a stem cell, which expresses the enzyme, nucleic acids encoding a plurality of RNAs and a plurality of exogenous donor nucleic acids, such as by co-transformation, wherein the RNAs are expressed and wherein each RNA in the plurality guides the enzyme to a particular site of the DNA, the enzyme cuts the DNA and one of the plurality of exogenous nucleic acids is inserted into the DNA at the cut site. According to this aspect, many alterations or modification of the DNA in the cell are created in a single cycle.

Multiple exogenous nucleic acid insertions can be accomplished in a cell by repeated steps or cycles of introducing into a stem cell, which expresses the enzyme, one or more nucleic acids encoding one or more RNAs or a plurality of RNAs and one or more exogenous nucleic acids or a plurality of exogenous nucleic acids wherein the RNA is expressed and guides the enzyme to a particular site of the DNA, the enzyme cuts the DNA and the exogenous nucleic acid is inserted into the DNA at the cut site, so as to result in a cell having multiple alterations or insertions of exogenous DNA into the DNA within the stem cell. According to one aspect, the stem cell expressing the enzyme has been genetically altered to express the enzyme such as by introducing into the cell a nucleic acid encoding the enzyme and which can be expressed by the stem cell. In this manner, aspects of the present disclosure include cycling the steps of introducing RNA into a stem cell which expresses the enzyme, introducing exogenous donor nucleic acid into the stem cell, expressing the RNA, forming a co-localization complex of the RNA, the enzyme and the DNA, enzymatic cutting of the DNA by the enzyme, and insertion of the donor nucleic acid into the DNA. Cycling or repeating of the above steps results in multiplexed genetic modification of a stem cell at multiple loci, i.e., a stem cell having multiple genetic modifications.

According to certain aspects, DNA binding proteins or enzymes within the scope of the present disclosure include a protein that forms a complex with the guide RNA and with the guide RNA guiding the complex to a double stranded DNA sequence wherein the complex binds to the DNA sequence. According to one aspect, the enzyme can be an RNA guided DNA binding protein, such as an RNA guided DNA binding protein of a Type II CRISPR System that binds to the DNA and is guided by RNA. According to one aspect, the RNA guided DNA binding protein is a Cas9 protein.

This aspect of the present disclosure may be referred to as co-localization of the RNA and DNA binding protein to or with the double stranded DNA. In this manner, a DNA binding protein-guide RNA complex may be used to cut multiple sites of the double stranded DNA so as to create a stem cell with multiple genetic modifications, such as multiple insertions of exogenous donor DNA.

According to certain aspects, a method of making multiple alterations to target DNA in a stem cell expressing an enzyme that forms a co-localization complex with RNA complementary to the target DNA and that cleaves the target DNA in a site specific manner is provided including (a) introducing into the stem cell a first foreign nucleic acid encoding one or more RNAs complementary to the target DNA and which guide the enzyme to the target DNA, wherein the one or more RNAs and the enzyme are members of a co-localization complex for the target DNA, introducing into the stem cell a second foreign nucleic acid encoding one or more donor nucleic acid sequences, wherein the one or more RNAs and the one or more donor nucleic acid sequences are expressed, wherein the one or more RNAs and the enzyme co-localize to the target DNA, the enzyme cleaves the target DNA and the donor nucleic acid is inserted into the target DNA to produce altered DNA in the stem cell, and repeating step (a) multiple times to produce multiple alterations to the DNA in the stem cell.

According to one aspect, the RNA is between about 10 to about 500 nucleotides. According to one aspect, the RNA is between about 20 to about 100 nucleotides.

According to one aspect, the one or more RNAs is a guide RNA. According to one aspect, the one or more RNAs is a tracrRNA-crRNA fusion.

According to one aspect, the DNA is genomic DNA, mitochondrial DNA, viral DNA, or exogenous DNA.

According to one aspect, a cell may be genetically modified to reversibly include a nucleic acid encoding a DNA binding enzyme using a vector which can be easily removed using an enzyme. Useful vectors methods are known to those of skill in the art and include lentivirus, adeno associated virus, nuclease and integrase mediated targeted insertion methods and transposon mediated insertion methods. According to one aspect, the nucleic acid encoding a DNA binding enzyme that has been added, such as by using a cassette or vector can be removed in its entirety along with the cassette and vector and without leaving a portion of such nucleic acid, cassette or vector in the genomic DNA, for example. Such removal is referred to in the art as "scarless" removal, as the genome is the same as it was before addition of the nucleic acid, cassette or vector. One exemplary embodiment for insertion and scarless removal is a Piggy-Bac vector commercially available from System Biosciences.

Further features and advantages of certain embodiments of the present invention will become more fully apparent in the following description of embodiments and drawings thereof, and from the claims.

BRIEF DESCRIPTION OF THE DRAWINGS

The foregoing and other features and advantages of the present embodiments will be more fully understood from the following detailed description of illustrative embodiments taken in conjunction with the accompanying drawings in which.

(a) Schematic representation of experimental design for testing genome targeting efficiency. A genomically integrated GFP coding sequence is disrupted by the insertion of a stop codon and a 68 bp genomic fragment derived from the AAVS1 locus (bottom). Restoration of the GFP sequence by nuclease-mediated homologous recombination with tGFP donor (top) results in GFP+ cells that can be quantitated by FACS. Re-TALENs and TALENs target identical sequences within AAVS1 fragments.

(b) Bar graph depicting GFP+ cell percentage introduced by tGFP donor alone, TALENs with tGFP donor, and re-TALENs with tGFP donor at the target locus, as measured by FACS. (N=3, error bar=SD) Representative FACS plots are shown below.

(c) Schematic overview depicting the targeting strategy for the native AAVS1 locus. The donor plasmid, containing splicing acceptor (SA)-2A (self-cleaving peptides), puromycin resistant gene (PURO) and GFP were described (see reference 10 hereby incorporated by reference in its entirety. The locations of PCR primers used to detect successful editing events are depicted as blue arrows.

(d) Successfully targeted clones of PGP1 hiPSCs were selected with puromycin (0.5 ug/mL) for 2 weeks. Microscopy images of three representative GFP+ clones are shown. Cells were also stained for the pluripotency markers TRA-1-60. Scale bar: 200 μm.

(e) PCR assays performed on these the monoclonal GFP+ hiPSC clones demonstrated successful insertions of the donor cassettes at the AAVS1 site (lane 1, 2, 3), whereas plain hiPSCs show no evidence of successful insertion (lane C).

(f) Depicts (SEQ ID NO:1).

Figure 2A:
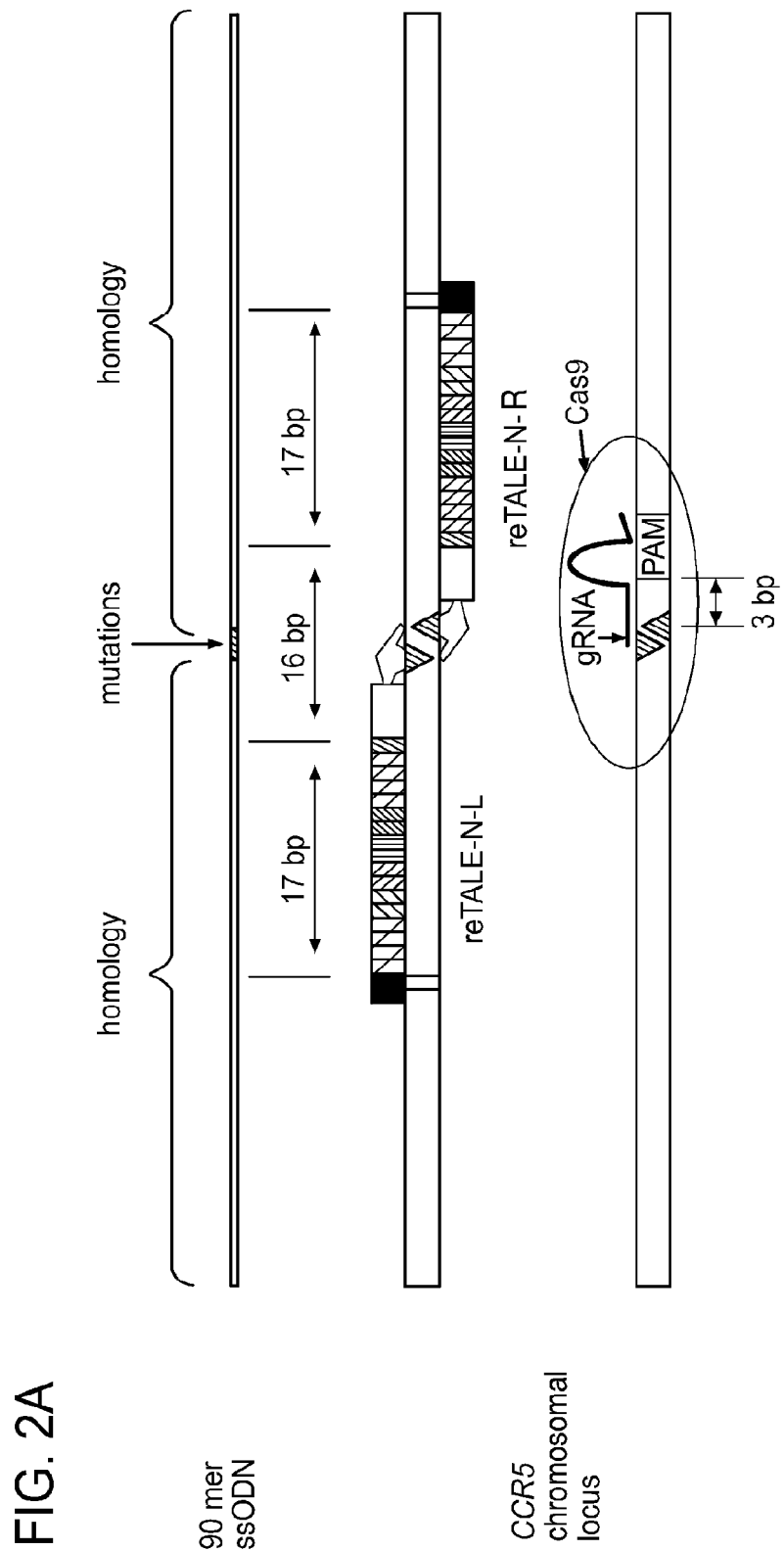

FIG. 2 relates to a comparison of reTALENs and Cas9-gRNAs genome targeting efficiency on CCR5 in iPSCs.

(a) Schematic representation of genome engineering experimental design. At the re-TALEN pair or Cas9-gRNA targeting site, a 90mer ssODN carrying a 2 bp mismatch against the genomic DNA was delivered along with the reTALEN or Cas9-gRNA constructs into PGP1 hiPSCs. The cutting sites of the nucleases are depicted as red arrows in the figure.

(b) Deep sequencing analysis of HDR and NHEJ efficiencies for re-TALEN pairs (CCR5 #3) and ssODN, or the Cas9-gRNA and ssODN. Alterations in the genome of hiPSCs were analyzed from high-throughput sequence data by GEAS. Top: HDR was quantified from the fraction of reads that contained a 2 bp point mutation built into the center of the ssODN (blue), and NHEJ activity was quantified from the fraction of deletions (grey)/ Insertions (red) at each specific position in the genome. For the reTALEN and ssODN graphs, green dashed lines are plotted to mark the outer boundary of the re-TALEN pair's binding sites, which are at positions −26 bp and +26 bp relative to the center of the two re-TALEN binding sites. For Cas9-gRNA and ssODN graphs, the green dashed lines mark the outer boundary of the gRNA targeting site, which are at positions −20 and −1 bp relative to the PAM sequence. Bottom: Deletion/Insertion size distribution in hiPSCs analyzed from the entire NHEJ population with treatments indicated above.

(c) The genome editing efficiency of re-TALENs and Cas9-gRNAs targeting CCR5 in PGP1 hiPSCs.

Top: schematic representation of the targeted genome editing sites in CCR5. The 15 targeting sites are illustrated by blue arrows below. For each site, cells were co-transfected with a pair of re-TALENs and their corresponding ssODN donor carrying 2 bp mismatches against the genomic DNA. Genome editing efficiencies were assayed 6 days after transfection. Similarly, 15 Cas9-gRNAs were transfected with their corresponding ssODNs individually into PGP1-hiPSCs to target the same 15 sites and analyzed the efficiency 6 days after transfection. Bottom: the genome editing efficiency of re-TALENs and Cas9-gRNAs targeting CCR5 in PGP1 hiPSCs. Panel 1 and 2 indicate NHEJ and HDR efficiencies mediated by reTALENs. Panel 3 and 4 indicate NHEJ and HDR efficiencies mediated by Cas9-gRNAs. NHEJ rates were calculated by the frequency of genomic alleles carrying deletions or insertions at the targeting region; HDR rates were calculated by the frequency of genomic alleles carrying 2 bp mismatches. Panel 5, the DNaseI HS profile of a hiPSC cell line from ENCODE database (Duke DNase HS, iPS NIHi7 DS). Of note, the scales of different panels are different.

(f) Sanger sequencing of the PCR amplicon from the three targeted hiPSC colonies confirmed that the expected DNA bases at the genome-insertion boundary are present. M: DNA ladder. C: control with plain hiPSCs genomic DNA.

FIG. 3 is directed to a study of functional parameters governing ssODN-mediated HDR with re-TALENs it Cas9-gRNAs in PGP1 hiPSCs.

(a) PGP1 hiPSCs were co-transfected with re-TALENs pair (#3) and ssODNs of different lengths (50, 70, 90, 110, 130, 150, 170 nts). All ssODNs possessed an identical 2 bp mismatch against the genomic DNA in the middle of their sequence. A 90mer ssODN achieved optimal HDR in the targeted genome. The assessment of HDR, NHEJ-incurred deletion and insertion efficiency is as described herein.

(b) 90mer ssODNs corresponding to re-TALEN pair #3 each containing a 2 bp mismatch (A) in the center and an additional 2 bp mismatch (B) at different positions offset from A (where offsets varied from −30 bp→30 bp) were used to test the effects of deviations from homology along the ssODN. Genome editing efficiency of each ssODN was assessed in PGP1 hiPSCs. The bottom bar graph shows the incorporation frequency of A only, B only, and A+B in the targeted genome. HDR rates decrease as the distance of homology deviations from the center increase.

(c) ssODNs targeted to sites with varying distances (−620 bp~480 bp) away from the target site of re-TALEN pair #3 were tested to assess the maximum distance within which ssODNs can be placed to introduce mutations. All ssODNs carried a 2 bp mismatch in the middle of their sequences. Minimal HDR efficiency (<=0.06%) was observed when the ssODN mismatch was positioned 40 bp away from the middle of re-TALEN pair's binding site.

(d) PGP1 hiPSCs were co-transfected with Cas9-gRNA (AAVS1) and ssODNs of different orientation (Oc: complement to gRNA; On: non-complement to gRNA) and different lengths (30, 50, 70, 90, 110 nt). All ssODNs possessed an identical 2 bp mismatch against the genomic DNA in the middle of their sequence. A 70mer Oc achieved optimal HDR in the targeted genome.

FIG. 4 is directed to using re-TALENs and ssODNs to obtain monoclonal genome edited hiPSC without selection.

(a) Timeline of the experiment.

Figure 2B:
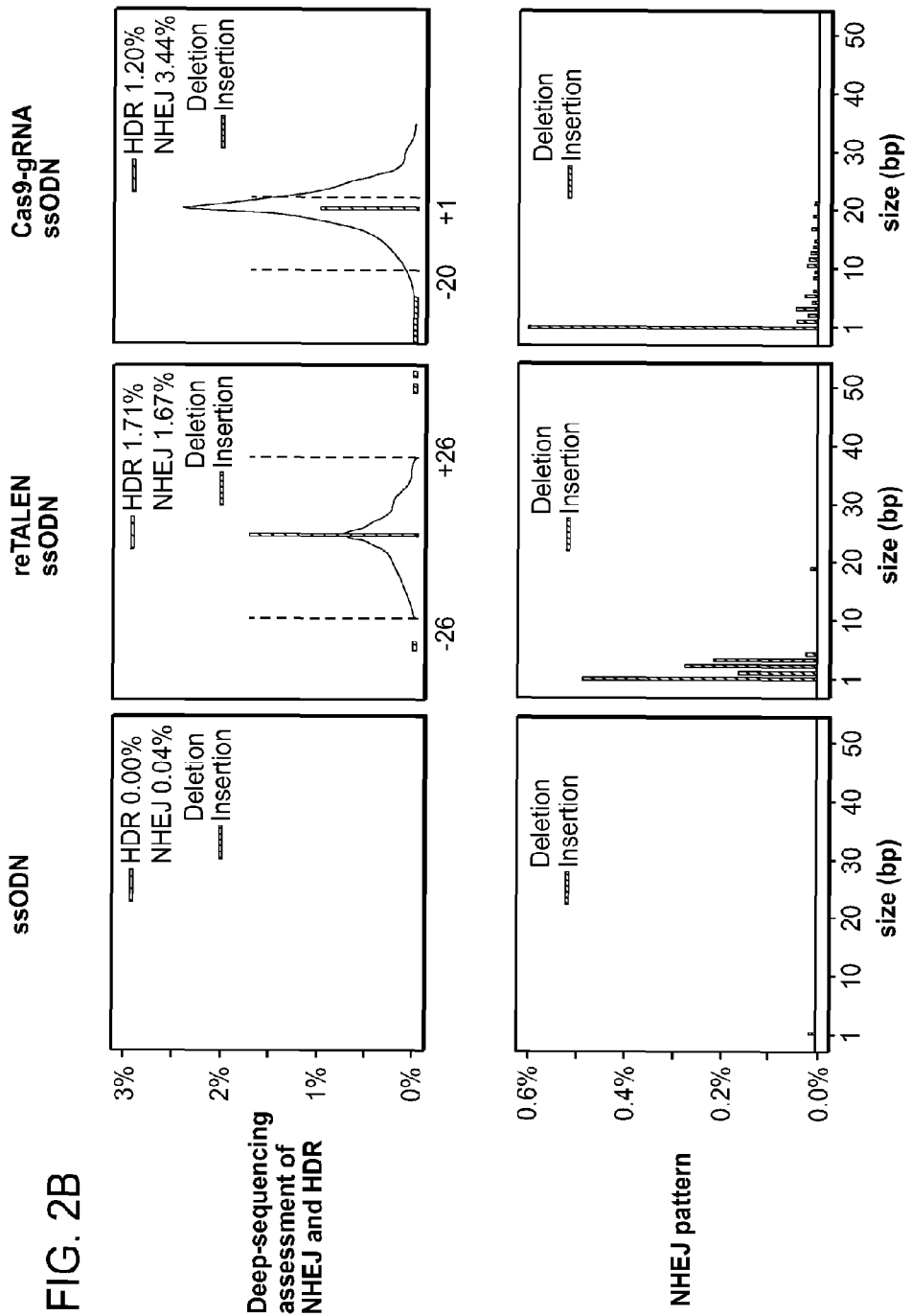

(b) Genome engineering efficiency of re-TALENs pair and ssODN (#3) assessed by the NGS platform described in FIG. 2b.

(c) Sanger sequencing results of monoclonal hiPSC colonies after genome editing. The 2 bp heterogeneous genotype (CT/CT→TA/CT) was successfully introduced into the genome of PGP1-iPS-3-11, PGP1-iPS-3-13 colonies.

(d) Immunofluorescence staining of targeted PGP1-iPS-3-11. Cells were stained for the pluripotency markers Tra-1-60 and SSEA4.

(e) Hematoxylin and eosin staining of teratoma sections generated from monoclonal PGP1-iPS-3-11 cells.

Figure 5B:
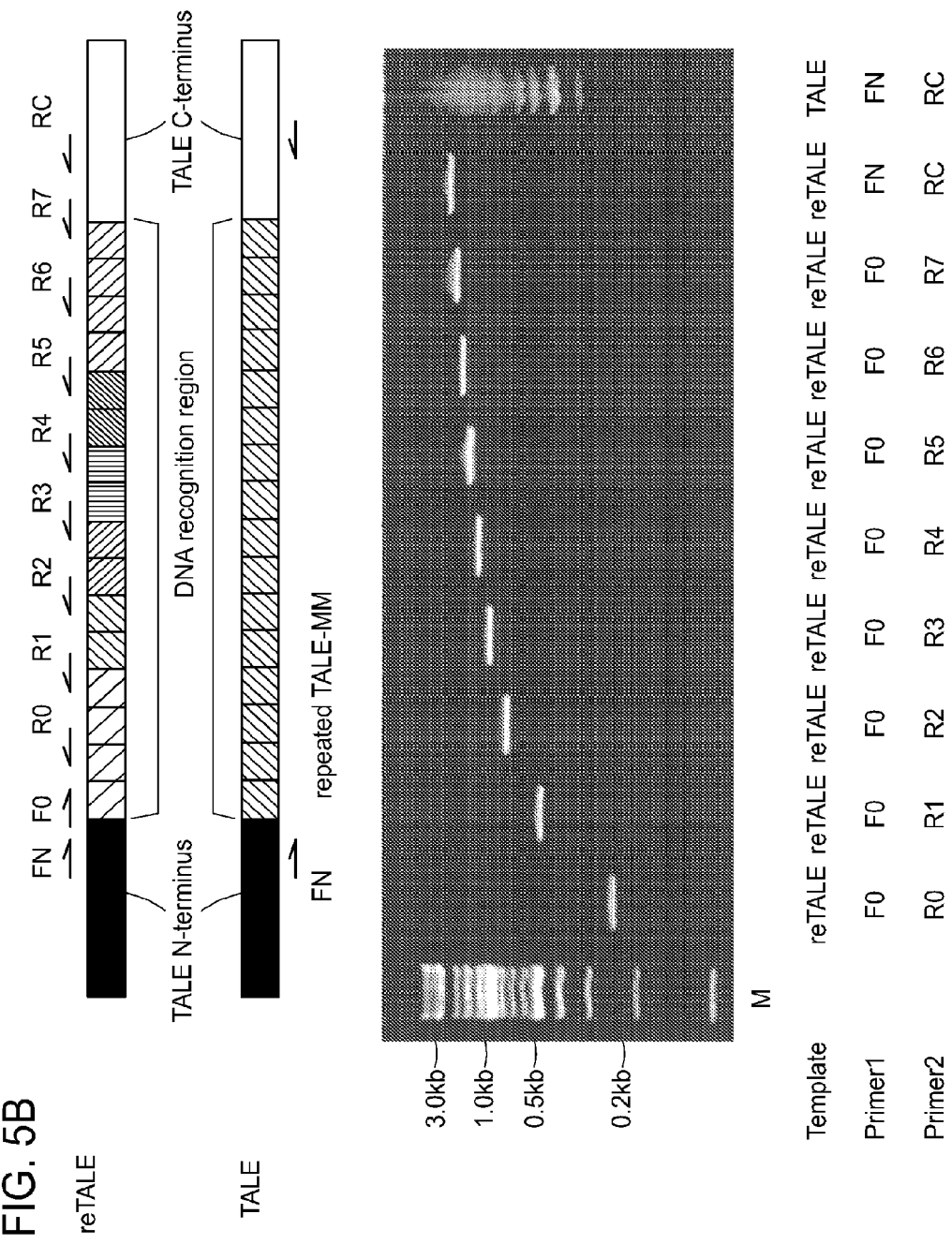

FIG. 5. Design of reTALE. (a) Sequence alignment of the original TALE RVD monomer with monomers in re-TALE-16.5 (re-TALE-M1→re-TALE-M17) (SEQ ID NO:222) and (SEQ ID NOs:2-19). Nucleotide alterations from the original sequence are highlighted in gray. (b) Test of repetitiveness of re-TALE by PCR. Top panel illustrates the structure of re-TALE/TALE and positions of the primers in the PCR reaction. Bottom panel illustrates PCR bands with condition indicated below. The PCR laddering presents with the original TALE template (right lane).

Figure 6A:
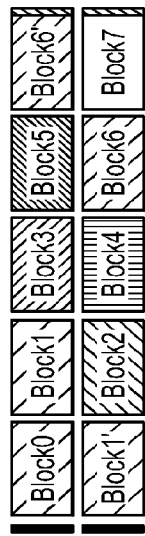
Figure 6B:
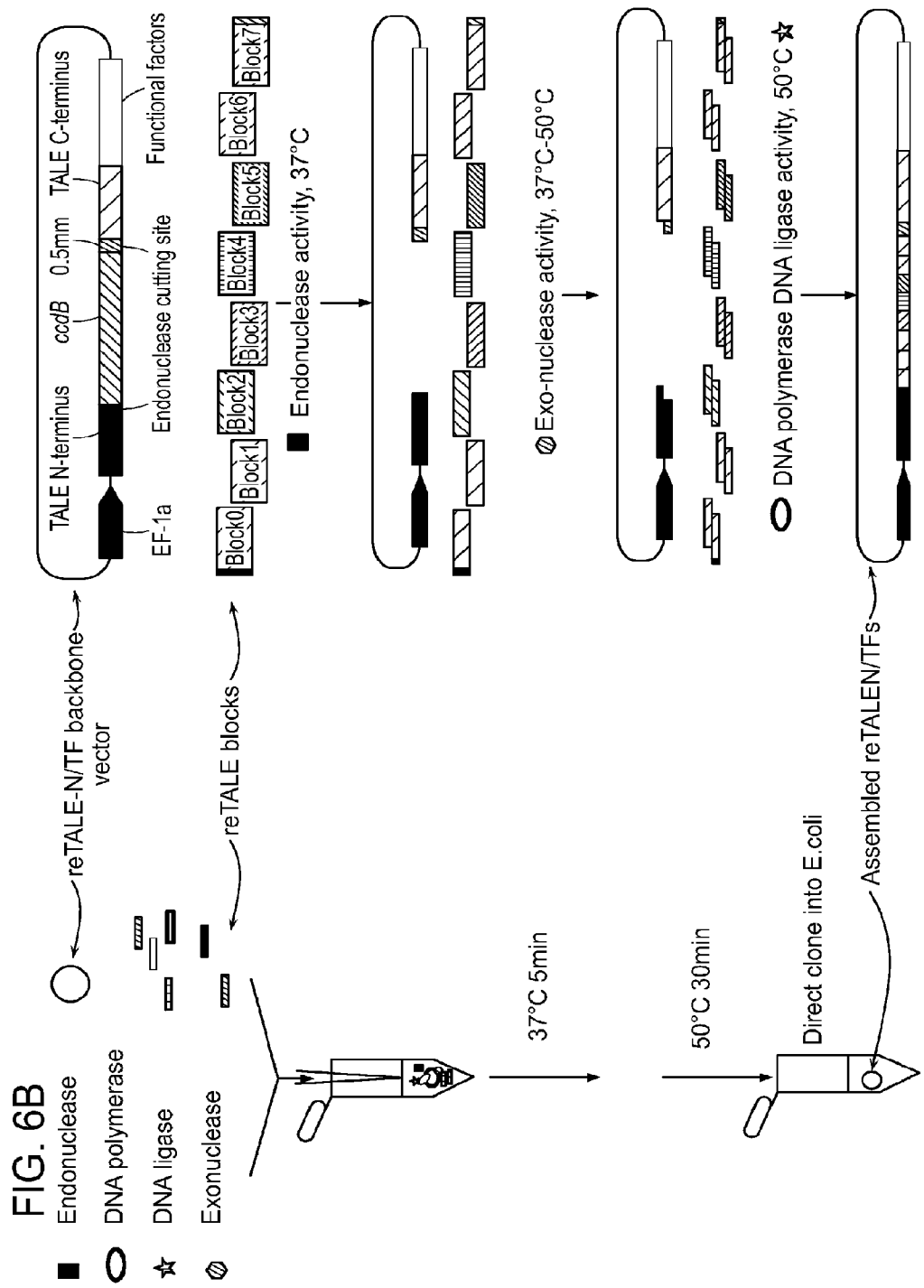
Figure 6C:
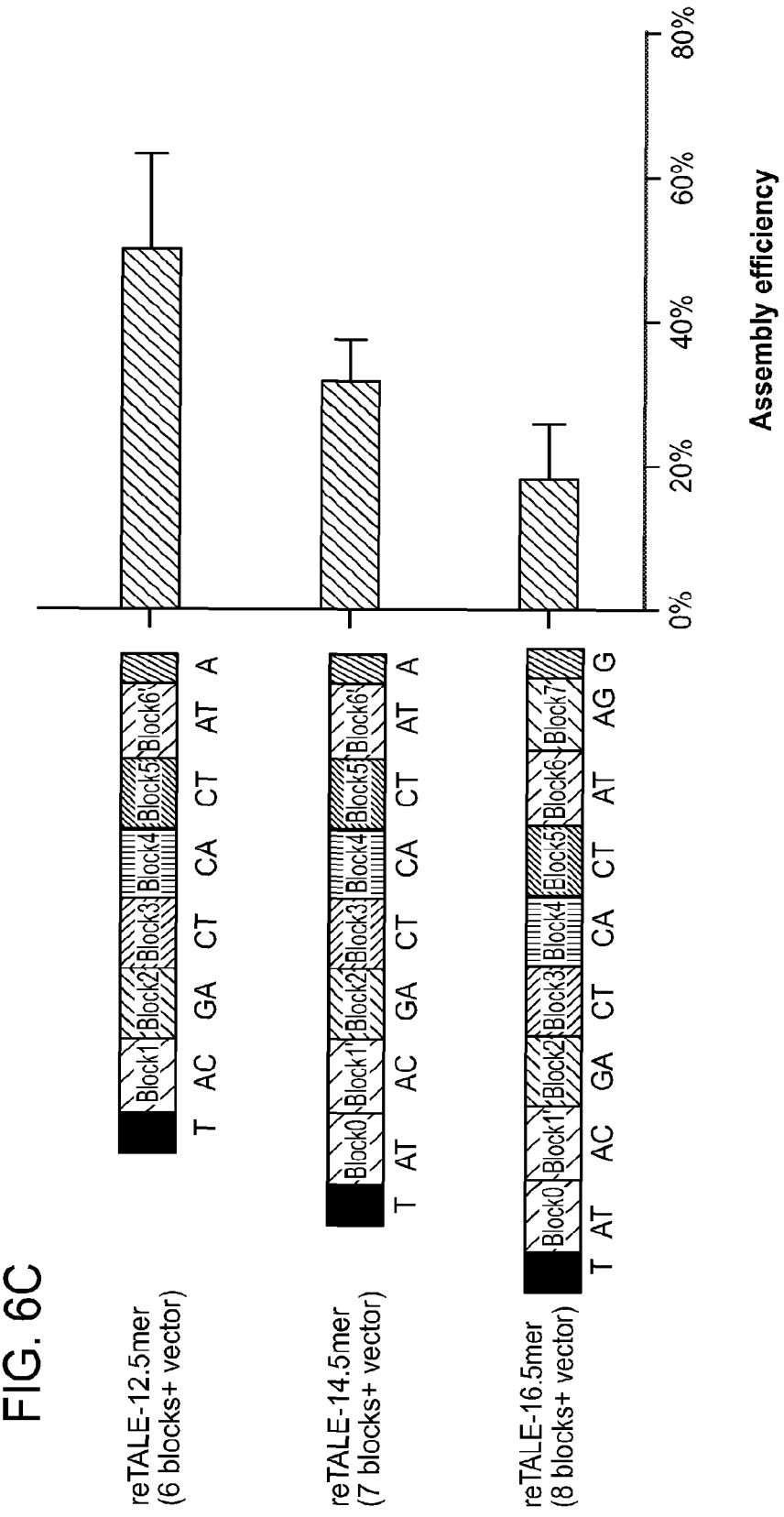

FIG. 6. Design and practice of TALE Single-incubation Assembly (TASA) assembly.

(a) Schematic representation of the library of re-TALE dimer blocks for TASA assembly. There is a library of 10 re-TALE dimer blocks encoding two RVDs. Within each block, all 16 dimers share the same DNA sequence except the RVD encoding sequences; Dimers in different blocks have distinct sequences but are designed such that they share 32 bp overlaps with the adjacent blocks. DNA and amino acid sequence of one dimer (Block 6_AC) are listed on the right. (SEQ ID NOs:223-224).

(b) Schematic representation of TASA assembly. The left panel illustrates the TASA assembly method: a one-pot incubation reaction is conducted with an enzyme mixture/ re-TALE blocks/re-TALE-N/TF backbone vectors. The reaction product can be used directly for bacterial transformation. The right panel illustrates the mechanism of TASA. The destination vector is linearized by an endonuclease at 37° C. to cut off ccdB counter-selection cassette; the exonuclease, which processes the end of blocks and linearized vectors, exposes ssDNA overhangs at the end of fragments to allow blocks and vector backbones to anneal in a designated order. When the temperature rises up to 50° C., polymerases and ligases work together to seal the gap, producing the final constructs ready for transformation.

(c) TASA assembly efficiency for re-TALEs possessing different monomer lengths. The blocks used for assembly are illustrated on the left and the assembly efficiency is presented on the right.

Figure 7A:
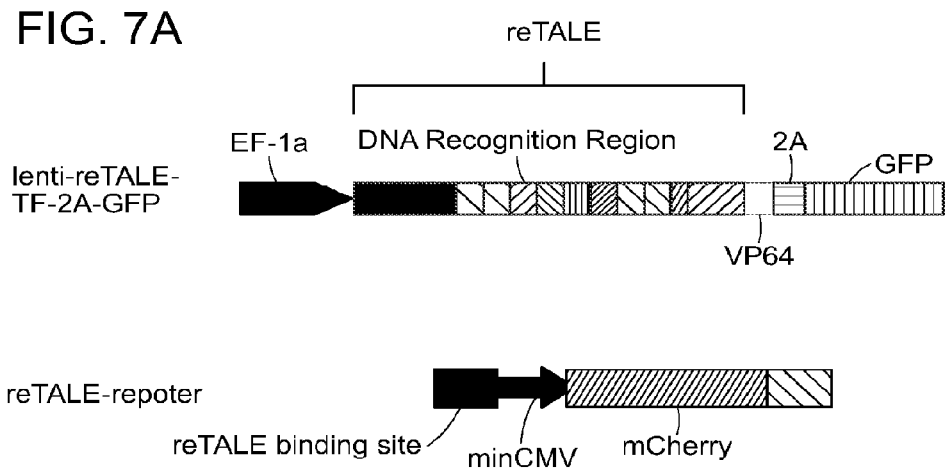
Figure 7B:
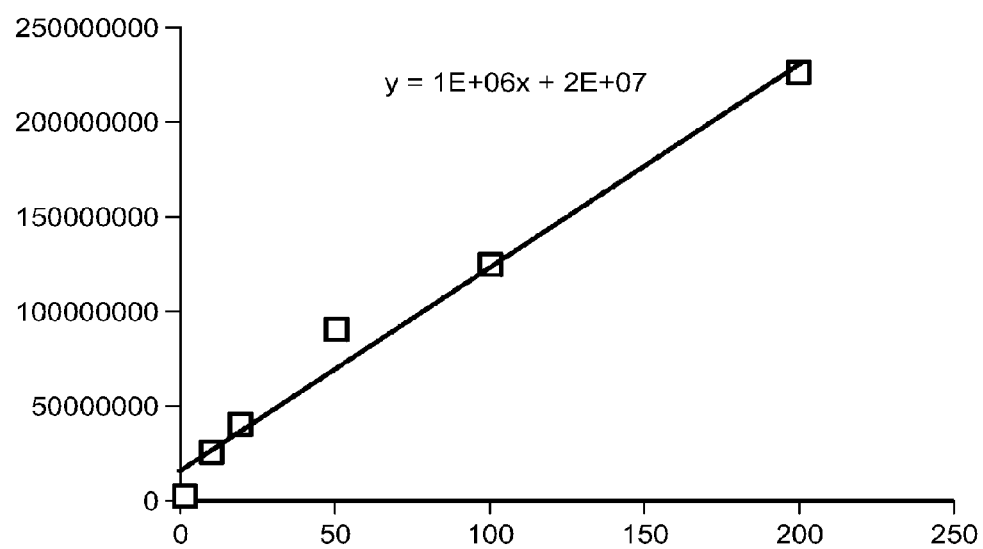
Figure 7D:
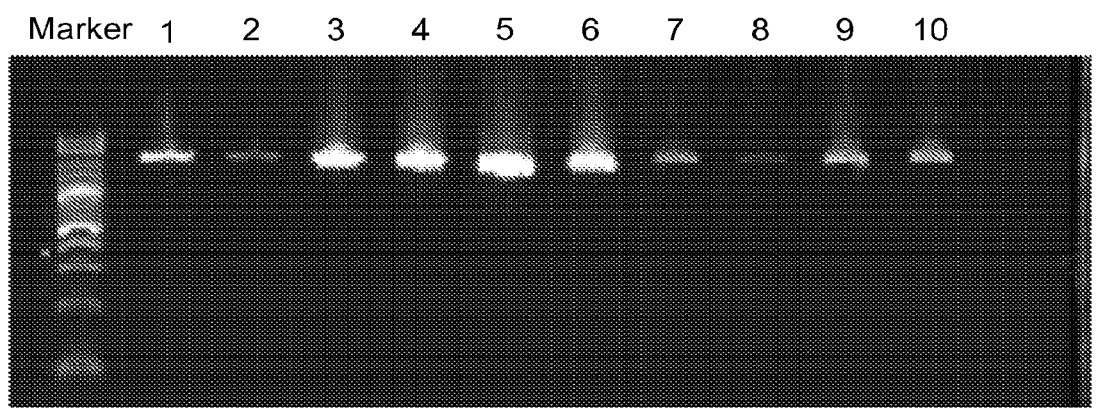

FIG. 7. The functionality and sequence integrity of Lenti-reTALEs.

Figure 8A:
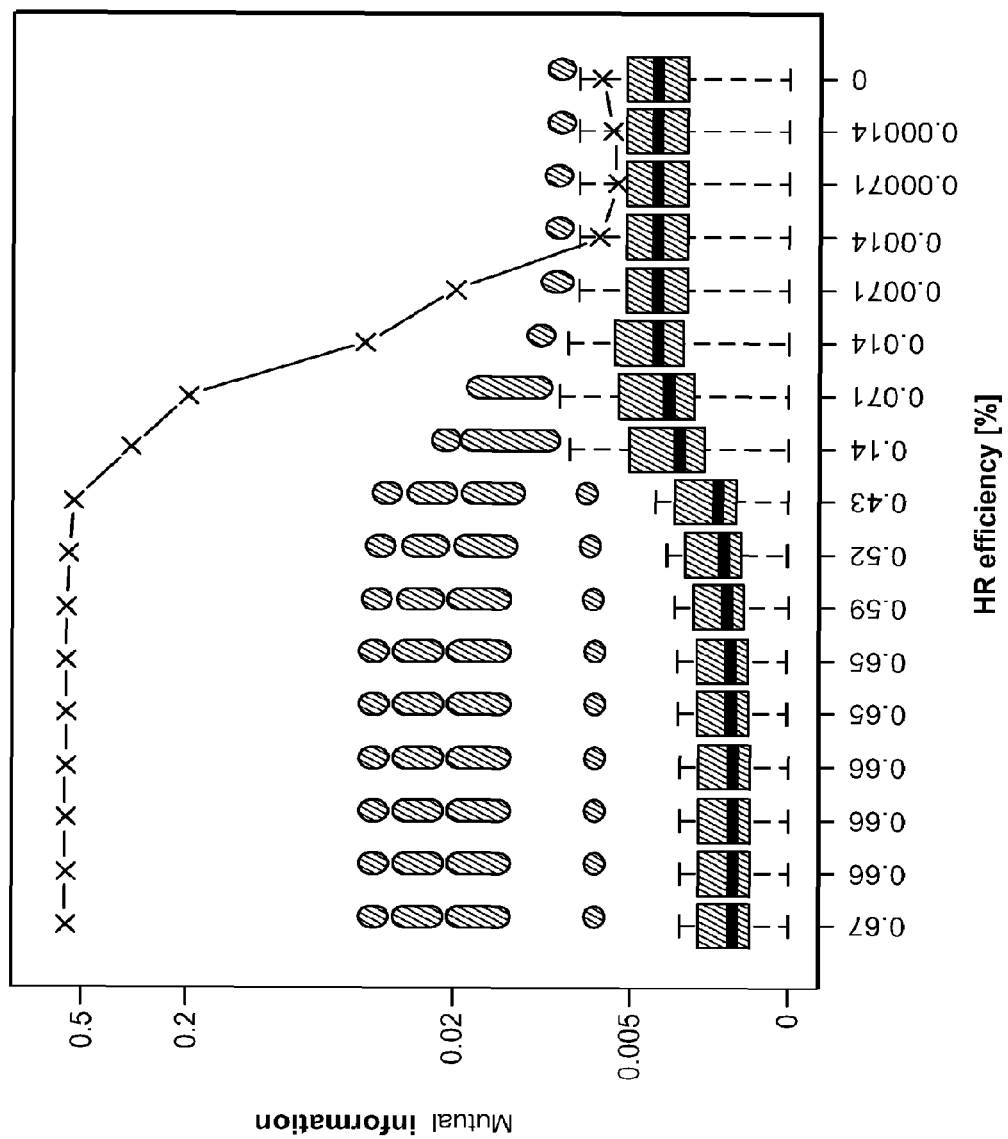
Figure 8B:
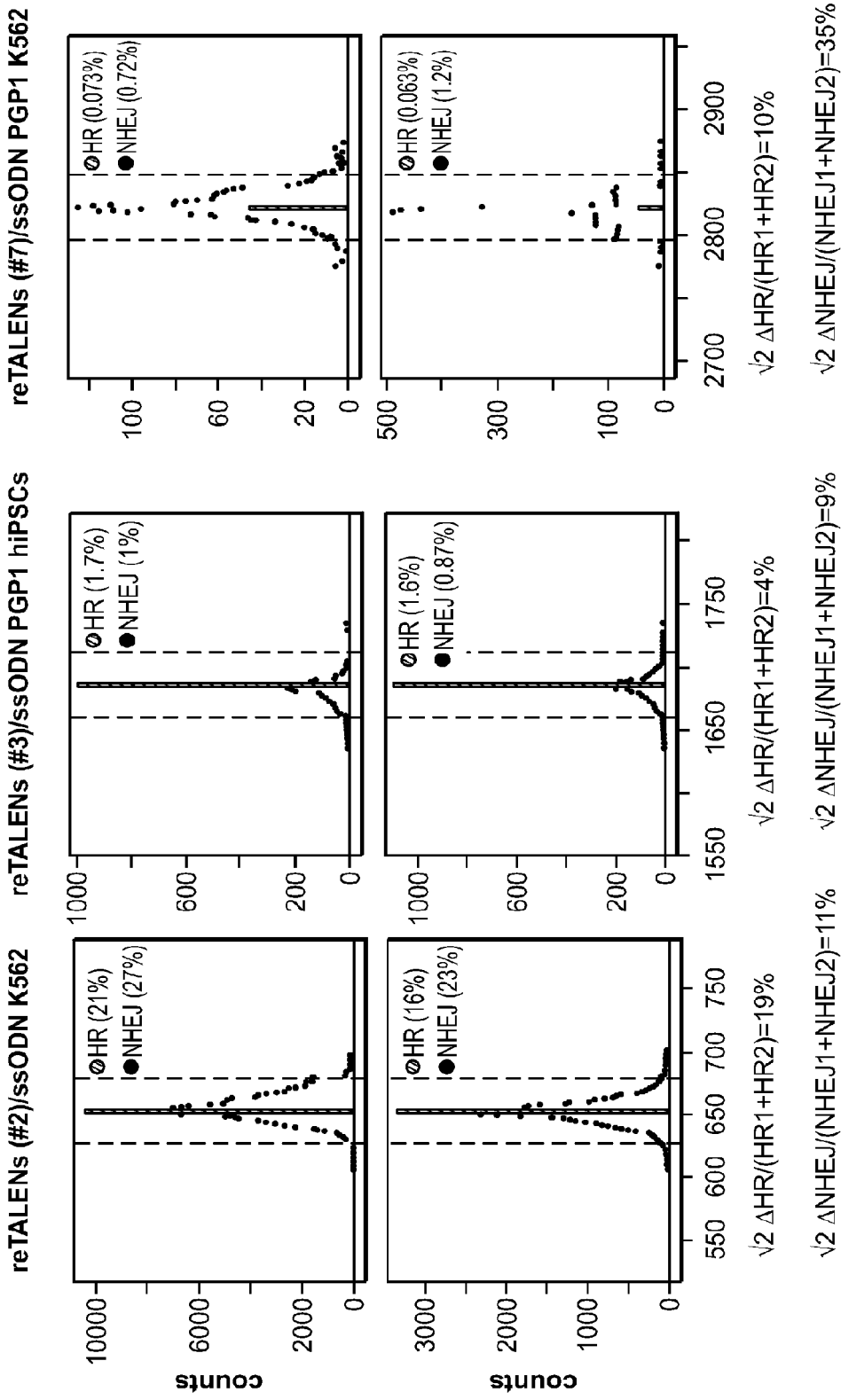

FIG. 8. The sensitivity and reproducibility of GEAS.
(A) Information-based analysis of HDR detection limit Given the dataset of re-TALENs (#10)/ssODN, the reads containing the expected editing (HDR) were identified and these HDR reads were systematically removed to generate different artificial datasets with a "diluted" editing signal. Datasets with 100, 99.8, 99.9, 98.9, 97.8, 89.2, 78.4, 64.9, 21.6, 10.8, 2.2, 1.1, 0.2, 0.1, 0.02, and 0% removal of HDR reads were generated to generate artificial datasets with HR efficiency ranging from 0-0.67%. For each individual dataset, mutual information (MI) of the background signal (in purple) and the signal obtained in the targeting site (in green) was estimated. MI at the targeting site is remarkably higher than the background when the HDR efficiency is above 0.0014%. A limit of HDR detection between 0.0014% and 0.0071% was estimated. MI calculation is described herein.
(B) The test of reproducibility of genome editing assessment system. The pairs of plots (Top and Bottom) show the HDR and NHEJ assessment results of two replicates with re-TALENs pair and cell type indicated above. For each experiment, nucleofection, targeted genome amplification, deep-sequencing and data analysis were conducted independently. The genome editing assessment variation of replicates was calculated as $\sqrt{2}$ (|HDR1−HDR2|)/((HDR+HDR2)/2)=$\Delta$HDR/HDR and $\sqrt{2}$ (|NHEJ1−NHEJ2|)/((NHEJ1+NHEJ2)/2)=$\Delta$NHEJ/NHEJ and the variation results are listed below the plots. The average variation of the system was (19%+11%+4%+9%+10%+35%)/6=15%. Factors that may contribute to the variations include the status of cells under nucleofection, nucleofection efficiency, and sequencing coverage and quality.

Figure 9A:
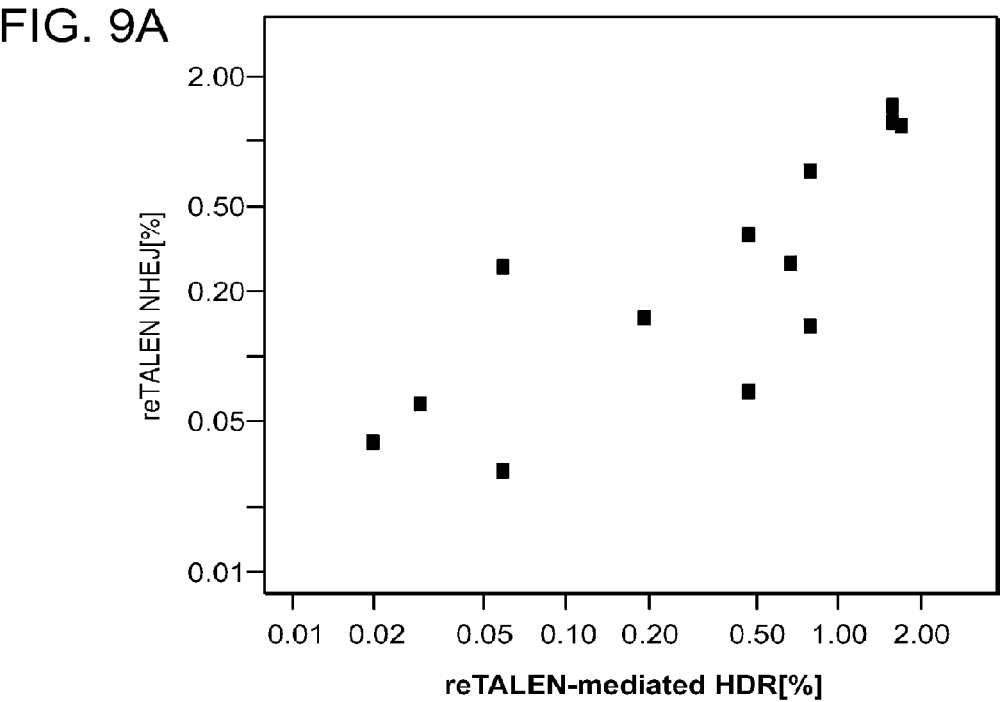
Figure 9B:
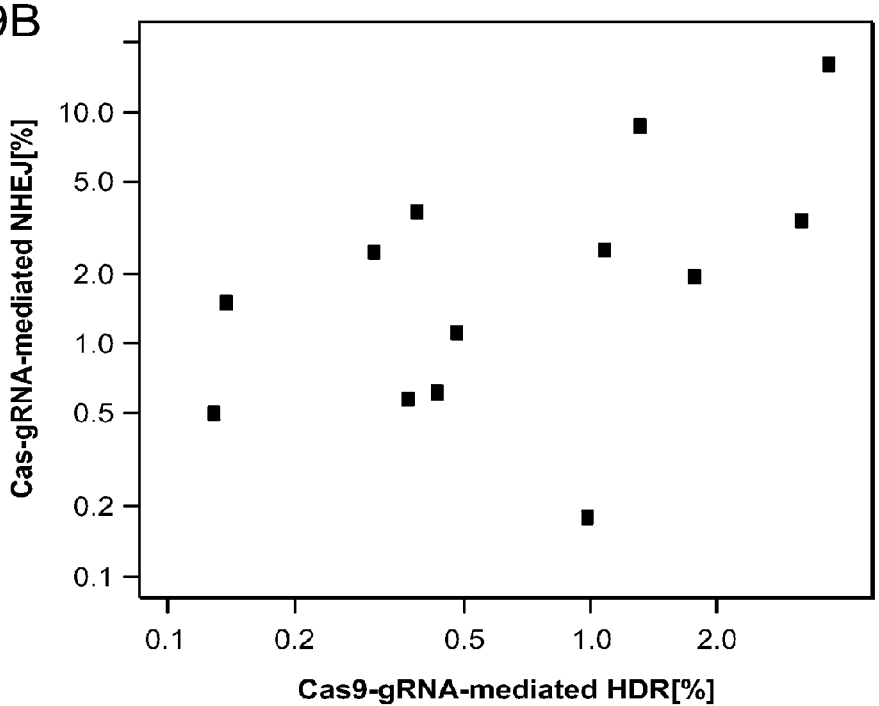
Figure 9C:
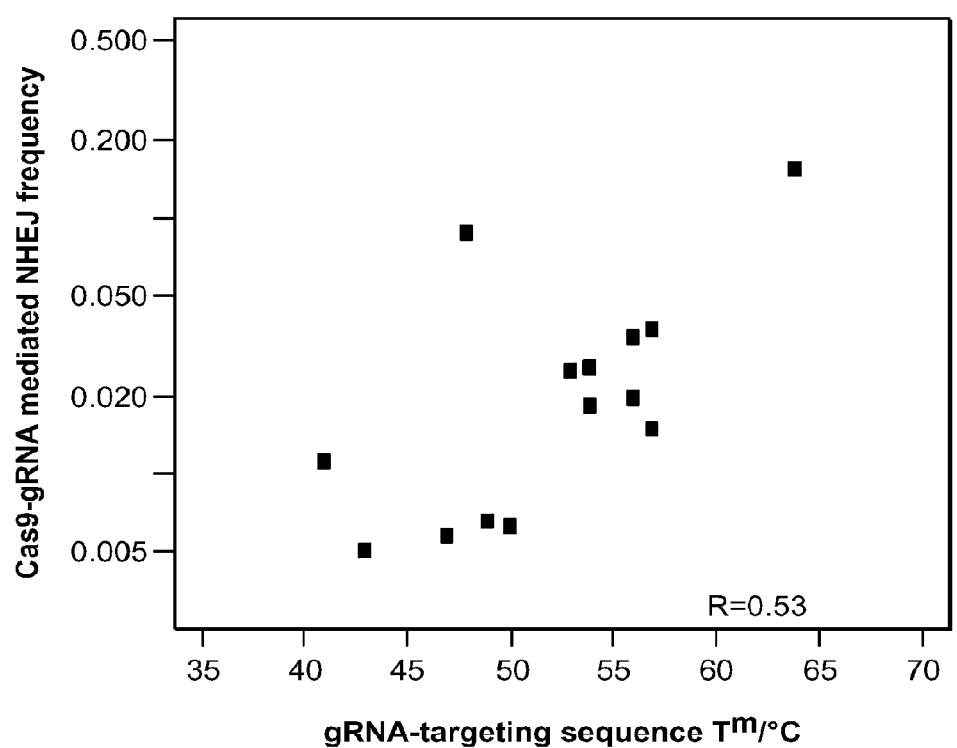

FIG. 9. Statistical analysis of NHEJ and HDR efficiencies by reTALENs and Cas9-gRNAs on CCR5.
(a) The correlation of HR and NHEJ efficiencies mediated by reTALENs at identical sites in iPSCs (r=0.91, P<1× 10-5).
(b) The correlation of HR and NHEJ efficiencies mediated by Cas9-gRNA at identical sites in iPSCs (r=0.74, P=0.002).
(c) The correlation of NHEJ efficiencies mediated by Cas9-gRNA and the Tm temperature of gRNA targeting site in iPSCs (r=0.52, P=0.04)

Figure 10:
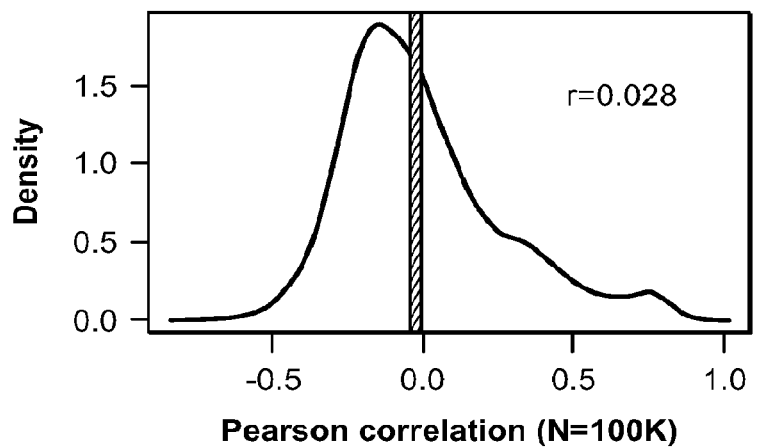
Figure 10:
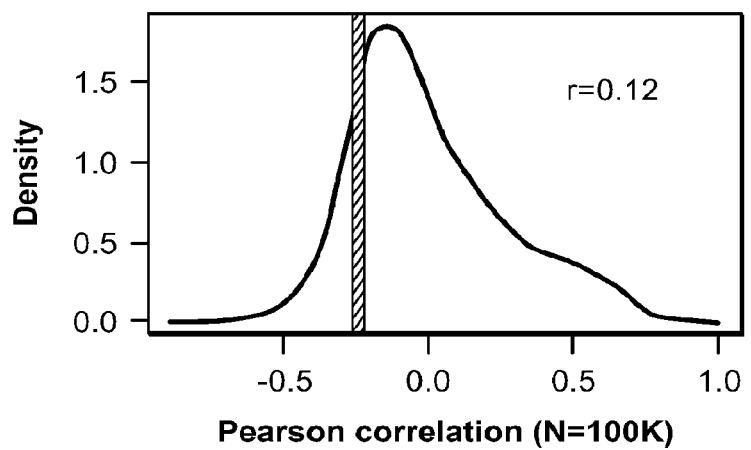
Figure 10:
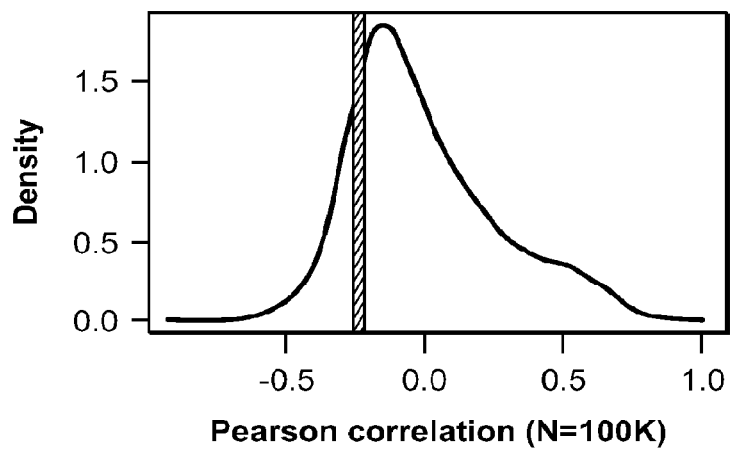

FIG. 10. The correlation analysis of genome editing efficiency and epigenetic state. Pearson correlation was used to study possible associations between DNase I sensitivity and genome engineering efficiencies (HR, NHEJ). The observed correlation was compared to a randomized set (N=100000). Observed correlations higher than the 95th percentile, or lower than the 5th percentile of the simulated distribution were considered as potential associations. No remarkable correlation between DNase1 sensitivity and NHEJ/HR efficiencies was observed.

Figure 11A:
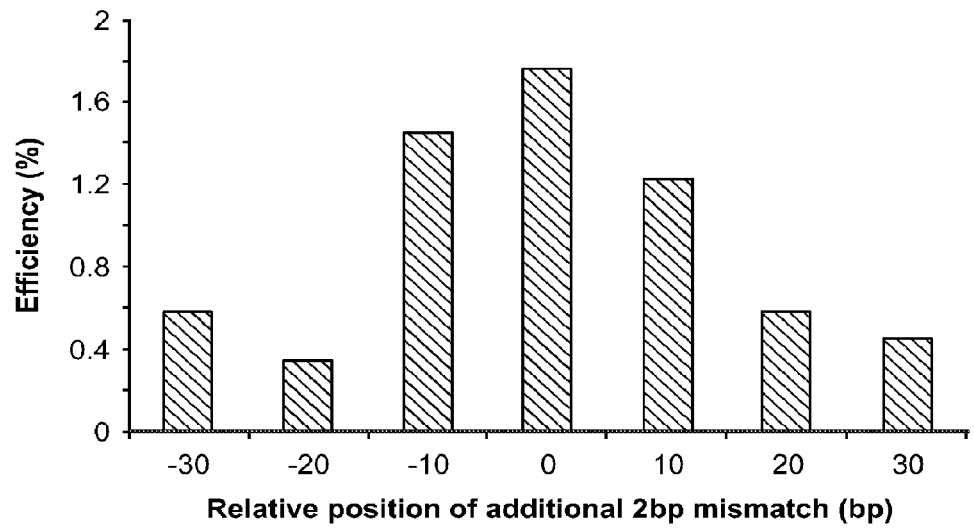
Figure 11B:
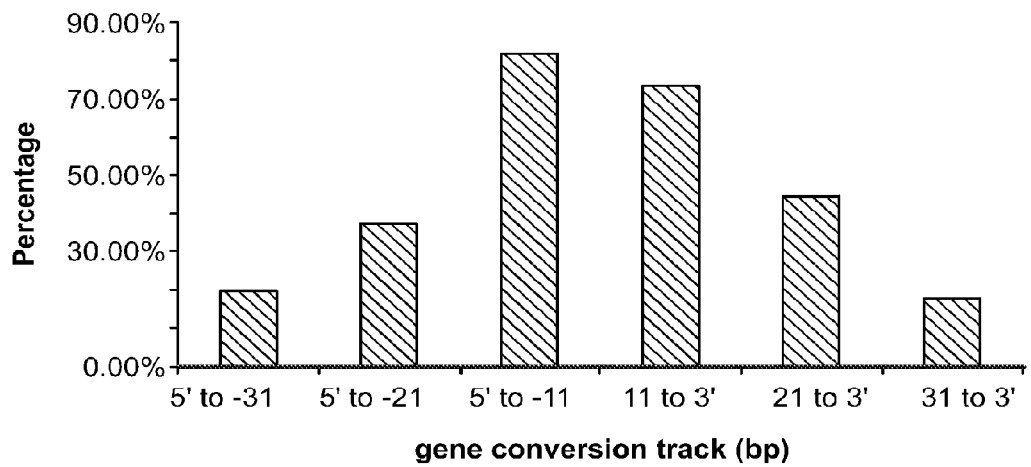

FIG. 11. The impact of homology pairing in the ssODN-mediated genome editing.
(a) In the experiment described in FIG. 3b, overall HDR as measured by the rate at which the middle 2b mismatch (A) was incorporated decreased as the secondary mismatches B increased their distance from the A (relative position of B to A varies from −30→30 bp). The higher rates of incorporation when B is only 10 bp away from A (−10 bp and +10b) may reflect a lesser need for pairing of the ssODN against genomic DNA proximal to the dsDNA break.
(b) Distribution of gene conversion lengths along the ssODN. At each distance of B from A, a fraction of HDR events incorporates only A while another fraction incorporates both A and B. These two events may be interpretable in terms of gene conversion tracts (Elliott et al., 1998), whereby A+B events represent long conversion tracts that extend beyond B and A-only events represent shorter ones that do not reach to B. Under this interpretation, a distribution of gene conversion lengths in both directions along the oligo can be estimated (the middle of ssODN is defined as 0, conversion tracks towards the 5' end of ssODN as − direction, and 3' end as + direction). Gene conversion tracts progressively decrease in incidence as their lengths increase, a result very similar to gene conversion tract distributions seen with dsDNA donors, but on a highly compressed distance scale of tens of by for the ssDNA oligo vs. hundreds of bases for dsDNA donors.
(c) Assays for gene conversion tracts using a single ssODN that contains a series of mutations and measuring contiguous series of incorporations. A ssODN donor with three pairs of 2 bp mismatches (orange) spaced at intervals of 10 nt on either side of the central 2 bp mismatch (Top) was used. Few genomic sequencing reads were detected (see reference 62 hereby incorporated by reference in its entirety) carrying >=1 mismatches defined by ssODN among >300,000 reads sequencing this region. All these reads were plotted (bottom) and the sequence of the reads was color coded. Orange: defined mismatches; green: wild type sequence. Genome editing with this ssODN gave rise to a pattern in which middle mutation alone was incorporated 85% (53/62) of the time, with multiple B mismatches incorporated at other times. Although numbers of B incorporation events were too low to estimate a distribution of tract lengths >10 bp, it is clear that the short tract region from −10-10 bp predominates.

Figure 12:
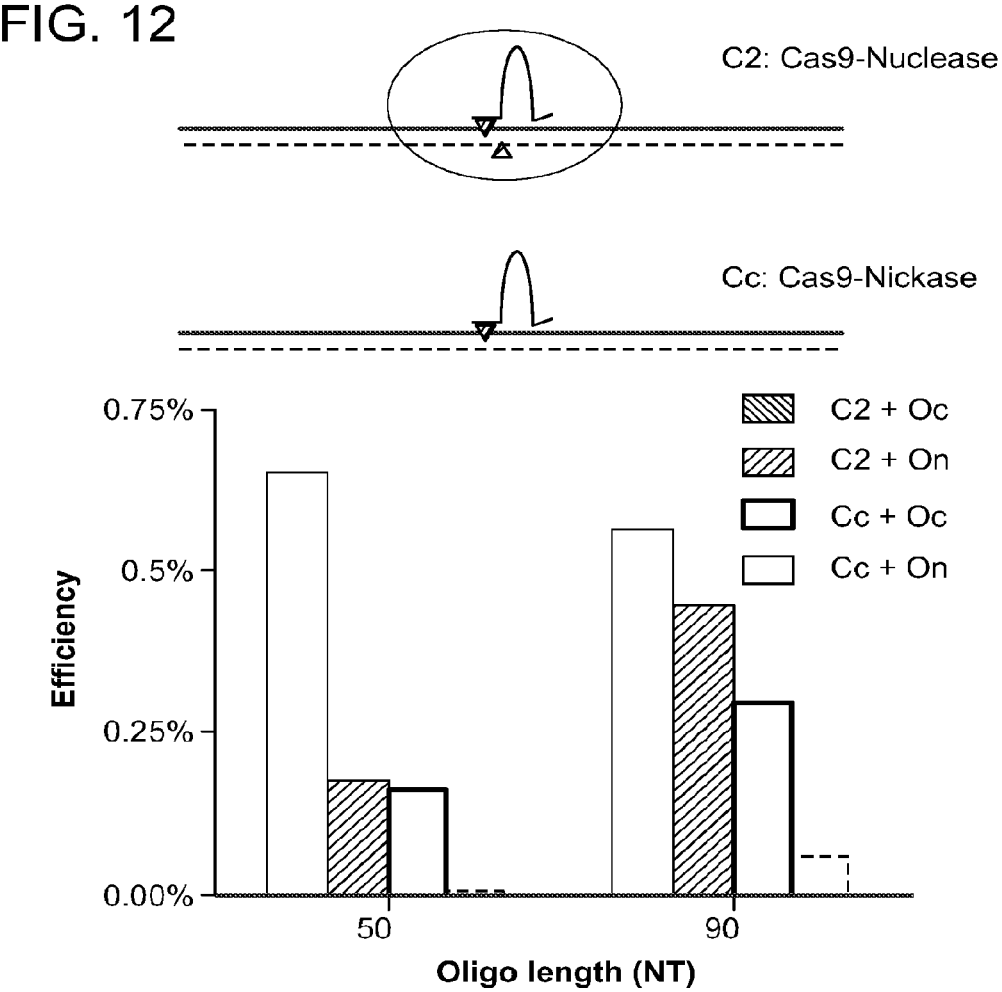

FIG. 12. Cas9-gRNA nuclease and nickases genome editing efficiencies.
PGP1 iPSCs were co-transfected with combination of nuclease (C2) (Cas9-gRNA) or nickase (Cc) (Cas9D10A-gRNA) and ssODNs of different orientation (Oc and On). All ssODNs possessed an identical 2 bp mismatch against the genomic DNA in the middle of their sequence. The assessment of HDR is described herein.

Figure 13:
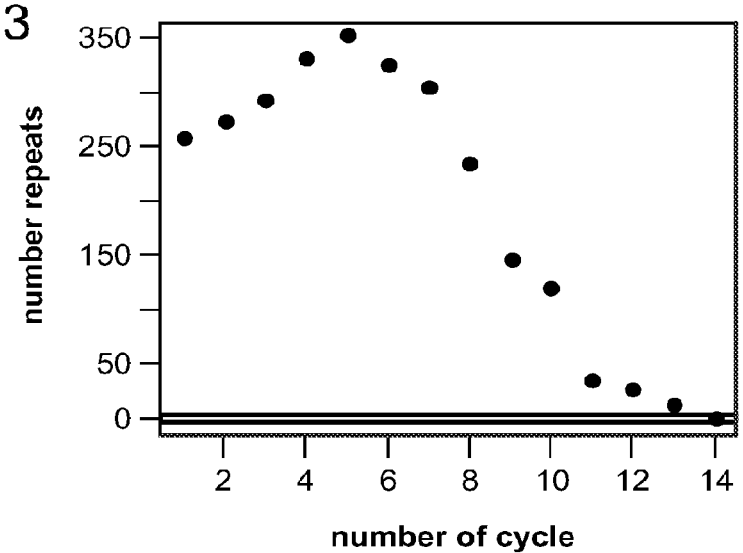

FIG. 13. The design and optimization of re-TALE sequence.
The re-TALE sequence was evolved in several design cycles to eliminate repeats. In each cycle, synonymous sequences from each repeat are evaluated. Those with the largest hamming distance to the evolving DNA are selected. The final sequence with cai=0.59 $\Delta$G=−9.8 kcal/mol. An R package was provided to carry out this general framework for synthetic protein design.

Figure 14:
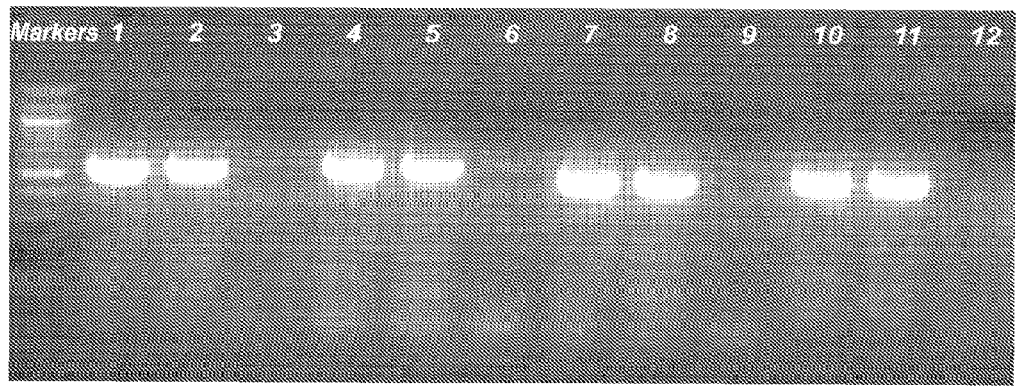

FIG. 14 is a gel image showing PCR validation of the genomic insertion of Cas 9 in PGP1 cells. Line 3, 6, 9, 12 are PCR product of plain PGP1 cell lines.

Figure 15:
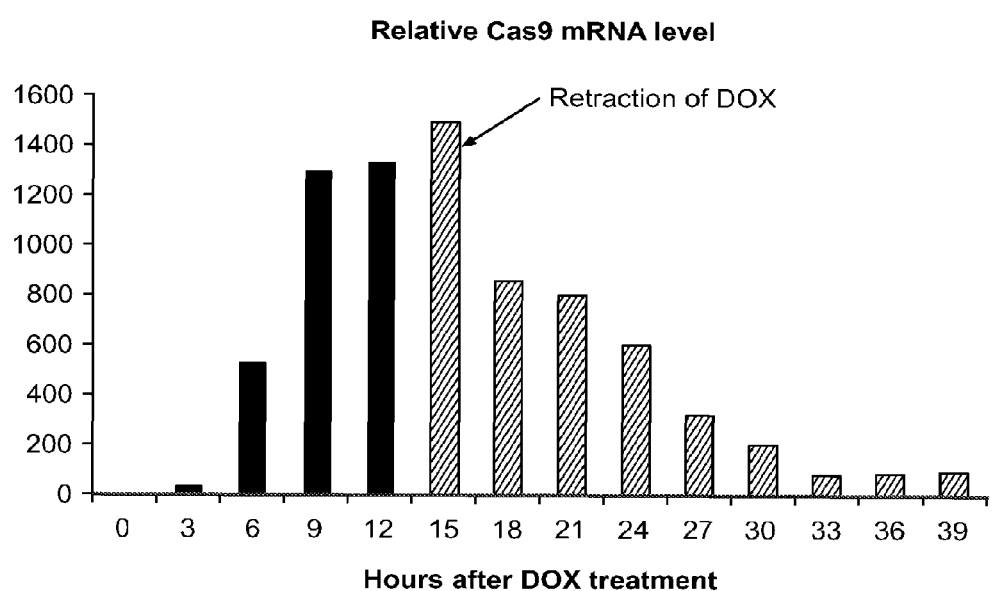

FIG. 15 is a graph of the mRNA expression level of Cas9 mRNA under the induction.

Figure 16:
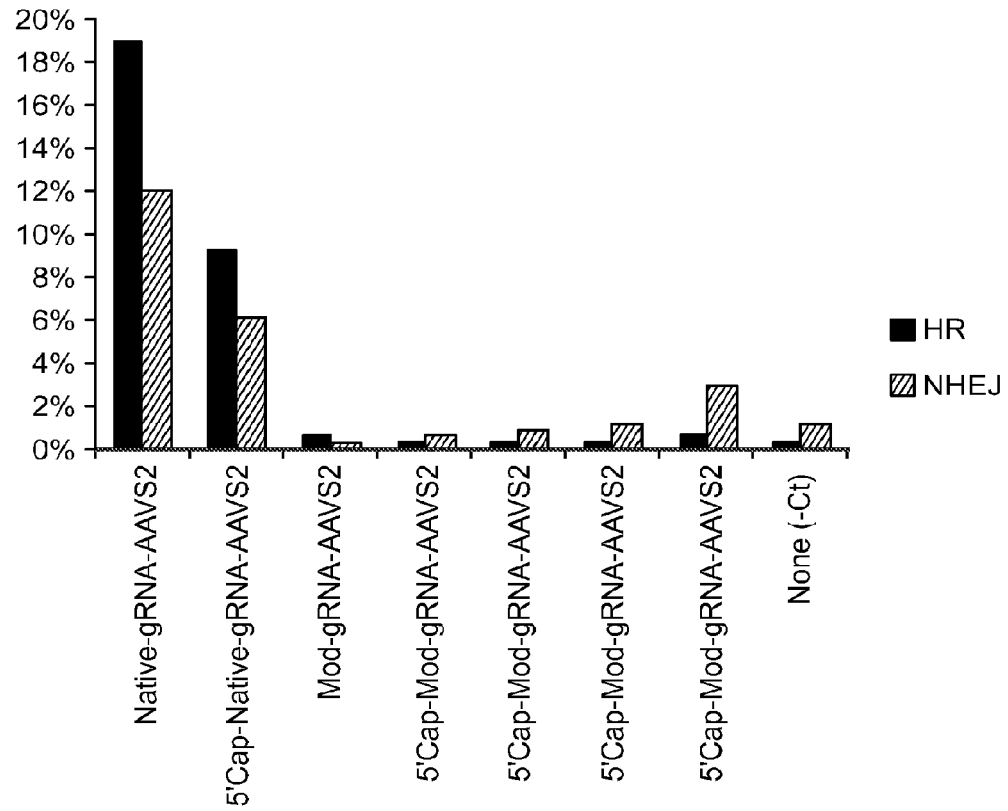

FIG. 16 is a graph showing genome targeting efficiency by different RNA designs.

Figure 17:
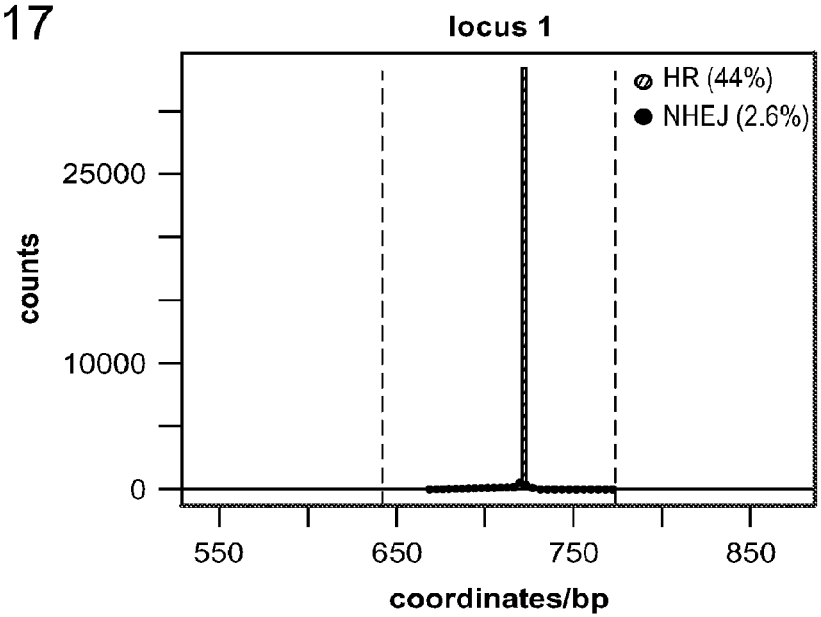

FIG. 17 is a graph showing genome targeting efficiency of 44% homologous recombination achieved by a guide RNA–donor DNA fusion.

Figure 18:
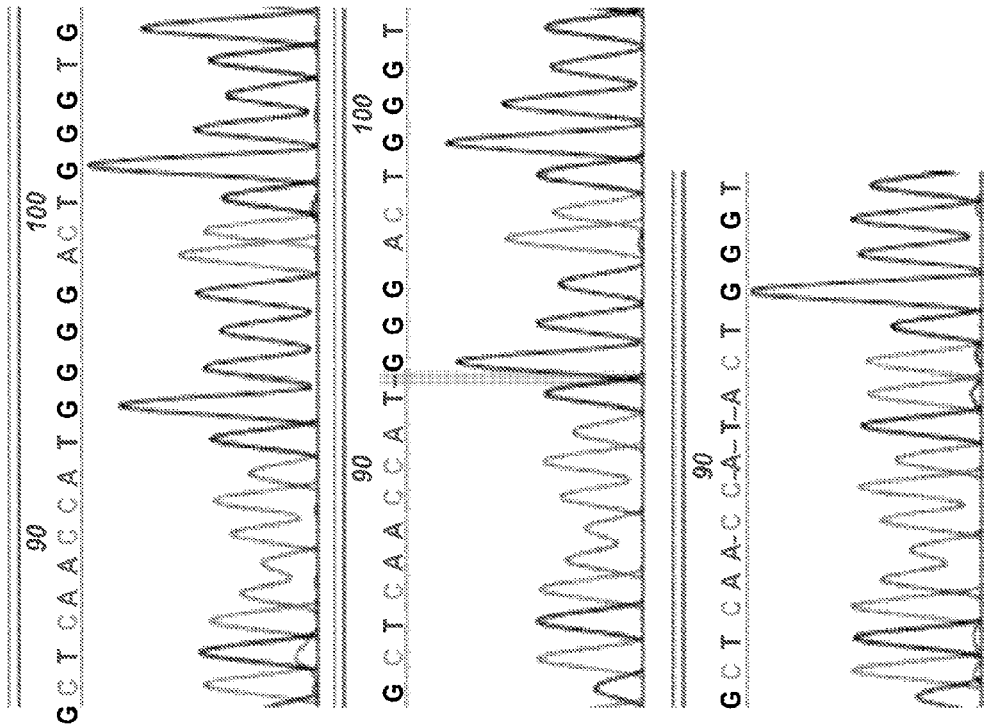

FIG. 18 is a diagram showing the genotype of isogenic PGP1 cell lines generated by system described herein. PGP1-iPS-BTHH has the single nucleotides deletion phenotype as the BTHH patient. PGP1-NHEJ has 4 bp deletions that generated frame-shift mutations in a different way.

Figure 19:
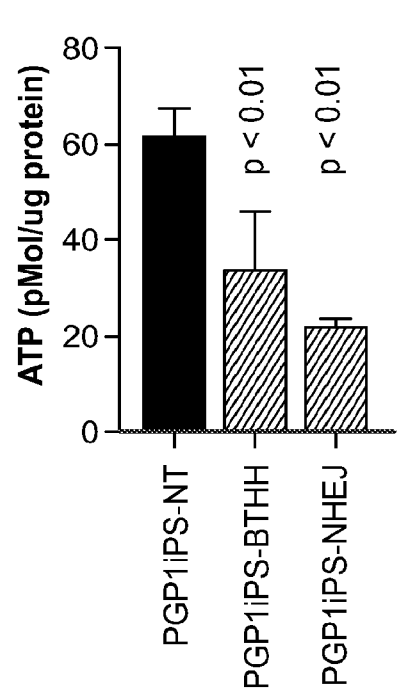
Figure 19:
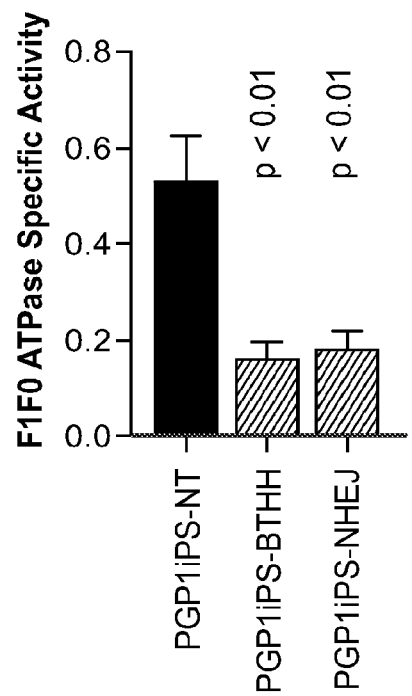

FIG. 19 is a graph showing that cardiomyocyte derived from isogenic PGP1 iPS recapitulated defective ATP production and F1F0 ATPase specific activity as demonstrated in patient specific cells.

FIG. 20A-20F depicts re-TALEN-backbone sequence (SEQ ID NOs:20-21).

DETAILED DESCRIPTION

Aspects of the present invention are directed to the use of a TALEN that lacks certain repeat sequences, for nucleic acid engineering, for example by cutting double stranded nucleic acid. The use of the TALEN to cut double stranded nucleic acid can result in nonhomologous end joining (NHEJ) or homologous recombination (HR). Aspects of the present disclosure also contemplate the use of a TALEN that lacks repeat sequences for nucleic acid engineering, for example by cutting double stranded nucleic acid, in the presence of a donor nucleic acid and insertion of the donor nucleic acid into the double stranded nucleic acid, such as by nonhomologous end joining (NHEJ) or homologous recombination (HR).

Transcription activator-like effector nucleases (TALENs) are known in the art and include artificial restriction enzymes generated by fusing a TAL effector DNA binding domain to a DNA cleavage domain. Restriction enzymes are enzymes that cut DNA strands at a specific sequence. Transcription activator-like effectors (TALEs) can be engineered to bind to a desired DNA sequence. See Boch, Jens (February 2011). "TALEs of genome targeting". Nature Biotechnology 29 (2): 135-6 hereby incorporated by reference in its entirety. By combining such an engineered TALE with a DNA cleavage domain (which cuts DNA strands), a TALEN is produced which is a restriction enzyme that is specific for any desired DNA sequence. According to certain aspects, the TALEN is introduced into a cell for target nucleic acid editing in situ, such as genome editing in situ.

According to one aspect, the non-specific DNA cleavage domain from the end of the FokI endonuclease can be used to construct hybrid nucleases that are active in yeast cells, plant cells and animal cells. The FokI domain functions as a dimer, requiring two constructs with unique DNA binding domains for sites in the target genome with proper orientation and spacing. Both the number of amino acid residues between the TALE DNA binding domain and the FokI cleavage domain and the number of bases between the two individual TALEN binding sites affect activity.

The relationship between amino acid sequence and DNA recognition of the TALE binding domain allows for designable proteins. Software programs such as DNAWorks can be used to design TALE constructs. Other methods of designing TALE constructs are known to those of skill in the art. See Cermak, T.; Doyle, E. L.; Christian, M.; Wang, L.; Zhang, Y.; Schmidt, C.; Bailer, J. A.; Somia, N. V. et al. (2011). "Efficient design and assembly of custom TALEN and other TAL effector-based constructs for DNA targeting". Nucleic Acids Research. doi:10.1093/nar/gkr218; Zhang, Feng; et. al. (February 2011). "Efficient construction of sequence-specific TAL effectors for modulating mammalian transcription", Nature Biotechnology 29 (2): 149-53; Morbitzer, R.; Elsaesser, J.; Hausner, J.; Lahaye, T. (2011). "Assembly of custom TALE-type DNA binding domains by modular cloning". Nucleic Acids Research. doi:10'1093/nar/gkr151; Li, T.; Huang, S.; Zhao, X.; Wright, D. A.; Carpenter, S.; Spalding, M. H.; Weeks, D. P.; Yang, B. (2011). "Modularly assembled designer TAL effector nucleases for targeted gene knockout and gene replacement in eukaryotes". "Nucleic Acids Research. doi" 10.1093/nar/gkr188; Geißler, R.; Scholze, H.; Hahn, S.; Streubel, J.; Bonas, U.; Behrens, S. E.; Boch, J. (2011). "Transcriptional Activators of Human Genes with Programmable DNA-Specificity". In Shiu, Shin-Han. PLoS ONE 6 (5): e19509; Weber, E.; Gruetzner, R.; Werner, S.; Engler, C.; Marillonnet, S. (2011). "Assembly of Designer TAL Effectors by Golden Gate Cloning". In Bendahmane, Mohammed. PLoS ONE 6 (5): e19722 hereby incorporated by reference in their entireties.

According to an exemplary aspect, once the TALEN genes have been assembled they may inserted into plasmids according to certain embodiments; the plasmids are then used to transfect the target cell where the gene products are expressed and enter the nucleus to access the genome. According to exemplary aspects, TALENs as described herein can be used to edit target nucleic acids, such as genomes, by inducing double-strand breaks (DSB), which cells respond to with repair mechanisms. Exemplary repair mechanisms include non-homologous end joining (NHEJ) which reconnects DNA from either side of a double-strand break where there is very little or no sequence overlap for annealing. This repair mechanism induces errors in the genome via insertion or deletion (indels), or chromosomal rearrangement; any such errors may render the gene products coded at that location non-functional. See Miller, Jeffrey; et. al. (February 2011). "A TALE nuclease architecture for efficient genome editing". Nature Biotechnology 29 (2): 143-8 hereby incorporated by reference in its entirety. Because this activity can vary depending on the species, cell type, target gene, and nuclease used, the activity can be monitored by using a heteroduplex cleavage assay which detects any difference between two alleles amplified by PCR. Cleavage products can be visualized on simple agarose gels or slab gel systems.

Alternatively, DNA can be introduced into a genome through NHEJ in the presence of exogenous double-stranded DNA fragments. Homology directed repair can also introduce foreign DNA at the DSB as the transfected double-stranded sequences are used as templates for the repair enzymes. According to certain aspects the TALENs described herein can be used to generate stably modified human embryonic stem cell and induced pluripotent stem cell (IPSCs) clones. According to certain aspects the TALENs described herein can be used to generate knockout species such as C. elegans, knockout rats, knockout mice or knockout zebrafish.

According to one aspect of the present disclosure, embodiments are directed to the use of exogenous DNA, nuclease enzymes such as DNA binding proteins and guide RNAs to co-localize to DNA within a stem cell and digest or cut the DNA with insertion of the exogenous DNA. Such DNA binding proteins are readily known to those of skill in the art to bind to DNA for various purposes. Such DNA binding proteins may be naturally occurring. DNA binding proteins included within the scope of the present disclosure include those which may be guided by RNA, referred to herein as guide RNA. According to this aspect, the guide RNA and the RNA guided DNA binding protein form a co-localization complex at the DNA. Such DNA binding proteins having nuclease activity are known to those of skill in the art, and include naturally occurring DNA binding proteins having nuclease activity, such as Cas9 proteins present, for example, in Type II CRISPR systems. Such Cas9 proteins and Type II CRISPR systems are well documented in the art. See Makarova et al., Nature Reviews, Microbiology, Vol. 9, June 2011, pp. 467-477 including all supplementary information hereby incorporated by reference in its entirety.

Exemplary DNA binding proteins having nuclease activity function to nick or cut double stranded DNA. Such nuclease activity may result from the DNA binding protein having one or more polypeptide sequences exhibiting nuclease activity. Such exemplary DNA binding proteins may have two separate nuclease domains with each domain responsible for cutting or nicking a particular strand of the double stranded DNA. Exemplary polypeptide sequences having nuclease activity known to those of skill in the art include the McrA-HNH nuclease related domain and the RuvC-like nuclease domain. Accordingly, exemplary DNA binding proteins are those that in nature contain one or more of the McrA-HNH nuclease related domain and the RuvC-like nuclease domain.

An exemplary DNA binding protein is an RNA guided DNA binding protein of a Type II CRISPR System. An exemplary DNA binding protein is a Cas9 protein.

In *S. pyogenes*, Cas9 generates a blunt-ended double-stranded break 3 bp upstream of the protospacer-adjacent motif (PAM) via a process mediated by two catalytic domains in the protein: an HNH domain that cleaves the complementary strand of the DNA and a RuvC-like domain that cleaves the non-complementary strand. See Jinke et al., Science 337, 816-821 (2012) hereby incorporated by reference in its entirety. Cas9 proteins are known to exist in many Type II CRISPR systems including the following as identified in the supplementary information to Makarova et al., Nature Reviews, Microbiology, Vol. 9, June 2011, pp. 467-477: Methanococcus maripaludis C7; *Corynebacterium diphtheriae*; *Corynebacterium efficiens* YS-314; *Corynebacterium glutamicum* ATCC 13032 Kitasato; *Corynebacterium glutamicum* ATCC 13032 Bielefeld; *Corynebacterium glutamicum* R; *Corynebacterium kroppenstedtii* DSM 44385; *Mycobacterium abscessus* ATCC 19977; *Nocardia farcinica* IFM10152; *Rhodococcus erythropolis* PR4; *Rhodococcus jostii* RHA1; *Rhodococcus opacus* B4 uid36573; *Acidothermus cellulolyticus* 11B; *Arthrobacter chlorophenolicus* A6; *Kribbella flavida* DSM 17836 uid43465; *Thermomonospora curvata* DSM 43183; *Bifidobacterium dentium* Bd1; *Bifidobacterium longum* DJO10A; *Slackia heliotrinireducens* DSM 20476; *Persephonella marina* EX H1; *Bacteroides fragilis* NCTC 9434; *Capnocytophaga ochracea* DSM 7271; *Flavobacterium psychrophilum* JIP02 86; *Akkermansia muciniphila* ATCC BAA 835; *Roseiflexus castenholzii* DSM 13941; *Roseiflexus* RS1; *Synechocystis* PCC6803; *Elusimicrobium minutum* Pei191; uncultured Termite group 1 bacterium phylotype Rs D17; *Fibrobacter succinogenes* S85; *Bacillus cereus* ATCC 10987; *Listeria innocua*; *Lactobacillus casei*; *Lactobacillus rhamnosus* GG; *Lactobacillus salivarius* UCC118; *Streptococcus agalactiae* A909; *Streptococcus agalactiae* NEM316; *Streptococcus agalactiae* 2603; *Streptococcus dysgalactiae equisimilis* GGS 124; *Streptococcus equi zooepidemicus* MGCS10565; *Streptococcus gallolyticus* UCN34 uid46061; *Streptococcus gordonii* Challis subst CH1; *Streptococcus mutans* NN2025 uid46353; *Streptococcus mutans*; *Streptococcus pyogenes* M1 GAS; *Streptococcus pyogenes* MGAS5005; *Streptococcus pyogenes* MGAS2096; *Streptococcus pyogenes* MGAS9429; *Streptococcus pyogenes* MGAS10270; *Streptococcus pyogenes* MGAS6180; *Streptococcus pyogenes* MGAS315; *Streptococcus pyogenes* SSI-1; *Streptococcus pyogenes* MGAS10750; *Streptococcus pyogenes* NZ131; *Streptococcus thermophiles* CNRZ1066; *Streptococcus thermophiles* LMD-9; *Streptococcus thermophiles* LMG 18311; *Clostridium botulinum* A3 Loch Maree; *Clostridium botulinum* B Eklund 17B; *Clostridium botulinum* Ba4 657; *Clostridium botulinum* F Langeland; *Clostridium cellulolyticum* H10; *Finegoldia magna* ATCC 29328; *Eubacterium rectale* ATCC 33656; *Mycoplasma gallisepticum*; *Mycoplasma mobile* 163K; *Mycoplasma penetrans*; *Mycoplasma synoviae* 53; *Streptobacillus moniliformis* DSM 12112; *Bradyrhizobium* BTAi1; *Nitrobacter hamburgensis* X14; *Rhodopseudomonas palustris* BisB18; *Rhodopseudomonas palustris* BisB5; *Parvibaculum lavamentivorans* DS-1; *Dinoroseobacter shibae* DFL 12; *Gluconacetobacter diazotrophicus* Pal 5 FAPERJ; *Gluconacetobacter diazotrophicus* Pal 5 JGI; *Azospirillum* B510 uid46085; *Rhodospirillum rubrum* ATCC 11170; *Diaphorobacter* TPSY uid29975; *Verminephrobacter eiseniae* EF01-2; *Neisseria meningitides* 053442; *Neisseria meningitides* alpha14; *Neisseria meningitides* Z2491; *Desulfovibrio salexigens* DSM 2638; *Campylobacter jejuni* doylei 269 97; *Campylobacter jejuni* 81116; *Campylobacter jejuni*; *Campylobacter lari* RM2100; *Helicobacter hepaticus*; *Wolinella succinogenes*; *Tolumonas auensis* DSM 9187; *Pseudoalteromonas atlantica* T6c; *Shewanella pealeana* ATCC 700345; *Legionella pneumophila* Paris; *Actinobacillus succinogenes* 130Z; *Pasteurella multocida*; *Francisella tularensis novicida* U112; *Francisella tularensis holarctica*; *Francisella tularensis* FSC 198; *Francisella tularensis tularensis*; *Francisella tularensis* WY96-3418; and *Treponema denticola* ATCC 35405. Accordingly, aspects of the present disclosure are directed to a Cas9 protein present in a Type II CRISPR system.

The Cas9 protein may be referred by one of skill in the art in the literature as Csn1. The *S. pyogenes* Cas9 protein is shown below. See Deltcheva et al., Nature 471, 602-607 (2011) hereby incorporated by reference in its entirety.

(SEQ ID NO: 22)
MDKKYSIGLDIGTNSVGWAVITDEYKVPSKKFKVLGNTDRHSIKKNLIGA

LLFDSGETAEATRLKRTARRRYTRRKNRICYLQEIFSNEMAKVDDSFFHR

LEESFLVEEDKKHERHPIFGNIVDEVAYHEKYPTIYHLRKKLVDSTDKAD

LRLIYLALAHMIKFRGHFLIEGDLNPDNSDVDKLFIQLVQTYNQLFEENP

INASGVDAKAILSARLSKSRRLENLIAQLPGEKKNGLFGNLIALSLGLTP

NFKSNFDLAEDAKLQLSKDTYDDDLDNLLAQIGDQYADLFLAAKNLSDAI

LLSDILRVNTEITKAPLSASMIKRYDEHHQDLTLLKALVRQQLPEKYKEI

FFDQSKNGYAGYIDGGASQEEFYKFIKPILEKMDGTEELLVKLNREDLLR

KQRTFDNGSIPHQIHLGELHAILRRQEDFYPFLKDNREKIEKILTFRIPY

YVGPLARGNSRFAWMTRKSEETITPWNFEEVVDKGASAQSFIERMTNFDK

NLPNEKVLPKHSLLYEYFTVYNELTKVKYVTEGMRKPAFLSGEQKKAIVD

LLFKTNRKVTVKQLKEDYFKKIECFDSVEISGVEDRFNASLGTYHDLLKI

IKDKDFLDNEENEDILEDIVLTLTLFEDREMIEERLKTYAHLFDDKVMKQ

LKRRRYTGWGRLSRKLINGIRDKQSGKTILDFLKSDGFANRNFMQLIHDD

SLTFKEDIQKAQVSGQGDSLHEHIANLAGSPAIKKGILQTVKVVDELVKV

MGRHKPENIVIEMARENQTTQKGQKNSRERMKRIEEGIKELGSQILKEHP

VENTQLQNEKLYLYYLQNGRDMYVDQELDINRLSDYDVDHIVPQSFLKDD

SIDNKVLTRSDKNRGKSDNVPSEEVVKKMKNYWRQLLNAKLITQRKFDNL

TKAERGGLSELDKAGFIKRQLVETRQITKHVAQILDSRMNTKYDENDKLI

```
REVKVITLKSKLVSDFRKDFQFYKVREINNYHHAHDAYLNAVVGTALIKK

YPKLESEFVYGDYKVYDVRKMIAKSEQEIGKATAKYFFYSNIMNFFKTEI

TLANGEIRKRPLIETNGETGEIVWDKGRDFATVRKVLSMPQVNIVKKTEV

QTGGFSKESILPKRNSDKLIARKKDWDPKKYGGFDSPTVAYSVLVVAKVE

KGKSKKLKSVKELLGITIMERSSFEKNPIDFLEAKGYKEVKKDLIIKLPK

YSLFELENGRKRMLASAGELQKGNELALPSKYVNFLYLASHYEKLKGSPE

DNEQKQLFVEQHKHYLDEIIEQISEFSKRVILADANLDKVLSAYNKHRDK

PIREQAENIIHLFTLTNLGAPAAFKYFDTTIDRKRYTSTKEVLDATLIHQ

SITGLYETRIDLSQLGGD-.
```

According to one aspect, the RNA guided DNA binding protein includes homologs and orthologs of Cas9 which retain the ability of the protein to bind to the DNA, be guided by the RNA and cut the DNA. According to one aspect, the Cas9 protein includes the sequence as set forth for naturally occurring Cas9 from S. pyogenes and protein sequences having at least 30%, 40%, 50%, 60%, 70%, 80%, 90%, 95%, 98% or 99% homology thereto and being a DNA binding protein, such as an RNA guided DNA binding protein.

According to one aspect, an engineered Cas9-gRNA system is provided which enables RNA-guided genome cutting in a site specific manner in a stem cell, if desired, and modification of the stem cell genome by insertion of exogenous donor nucleic acids. The guide RNAs are complementary to target sites or target loci on the DNA. The guide RNAs can be crRNA-tracrRNA chimeras. The guide RNAs can be introduced from media surrounding the cell. In this manner a method of continuously modifying a cell is provided to the extent that various guide RNAs are provided to surrounding media and with the uptake by the cell of the guide RNAs and with supplementation of the media with additional guide RNAs. Supplementation may be in a continuous manner. The Cas9 binds at or near target genomic DNA. The one or more guide RNAs bind at or near target genomic DNA. The Cas9 cuts the target genomic DNA and exogenous donor DNA is inserted into the DNA at the cut site.

Accordingly, methods are directed to the use of a guide RNA with a Cas9 protein and an exogenous donor nucleic acid to multiplex insertions of exogenous donor nucleic acids into DNA within a stem cell expressing Cas9 by cycling the insertion of nucleic acid encoding the RNA (or providing RNA from the surrounding media) and exogenous donor nucleic acid, expressing the RNA (or uptaking the RNA), colocalizing the RNA, Cas9 and DNA in a manner to cut the DNA, and insertion of the exogenous donor nucleic acid. The method steps can be cycled in any desired number to result in any desired number of DNA modifications. Methods of the present disclosure are accordingly directed to editing target genes using the Cas9 proteins and guide RNAs described herein to provide multiplex genetic and epigenetic engineering of stem cells.

Further aspects of the present disclosure are directed to the use of DNA binding proteins or systems (such as the modified TALENS or Cas9 described herein) in general for the multiplex insertion of exogenous donor nucleic acids into the DNA, such as genomic DNA, of a stem cell, such as a human stem cell. One of skill in the art will readily identify exemplary DNA binding systems based on the present disclosure.

Cells according to the present disclosure unless otherwise specified include any cell into which foreign nucleic acids can be introduced and expressed as described herein. It is to be understood that the basic concepts of the present disclosure described herein are not limited by cell type. Cells according to the present disclosure include somatic cells, stem cells, eukaryotic cells, prokaryotic cells, animal cells, plant cells, fungal cells, archael cells, eubacterial cells and the like. Cells include eukaryotic cells such as yeast cells, plant cells, and animal cells. Particular cells include mammalian cells, such as human cells. Further, cells include any in which it would be beneficial or desirable to modify DNA.

Target nucleic acids include any nucleic acid sequence to which a TALEN or RNA guided DNA binding protein having nuclease activity as described herein can be useful to nick or cut. Target nucleic acids include any nucleic acid sequence to which a co-localization complex as described herein can be useful to nick or cut. Target nucleic acids include genes. For purposes of the present disclosure, DNA, such as double stranded DNA, can include the target nucleic acid and a co-localization complex can bind to or otherwise co-localize with the DNA or a TALEN can otherwise bind with the DNA at or adjacent or near the target nucleic acid and in a manner in which the co-localization complex or the TALEN may have a desired effect on the target nucleic acid. Such target nucleic acids can include endogenous (or naturally occurring) nucleic acids and exogenous (or foreign) nucleic acids. One of skill based on the present disclosure will readily be able to identify or design guide RNAs and Cas9 proteins which co-localize to a DNA or a TALEN which binds to a DNA, including a target nucleic acid. One of skill will further be able to identify transcriptional regulator proteins or domains, such as transcriptional activators or transcriptional repressors, which likewise co-localize to a DNA including a target nucleic acid. DNA includes genomic DNA, mitochondrial DNA, viral DNA or exogenous DNA. According to one aspect, materials and methods useful in the practice of the present disclosure include those described in Di Carlo, et al., Nucleic Acids Research, 2013, vol. 41, No. 7 4336-4343 hereby incorporated by reference in its entirety for all purposes including exemplary strains and media, plasmid construction, transformation of plasmids, electroporation of transcient gRNA cassette and donor nucleic acids, transformation of gRNA plasmid with donor DNA into Cas9-expressing cells, galactose induction of Cas9, identification of CRISPR-Cas targets in yeast genome, etc. Additional references including information, materials and methods useful to one of skill in carrying out the invention are provided in Mali, P., Yang, L., Esvelt, K. M., Aach, J., Guell, M., DiCarlo, J. E., Norville, J. E. and Church, G. M. (2013) RNA-Guided human genome engineering via Cas9. Science, 10.1126fscience.1232033; Storici, F., Durham, C. L., Gordenin, D. A. and Resnick, M. A. (2003) Chromosomal site-specific double-strand breaks are efficiently targeted for repair by oligonucleotides in yeast. PNAS, 100, 14994-14999 and Jinek, M., Chylinski, K., Fonfara, l., Hauer, M., Doudna, J. A. and Charpentier, E. (2012) A programmable dual-RNA-Guided DNA endonuclease in adaptive bacterial immunity Science, 337, 816-821 each of which are hereby incorporated by reference in their entireties for all purposes.

Foreign nucleic acids (i.e. those which are not part of a cell's natural nucleic acid composition) may be introduced into a cell using any method known to those skilled in the art for such introduction. Such methods include transfection, transduction, viral transduction, microinjection, lipofection, nucleofection, nanoparticle bombardment, transformation, conjugation and the like. One of skill in the art will readily understand and adapt such methods using readily identifiable literature sources.

Donor nucleic acids include any nucleic acid to be inserted into a nucleic acid sequence as described herein.

The following examples are set forth as being representative of the present disclosure. These examples are not to be construed as limiting the scope of the present disclosure as these and other equivalent embodiments will be apparent in view of the present disclosure, figures and accompanying claims.

EXAMPLE I

Guide RNA Assembly 19 bp of the selected target sequence (i.e. 5'-N19 of 5'-N19-NGG-3') were incorporated into two complementary 100mer oligonucleotides (TTCTTGGCTTTATATATCTT-GTGGAAAGGACGA-AACACCGN19GTTTTAGAGCTAGAA ATAGCAAGT-TAAAATAAGGCTAGTCC) (SEQ ID NO:23). Each 100mer oligonucleotide was suspended at 100 mM in water, mixed with equal volume and annealed in thermocycle machine (95° C., 5 min; Ramp to 4° C., 0.1° C./sec). To prepare the destination vector, the gRNA cloning vector (Addgene plasmid ID 41824) was linearized using AflIII and the vector was purified. The (10 ul) gRNA assembly reaction was carried out with 10 ng annealed 100 bp fragment, 100 ng destination backbone, 1× Gibson assembly reaction mix (New England Biolabs) at 50° C. for 30 min. The reaction can be processed directly for bacterial transformation to colonize individual assemblies.

EXAMPLE II

Re-coded TALEs Design and Assembly re-TALEs were optimized at different levels to facilitate assembly, and improve expression. re-TALE DNA sequences were first co-optimized for a human codon-usage, and low mRNA folding energy at the 5' end (GeneGA, Bioconductor). The obtained sequence was evolved through several cycles to eliminate repeats (direct or inverted) longer than 11 bp (See FIG. 12). In each cycle, synonymous sequences for each repeat are evaluated. Those with the largest hamming distance to the evolving DNA are selected. The sequence of one of re-TALE possessing 16.5 monomers as follows (SEQ ID NO: 24)
CTAACCCCTGAACAGGTAGTCGCTATAGCTTCAAATATCGGGGCAAGC

AAGCACTTGAGACCGTTCAACGACTCCTGCCAGTGCTCTGCCAAGCCCA

TGGATTGACTCCGGAGCAAGTCGTCGCGATCGCGAGCAACGGCGGGGGG

AAGCAGGCGCTGGAAACTGTTCAGAGACTGCTGCCTGTACTTTGTCAGG

CGCATGGTCTCACCCCCGAACAGGTTGTCGCAATAGCAAGTAATATAGG

CGGTAAGCAAGCCCTAGAGACTGTGCAACGCCTGCTCCCCGTGCTGTGT

CAGGCTCACGGTCTGACACCTGAACAAGTTGTCGCGATAGCCAGTCACG

ACGGGGGAAAACAAGCTCTAGAAACGGTTCAAAGGTTGTTGCCCGTTCT

GTGCCAAGCACATGGGTTAACACCCGAACAAGTAGTAGCGATAGCGTCA

AATAACGGGGGTAAACAGGCTTTGGAGACGGTACAGCGGTTATTGCCGG

TCCTCTGCCAGGCCCACGGACTTACGCCAGAACAGGTGGTTGCAATTGC

CTCCAACATCGGCGGGAAACAAGCGTTGGAAACTGTGCAGAGACTCCTT

CCTGTTTTGTGTCAAGCCCACGGCTTGACGCCTGAGCAGGTTGTGGCCA

TCGCTAGCCACGACGGAGGGAAGCAGGCTCTTGAAACCGTACAGCGACT

TCTCCCAGTTTTGTGCCAAGCTCACGGGCTAACCCCCGAGCAAGTAGTT

GCCATAGCAAGCAACGGAGGAGGAAAACAGGCATTAGAAACAGTTCAGC

GCTTGCTCCCGGTACTCTGTCAGGCACACGGTCTAACTCCGGAACAGGT

CGTAGCCATTGCTTCCCATGATGGCGGCAAACAGGCGCTAGAGACAGTC

CAGAGGCTCTTGCCTGTGTTATGCCAGGCACATGGCCTCACCCCGGAGC

AGGTCGTTGCCATCGCCAGTAATATCGGCGGAAAGCAAGCTCTCGAAAC

AGTACAACGGCTGTTGCCAGTCCTATGTCAAGCTCATGGACTGACGCCC

GAGCAGGTAGTGGCAATCGCATCTCACGATGGAGGTAAACAAGCACTCG

AGACTGTCCAAAGATTGTTACCCGTACTATGCCAAGCGCATGGTTTAAC

CCCAGAGCAAGTTGTGGCTATTGCATCTAACGGCGGTGGCAAACAAGCC

TTGGAGACAGTGCAACGATTACTGCCTGTCTTATGTCAGGCCCATGGCC

TTACTCCTGAGCAAGTCGTAGCTATCGCCAGCAACATAGGTGGGAAACA

GGCCCTGGAAACCGTACAACGTCTCCTCCCAGTACTTTGTCAAGCACAC

GGGTTGACACCGGAACAAGTGGTGGCGATTGCGTCCAACGGCGGAGGCA

AGCAGGCACTGGAGACCGTCCAACGGCTTCTTCCGGTTCTTTGCCAGGC

TCATGGGCTCACGCCAGAGCAGGTGGTAGCAATAGCGTCGAACATCGGT

GGTAAGCAAGCGCTTGAAACGGTCCAGCGTCTTCTGCCGGTGTTGTGCC

AGGCGCACGGACTCACACCAGAACAAGTGGTTGCTATTGCTAGTAACAA

CGGTGGAAAGCAGGCCCTCGAGACGGTGCAGAGGTTACTTCCCGTCCTC

TGTCAAGCGCACGGCCTCACTCCAGAGCAAGTGGTTGCGATCGCTTCAA

ACAATGGTGGAAGACCTGCCCTGGAA

According to certain aspects, TALEs may be used having at least 80% sequence identity, at least 85% sequence identity, at least 90% sequence identity, at least 95% sequence identity, at least 98% sequence identity, or at least 99% sequence identity to the above sequence. One of skill will readily understand where the above sequence may vary while still maintaining the DNA binding activity of the TALE.

re-TALE dimer blocks encoding two RVDs (see FIG. 6A) were generated by two rounds of PCR under standard Kapa HIFI (KPAP) PCR conditions, in which the first round of PCR introduced the RVD coding sequence and the second round of PCR generated the entire dimer blocks with 36 bp overlaps with the adjacent blocks. PCR products were purified using QIAquick 96 PCR Purification Kit (QIAGEN) and the concentrations were measured by Nano-drop. The primer and template sequences are listed in Table 1 and Table 2 below.

TABLE 1 re-TALE blocks sequences (SEQ ID NOs: 25-34)

| | |
|---|---|
| block0 | CGCAATGCGCTCACGGGAGCACCCCTCAACCTAACCCCTGA<br>ACAGGTAGTCGCTATAGCTTCANNNNNNGGGGGCAAGCAAG<br>CACTTGAGACCGTTCAACGACTCCTGCCAGTGCTCTGCCAA<br>GCCCATGGATTGACTCCGGAGCAAGTCGTCGCGATCGCGAG<br>CNNNNNNGGGGGAAGCAGGCGCTGGAAACTGTTCAGAGAC<br>TGCTGCCTGTACTTTGTCAGGCGCATGGTCTC |
| block1 | AGACTGCTGCCTGTACTTTGTCAGGCGCATGGTCTCACCCC<br>CGAACAGGTTGTCGCAATAGCAAGTNNNNNNGGCGGTAAGC<br>AAGCCCTAGAGACTGTGCAACGCCTGCTCCCCGTGCTGTGT<br>CAGGCTCACGGTCTGACACCTGAACAAGTTGTCGCGATAGC<br>CAGTNNNNNNGGGGGAAAACAAGCTCTAGAAACGGTTCAAA<br>GGTTGTTGCCCGTTCTGTGCCAAGCACATGGGTTA |
| block1' | TGCGCTCACGGGAGCACCCCTCAACCTCACCCCCGAACAGG<br>TTGTCGCAATAGCAAGTNNNNNNGGCGGTAAGCAAGCCCTA<br>GAGACTGTGCAACGCCTGCTCCCCGTGCTGTGTCAGGCTCA<br>CGGTCTGACACCTGAACAAGTTGTCGCGATAGCCAGTNNNN<br>NNGGGGGAAAACAAGCTCTAGAAACGGTTCAAAGGTTGTTG<br>CCCGTTCTGTGCCAAGCACATGGGTTA |
| block2 | AGGTTGTTGCCCGTTCTGTGCCAAGCACATGGGTTAACACC<br>CGAACAAGTAGTAGCGATAGCGTCANNNNNNGGGGGTAAAC<br>AGGCTTTGGAGACGGTACAGCGGTTATTGCCGGTCCTCTGC<br>CAGGCCCACGGACTTACGCCAGAACAGGTGGTTGCAATTGC<br>CTCCNNNNNNGGCGGGAAACAAGCGTTGGAAACTGTGCAGA<br>GACTCCTTCCTGTTTTGTGTCAAGCCCACGGCTTGACGCCT |
| block3 | AGACTCCTTCCTGTTTTGTGTCAAGCCCACGGCTTGACGCC<br>TGAGCAGGTTGTGGCCATCGCTAGCNNNNNNGGAGGGAAGC<br>AGGCTCTTGAAACCGTACAGCGACTTCTCCCAGTTTTGTGC<br>CAAGCTCACGGGCTAACCCCCGAGCAAGTAGTTGCCATAGC<br>AAGCNNNNNNGGAGGAAAACAGGCATTAGAAACAGTTCAGC<br>GCTTGCTCCCGGTACTCTGTCAGGCACACGGTCTA |
| block4 | CGCTTGCTCCCGGTACTCTGTCAGGCACACGGTCTAACTCC<br>GGAACAGGTCGTAGCCATTGCTTCCNNNNNNGGCGGCAAAC<br>AGGCGCTAGAGACCGTCCAGAGGCTCTTGCCTGTGTTATGC<br>CAGGCACATGGCCTCACCCCGGAGCAGGTCGTTGCCATCGC<br>CAGTNNNNNNGGCGGAAAGCAAGCTCTCGAAACAGTACAAC<br>GGCTGTTGCCAGTCCTATGTCAAGCTCATGGACTG |
| block5 | CGGCTGTTGCCAGTCCTATGTCAAGCTCATGGACTGACGCC<br>CGAGCAGGTAGTGGCAATCGCATCTNNNNNNGGAGGTAAAC<br>AAGCACTCGAGACTGTCCAAAGATTGTTACCCGTACTATGC<br>CAAGCGCATGGTTTAACCCCAGAGCAAGTTGTGGCTATTGC<br>ATCTNNNNNNGGTGGCAAACAAGCCTTGGAGACCGTGCAAC<br>GATTACTGCCTGTCTTATGTCAGGCCCATGGCCTT |
| block6 | CGATTACTGCCTGTCTTATGTCAGGCCCATGGCCTTACTCC<br>TGAGCAGGTGGTCGCTATCGCCAGCNNNNNNGGGGGCAAGC<br>AAGCACTGGAAACAGTCCAGCGTTTGCTTCCAGTACTTTGT<br>CAGGCGCATGGATTGACACCGGAACAAGTGGTGGCTATAGC<br>CTCANNNNNNGGAGGAAAGCAGGCGCTGGAAACCGTCCAAC<br>GTCTTTTACCGGTGCTTTGCCAGGCGCACGGGCTC |
| block6' | CGATTACTGCCTGTCTTATGTCAGGCCCATGGCCTTACTCC<br>TGAGCAAGTCGTAGCTATCGCCAGCNNNNNNGGTGGGAAAC<br>AGGCCCTGGAAACCGTACAACGTCTCCTCCCAGTACTTTGT<br>CAAGCACACGGGTTGACACCGGAACAAGTGGTGGCGATTGC<br>GTCCNNNNNNGGAGGCAAGCAGGCACTGGAGACCGTCCAAC<br>GGCTTCTTCCGGTTCTTTGCCAGGCTCATGGGCTC |
| block7 | CGGCTTCTTCCGGTTCTTTGCCAGGCTCATGGGCTCACGCC<br>AGAGCAGGTGGTAGCAATAGCGTCGNNNNNNGGTGGTAAGC<br>AAGCGCTTGAAACGGTCCAGCGTCTTCTGCCGGTGTTGTGC<br>CAGGCGCACGGACTCACACCAGAACAGGTGGTTGCTATTGC<br>TAGTNNNNNNGGTGGAAAGCAGGCCCTCGAGACGGTGCAGA<br>GGTTACTTCCCGTCCTCTGTCAAGCGCACGGCCTC |

TABLE 2 re-TALE blocks primer sequences (SEQ ID NOs: 35-53)

| | |
|---|---|
| block0-F | CGCAATGCGCTCACGGGAGCACCCCTCAACctAACCCC<br>TGAACAGGT*A*G |
| block0-R | GAGACCATGCGCCTGACAAAGTACAGGCAGCAGTCTCT<br>GAACAG*T*T |
| block1'-F | TGGCGCAATGCGCTCACGGGAGCACCCCTCA*A*C |
| block1-F | AGACTGCTGCCTGTACTTTGTCAGGCGCATGGTCTCAC<br>CCCCGAACA*G*G |
| block1-R/block1'-R | TAACCCATGTGCTTGGCACAGAACGGGCAACAACCTTT<br>GAACCG*T*T |
| block2-F | AGGTTGTTGCCCGTTCTGTGCCAAGCACATGGGTTAAC<br>ACCCgaac*a*a |
| block2-R | AGGCGTCAAGCCGTGGGCTTGACACAAAACAGGAAGGA<br>GTCTCTGCACAG*T*t |
| block3-F | AGACTCCTTCCTGTTTTGTGTCAAGCCCACGGCTTGAC<br>GCCTG*A*G |
| block3-R | TAGACCGTGTGCCTGACAGAGTACCGGGAGCAAGCGCT<br>*G*A |
| block4-F | CGCTTGCTCCCGGTACTCTGTCAGGCACACGGTCTAA*<br>C*T |
| block4-R | CAGTCCATGAGCTTGACATAGGACTGGCAACAGCCGTT<br>*G*T |
| block5-F | CGGCTGTTGCCAGTCCTATGTCAAGCTCATGGACTGA*<br>C*G |
| block5-R | AAGGCCATGGGCCTGACATAAGACAGGCAGTAATCGTT<br>*G*C |
| block6-F | CGATTACTGCCTGTCTTATGTCAGGCCCATGGCCTTA*<br>C*T |
| block6-R | GAGCCCGTGCGCCTGGCAAAGCACCGGTAAAAGACGTT<br>GGA*C*G |
| block6'-F | CGATTACTGCCTGTCTTATGTCAGGCCCATGGCCTTAC<br>TCCTGAGCAA*G*T |
| block6'-R | GAGCCCATGAGCCTGGCAAAGAACCGGAAGAAGCCGTT<br>*G*G |
| block7-F | CGGCTTCTTCCGGTTCTTTGCCAGGCTCATGGGCTCAC<br>GCCAGAGCAGG*T*G |
| block7-R | GAGGCCGTGCGCTTGACAGAGGACGGGAAGTAACCTCT<br>*G*C | re-TALENs and re-TALE-TF destination vectors were constructed by modifying the TALE-TF and TALEN cloning backbones (see reference 24 hereby incorporated by reference in its entirety). The 0.5 RVD regions on the vectors were re-coded and SapI cutting site was incorporated at the designated re-TALE cloning site. The sequences of re-TALENs and re-TALE-TF backbones are provided in FIG. 20. Plasmids can be pre-treated with SapI (New England Biolabs) with manufacturer recommended conditions and purified with QIAquick PCR purification kit (QIAGEN).

A (10 ul) one-pot TASA assembly reaction was carried out with 200 ng of each block, 500 ng destination backbone, 1×TASA enzyme mixture (2 U SapI, 100 U Ampligase (Epicentre), 10 mU T5 exonuclease (Epicentre), 2.5 U Phusion DNA polymerase (New England Biolabs)) and 1× isothermal assembly reaction buffer as described before (see reference 25 hereby incorporated by reference in its entirety) (5% PEG-8000, 100 mM Tris-HCl pH 7.5, 10 mM MgCl2, 10 mM DTT, 0.2 mM each of the four dNTPs and 1 mM NAD). Incubations were performed at 37° C. for 5 min and 50° C. for 30 min TASA assembly reaction can be processed directly for bacterial transformation to colonize individual assemblies. The efficiency of obtaining full length construct is ~20% with this approach. Alternatively, >90% efficiency can be achieved by a three-step assembly. First, 10 ul re-TALE assembly reactions are performed with 200 ng of each block, 1× re-TALE enzyme mixture (100 U Ampligase, 12.5 mU T5 exonuclease, 2.5 U Phusion DNA polymerase) and 1× isothermal assembly buffer at 50° C. for 30 min, followed by standardized Kapa HIFI PCR reaction, agarose gel electrophoresis, and QIAquick Gel extraction (Qiagen) to enrich the full length re-TALEs. 200 ng re-TALE amplicons can then be mixed with 500 ng Sap1-pre-treated destination backbone, 1× re-TALE assembly mixture and 1× isothermal assembly reaction buffer and incubated at 50° C. for 30 min. The re-TALE final assembly reaction can be processed directly for bacterial transformation to colonize individual assemblies. One of skill in the art will readily be able to select endonucleases, exonucleases, polymerases and ligases from among those known to practice the methods described herein. For example, type II endonucleases can be used, such as: Fok 1, Bts I, Ear I, Sap I. Exonucleases which are titralable can be used, such as lamda exonuclease, T5 exonuclease and Exonuclease III. Non-hotstart polymerases can be used, such as phusion DNA polymerase, Taq DNA polymerase and VentR DNA polymerase. Thermostable ligases can be used in this reaction, such as Ampligase, pfu DNA ligase, Taq DNA ligase. In addition, different reaction conditions can be used to activate such endonucleases, exonucleases, polymerases and ligases depending on the particular species used.

EXAMPLE III

Cell Line and Cell Culture

PGP1 iPS cells were maintained on Matrigel (BD Biosciences)-coated plates in mTeSR1 (Stemcell Technologies). Cultures were passaged every 5-7 days with TrypLE Express (Invitrogen). 293T and 293FT cells were grown and maintained in Dulbecco's modified Eagle's medium (DMEM, Invitrogen) high glucose supplemented with 10% fetal bovine serum (FBS, Invitrogen), penicillin/streptomycin (pen/strep, Invitrogen), and non-essential amino acids (NEAA, Invitrogen). K562 cells were grown and maintained in RPMI (Invitrogen) supplemented with 10% fetal bovine serum (FBS, Invitrogen 15%) and penicillin/streptomycin (pen/strep, Invitrogen). All cells were maintained at 37° C. and 5% CO2 in a humidified incubator.

A stable 293T cell line for detecting HDR efficiency was established as described in reference 26 hereby incorporated by reference in its entirety. Specifically, the reporter cell lines bear genomically integrated GFP coding sequences disrupted by the insertion of a stop codon and a 68 bp genomic fragment derived from the AAVS1 locus.

EXAMPLE IV

Test of re-TALENs Activity 293T reporter cells were seeded at densities of 2×105 cells per well in 24-well plate and transfected them with 1 μg of each re-TALENs plasmid and 2 μg DNA donor plasmid using Lipofectamine 2000 following the manufacturer's protocols. Cells were harvested using TrypLE Express (Invitrogen) ~18 h after transfection and resuspended in 200 μl of media for flow cytometry analysis using an LSRFortessa cell analyzer (BD Biosciences). The flow cytometry data were analyzed using FlowJo (FlowJo). At least 25,000 events were analyzed for each transfection sample. For endogenous AAVS1 locus targeting experiment in 293T, the transfection procedures were identical as described above and puromycin selection was conducted with drug concentration at 3 μg/ml 1 week after transfection.

EXAMPLE V

Functional Lentivirus Generation Assessment

The lentiviral vectors were created by standard PCR and cloning techniques. The lentiviral plasmids were transfected by Lipofectamine 2000 with Lentiviral Packaging Mix (Invitrogen) into cultured 293FT cells (Invitrogen) to produce lentivirus. Supernatant was collected 48 and 72 h post-transfection, sterile filtered, and 100 ul filtered supernatant was added to 5×105 fresh 293T cells with polybrene. Lentivirus titration was calculated based on the following formula: virus titration=(percentage of GFP+293T cell*initial cell numbers under transduction)/(the volume of original virus collecting supernatant used in the transduction experiment). To test the functionality of lentivirus, 3 days after transduction, lentivirus transduced 293T cells were transfected with 30 ng plasmids carrying mCherry reporter and 500 ng pUC19 plasmids using Lipofectamine 2000 (Invitrogen). Cell images were analyzed using Axio Observer Z.1 (Zeiss) 18 hours after transfection and harvested using TrypLE Express (Invitrogen) and resuspended in 200 μl of media for flow cytometry analysis using a LSRFortessa cell analyzer (BD Biosciences). The flow cytometry data were analyzed using BD FACSDiva (BD Biosciences).

EXAMPLE VI

Test of re-TALENs and Cas9-gRNA Genome Editing Efficiency

PGP1 iPSCs were cultured in Rho kinase (ROCK) inhibitor Y-27632 (Calbiochem) 2 h before nucleofection. Transfections were done using P3 Primary Cell 4D-Nucleofector X Kit (Lonza). Specifically, cells were harvested using TrypLE Express (Invitrogen) and 2×106 cells were resuspended in 20 μl nucleofection mixture containing 16.4 μl P3 Nucleofector solution, 3.6 μl supplement, 1 μg of each re-TALENs plasmid or 1 ug Cas9 and 1 ug gRNA construct, 2 μl of 100 μM ssODN. Subsequently, the mixtures were transferred to 20 μl Nucleocuvette strips and nucleofection was conducted using CB150 program. Cells were plated on Matrigel-coated plates in mTeSR1 medium supplemented with ROCK inhibitor for the first 24 hrs. For endogenous AAVS1 locus targeting experiment with dsDNA donor, the same procedure was followed except 2 μg dsDNA donor was used and the mTeSR1 media was supplemented with puromycin at the concentration of 0.5 ug/mL 1 week after transfection.

The information of reTALENs, gRNA and ssODNs used in this example are listed in Table 3 and Table 4 below.

TABLE 3

Information of re-TALEN pairs/Cas9-gRNA targeting CCR5 (SEQ ID NOs: 54-160)

| # targeting site | re-TALENs pair targeting site start /chr3: | re-TALENs pair targeting site (end) /chr3: | re-TALEN-L targeting sequence | re-TALEN-R targeting sequence | gRNA targeting sequence | gRAN targeting sequence (start) position |
|---|---|---|---|---|---|---|
| 1 | 46409942 | 46409993 | TCCCCACTTTCTTGTGAA | TAACCACTCAGGACAGGG | CACTTTCTTGTGAATCCTT | 46409946 |
| 2 | 46410227 | 46410278 | TCACACAGCAAGTCAGCA | TAGCGGAGCAGGCTCGGA | TGGGCTAGCGGAGCAGGCT | 46410264 |
| 3 | 46411260 | 46411311 | TACCCAGACGAGAAAGCT | TCAGACTGCCAAGCTTGA | ACCCAGACGAGAAAGCTGA | 46411261 |
| 4 | 46411464 | 46411515 | TCTTGTGGCTCGGGAGTA | TATTGTCAGCAGAGCTGA | AGAGGGCATCTTGTGGCTC | 46411456 |
| 5 | 46411517 | 46411568 | TTGAGATTTTCAGATGTC | TATACAGTCATATCAAGC | ATCAAGCTCTCTTGGCGGT | 46411538 |
| 6 | 46411634 | 46411685 | TTCAGATAGATTATATCT | TGCCAGATACATAGGTGG | GCTTCAGATAGATTATATC | 46411632 |
| 7 | 46412396 | 46412447 | TTATACTGTCTATATGAT | TCAGCTCTTCTGGCCAGA | ACGGATGTCTCAGCTCTTC | 46412437 |
| 8 | 46412432 | 46412483 | TGGCCAGAAGAGCTGAGA | TTACCGGGGAGAGTTTCT | CCGGGGAGAGTTTCTTGTA | 46412461 |
| 9 | 46412750 | 46412801 | TTTGCAGAGAGATGAGTC | TTAGCAGAAGATAAGATT | GAAATCTTATCTTCTGCTA | 46412782 |
| 10 | 46413152 | 46413203 | TATAAGACTAAACTACCC | TCGTCTGCCACCACAGAT | AATGCATGACATTCATCTG | 46413172 |
| 11 | 46414305 | 46414356 | TAAAACAGTTTGCATTCA | TATAAAGTCCTAGAATGT | AACAGTTTGCATTCATGGA | 46414308 |
| 12 | 46414608 | 46414659 | TGGCCATCTCTGACCTGT | TAGTGAGCCCAGAAGGGG | CCAGAAGGGGACAGTAAGA | 46414632 |
| 13 | 46414768 | 46414820 | TAGGTACCTGGCTGTCGT | TGACCGTCCTGGCTTTTA | CTGACAATCGATAGGTACC | 46414757 |
| 14 | 46415017 | 46415068 | TGTCATGGTCACTGCTA | TCGACACCGAAGCAGAGT | ACACCGAAGCAGAGTTTTT | 46415046 |
| 15 | 46420034 | 46420084 | TGCCCCCGCGAGGCCACA | TCTGGAAGTTGAACACCC | GGAAGTTGAACACCCTTGC | 46420062 |

TABLE 4 ssODN design for studying ssODN-mediated genome editing

Figure 3A:
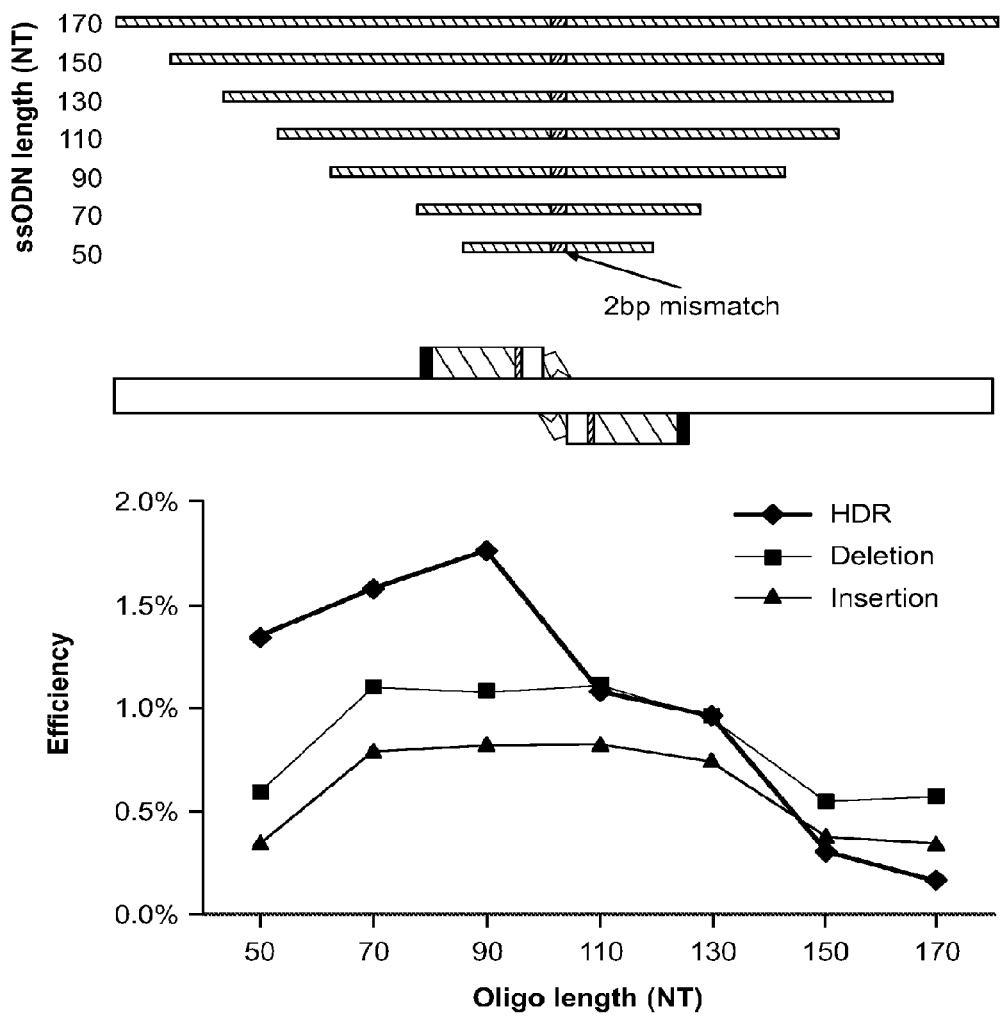
Figure 3B:
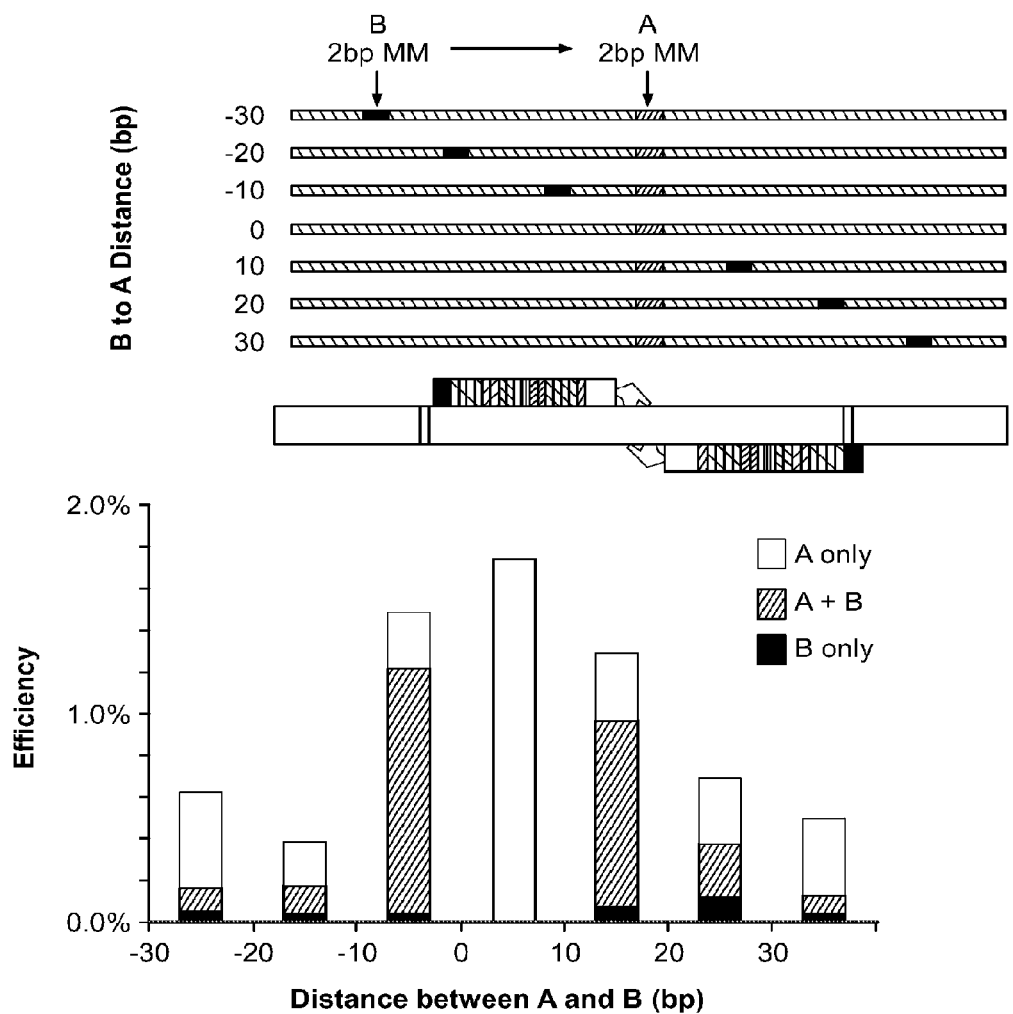

| | | |
|---|---|---|
| FIG. 3b Distance between the secondary mutation and DSB | 90-*1 | CTACTGTCATTCAGGGCAATACCCAGACGAGAAAGCTGAGGGTATAACAGGTTTCAAGCTTGGCAGTCTGACTACAGAGGCCACTGGCTT |
| | 90-*2 | CTACTGTCATTCAGCCCAATACCCTAACGAGAAAGCTGAGGGTATAACAGGTTTCAAGCTTGGCAGTCTGACTACAGAGGCCACTGGCTT |
| | 90-*3 | CTACTGTCATTCAGCCCAATACCCAGACGAGAAAGTGAGGGTATAACAGGTTTCAAGCTTGGCAGTCTGACTACAGAGGCCACTGGCTT |
| | 90M-0 | CTACTGTCATTCAGCCCAATACCCAGACGAGAAAGCTGAGGGTATAACAGGTTTCAAGCTTGGCAGTCTGACTACAGAGGCCACTGGCTT |
| | 90-*4 | CTACTGTCATTCAGCCCAATACCCAGACGAGAAAGCTGAGGGTATAACAGGTTTGTAGCTTGGCAGTCTGACTACAGAGGCCACTGGCTT |
| | 90-*5 | CTACTGTCATTCAGCCCAATACCCAGACGAGAAAGCTGAGGGTATAACAGGTTTCAAGCTTGGCTCTCTGACTACAGAGGCCACTGGCTT |
| | 90-*6 | CTACTGTCATTCAGCCCAATACCCAGACGAGAAAGCTGAGGGTATAACAGGTTTCAAGCTTGGCAGTCTGACTAGTGAGGCCACTGGCTT |

TABLE 4-continued ssODN design for studying ssODN-mediated genome editing

Figure 2C:
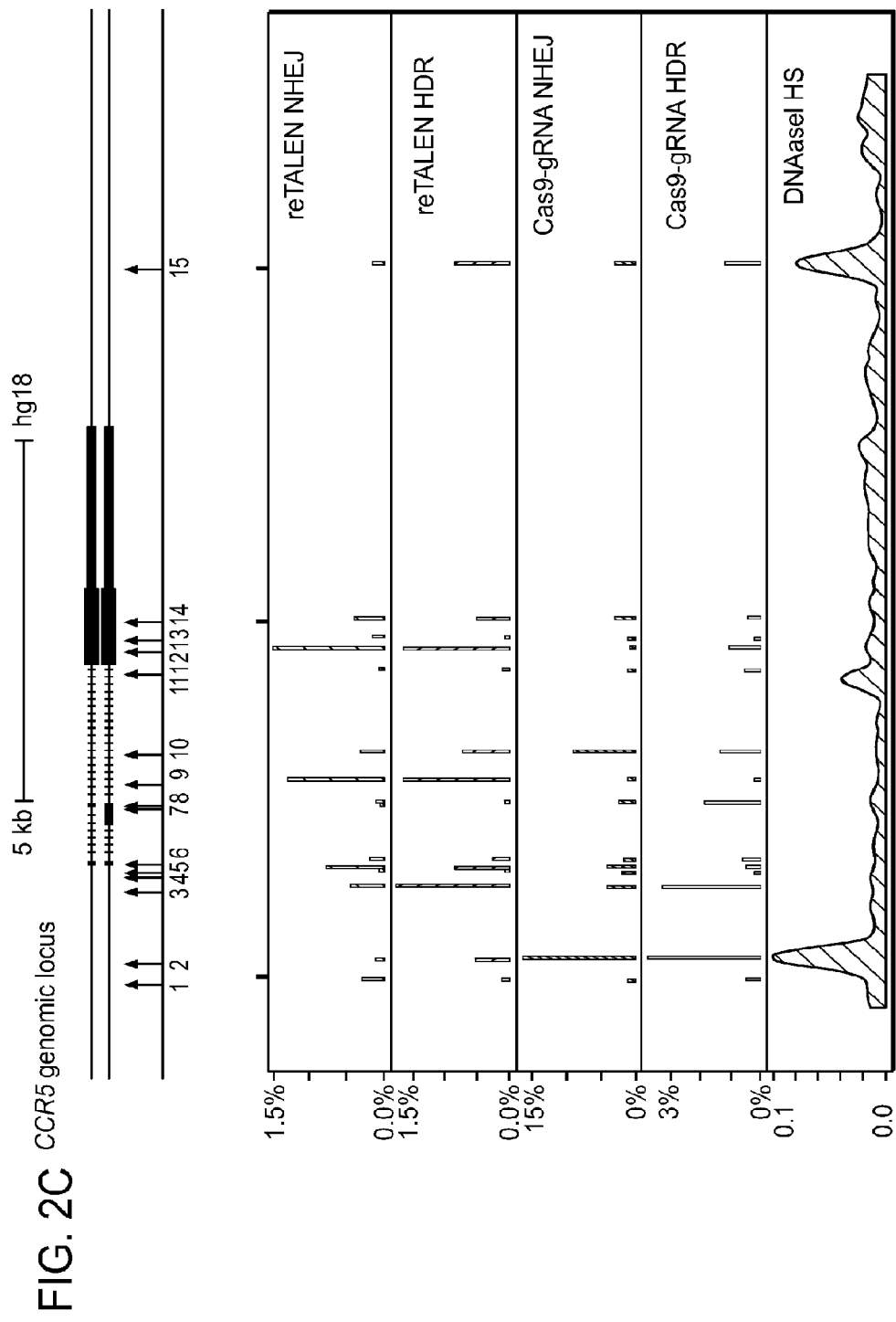
Figure 3C:
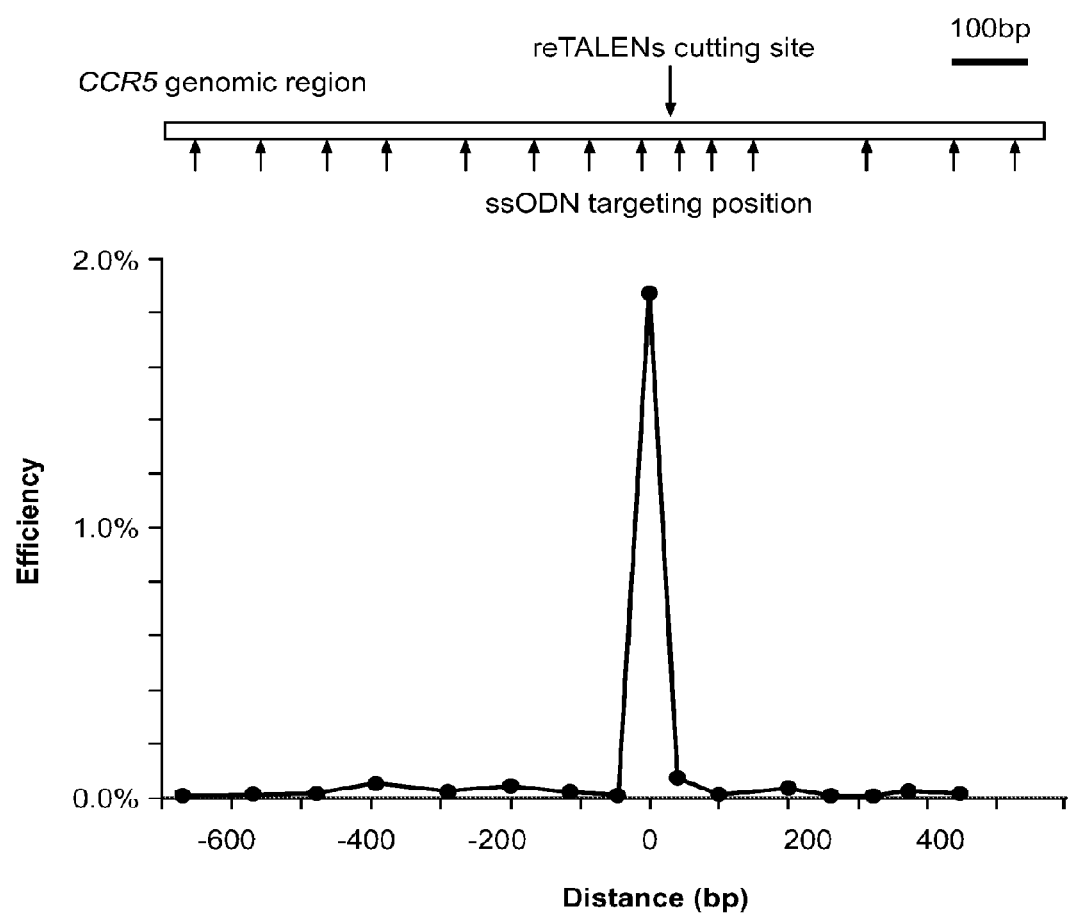
Figure 3D:
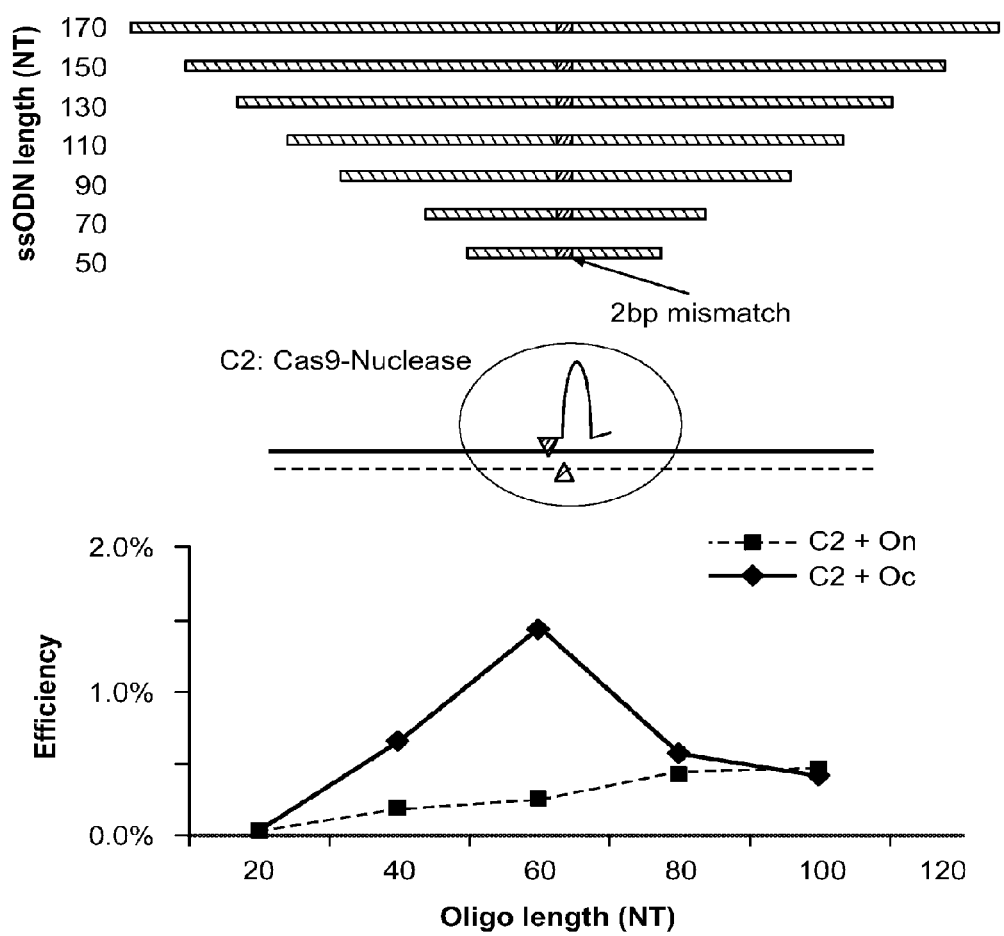

| | | | |
|---|---|---|---|
| FIG. 3c | distance between ssODN and the DSB | L670 bp_90M | CACTTTATATTTCCCTGCTTAAACAGTCCCCCGAGGGTGGGTGCGGA |
| | | L570 bp_90M | AAAGGCTCTACACTTGTTATCATTCCCTCTCCACCACAGGCAT |
| | | | TTTGTATTTGGGTTTTTTTAAAAACCTCCACTCTACAGTTAAGAATTCT |
| | | L480 bp_90M | AAGGCACAGAGCTTCAATAATTTGGTCAGAGCCAAGTAGCAG |
| | | | GGAGGTTAAACCCAGCAGCATGACTGCAGTTCTTAATCAATGCCCCT |
| | | L394 bp_90M | TGAATTGCACATATGGGATGAACTAGAACATTTTCTCGATGAT |
| | | | CTCGATGATTCGCTGTCCTTGTTATGATTATGTTACTGAGCTCTACTG |
| | | L290 bp_90M | TAGCACAGACATATGTCCCTATATGGGGCGGGGGTGGGGGTG |
| | | | GGTGTCTTGATCGCTGGGCTATTTCTATACTGTTCTGGCTTTTCGGAA |
| | | L200 bp_90M | GCAGTCATTTCTTTCTATTCTCCAAGCACCAGCAATTAGCTT |
| | | | GCTTCTAGTTTGCTGAAACTAATCTGCTATAGACAGAGACTCCGACG |
| | | L114 bp_90M | AACCAATTTTATTAGGATTTGATCAAATAAACTCTCTCTGACA |
| | | | GAAAGAGTAACTAAGAGTTTGATGTTTACTGAGTGCATAGTATGCAC |
| | | L45b p_90M | TAGATGCTGGCCGTGGATGCCTCATAGAATCCTCCCAACAACT |
| | | | GCTAGATGCTGGCCGTGGATGCCTCATAGAATCCTCCCAACAACCGA |
| | | R40b p_90M | TGAAATGACTACTGTCATTCAGCCCAATACCCAGACGAGAAAG |
| | | | ACAGGTTTCAAGCTTGGCAGTCTGACTACAGAGGCCACTGGCTTTAC |
| | | R100 bp_90M | CCCTGGGTTAGTCTGCCTCTGTAGGATTGGGGGCACGTAATTT |
| | | | TTAGTCTGCCTCTGTAGGATTGGGGGCACGTAATTTTGCTGTTTAAG |
| | | R200 bp_90M | GTCTCATTTGCCTTCTTAGAGATCACAAGCCAAAGCTTTTTAT |
| | | | GGAAGCCCAGAGGGCATCTTGTGGCTCGGGAGTAGCTCTCTGCTACC |
| | | R261 bp_90M | TTCTCAGCTCTGCTGACAATACTTGAGATTTTCAGATGTCACC |
| | | | TCAGCTCTGCTGACAATACTTGAGATTTTCAGATGTCACCAACCAGC |
| | | R322 bp_90M | AAGAGAGCTTGATATGACTGTATATAGTATAGTCATAAAGAAC |
| | | | CATAAAGAACCTGAACTTGACCATATACTTATGTCATGTGGAAATCT |
| | | R375 M_90M | TCTCATAGCTTCAGATAGATTATATCTGGAGTGAAGAATCCTG |
| | | | GTGGAAAATTTCTCATAGCTTCAGATAGATTATATCTGGAGTGAGCA |
| | | R448 bp_90M | ATCCTGCCACCTATGTATCTGGCATAGTGTGAGTCCTCATAAA |
| | | | GGTTTGAAGGGCAACAAAATAGTGAACAGAGTGAAAATCCCCACCT |
| | | Complement-30mer | AGATCCTGGGTCCAGAAAAGATGGGAAACCTGTTTAGCTCACC |
| | | | GGCCACTAGGGACAAAATTGGTGAcagaaa |
| FIG. 3d | ssODN length orientation and for Cas9-gRNA targeting | Complement-50mer | CCCACAGTGGGGCCACTAGGGACAAAATTGGTGAcagaaaagccccatcc |
| | | Complement-70mer | TCCCCTCCACCCCACAGTGGGGCCACTAGGGACAAAATTGGTGAcaga aaagccccatccttaggcctcc |
| | | Complement-90mer | cttTTATCTGTCCCCTCCACCCCACAGTGGGGCCACTAGGGACAAAATT GGTGAcagaaaagccccatccttaggcctcctccttcctag |
| | | Complement-110mer | gttctgggtactttTTATCTGTCCCCTCCACCCCACAGTGGGCCACTAGGGAC AAAATTGGTGAcagaaaagccccatccttaggcctcctccttcctagtctcctgata |
| | | Non-complement-30mer | TTTCTGTCACCAATGGTGTCCCTAGTGGCC |
| | | Non-complement-50mer | GGATGGGGCTTTTCTGTCACCAATGGTGTCCCTAGTGGCCCCACTGT GGG |
| | | Non-complement-70mer | GGAGGCCTAAGGATGGGGCTTTTCTGTCACCAATGGTGTCCCTAGTG GCCCCACTGTGGGGTGGAGGGGA |
| | | Non-complement-90mer | CTAGGAAGGAGGAGGCCTAAGGATGGGCTTTTCTGTCACCAATGG TGTCCCTAGTGGCCCCACTGTGGGGTGGAGGGGACAGATAAAAG |
| | | Non-complement-110mer | TATCAGGAGACTAGGAAGGAGGAGGCCTAAGGATGGGGCTTTTCTG TCACCAATGGTGTCCCTAGTGGCCCCACTGTGGGGTGGAGGGGACA GATAAAAGTACCCAGAAC |
| FIG. 2c | ssODN donor for Cas9-gRNA targeting CCR5 | Cas9-gRNA-CCR5-1 | TTCTAGTAACCACTCAGGACAGGGGGGTTCAGCCCAAAAATTCACA AGAAAGTGGGGACCCATGGGAAAT |
| | | Cas9-gRNA-CCR5-2 | CAGCAAGTCAGCAGCACAGCGTGTGTGACTCCGAGGGTGCTCCGCT AGCCCACATTGCCCTCTGGGGGTG |
| | | Cas9-gRNA-CCR5-3 | GTCAGACTGCCAAGCTTGAAACCTGTCTTACCCTCTACTTTCTCGTCT GGGTATTGGGCTGAATGACAGT |
| | | Cas9-gRNA-CCR5-4 | CAGAGCTGAGAAGACAGACAGAGAGCTACTCCCGAAGCACAAGATGC CCTCTGGGCTTCCGTGACCTTGGC |
| | | Cas9-gRNA-CCR5-5 | CTGACAATACTTGAGATTTTCAGATGTCACCAACGACCAAGAGAGCT TGATATGACTGTATATAGTATAG |
| | | Cas9-gRNA-CCR5-6 | CAGATACATAGGTGGCAGGATTCTTCACTCCAGACTTAATCTATCTG AAGCTATGAGAAATTTTCCACAT |
| | | Cas9-gRNA-CCR5-7 | TATATGATTGATTTGCACAGCTCATCTGGCCAGATAAGCTGAGACAT CCGTTCCCCTACAAGAAACTCTC |
| | | Cas9-gRNA-CCR5-8 | ATCTGGCCAGAAGAGCTGAGACATCCGTTCCCCTTGAAGAAACTCTC CCCGGTAAGTAACCTCTCAGCTG |
| | | Cas9-gRNA-CCR5-9 | AGGCATCTCACTGGAGAGGGTTTAGTTCTCCTTAAGAGAAGATAAGA TTTCAAGAGGGAAGCTAAGACTC |
| | | Cas9-gRNA-CCR5-10 | ATAATATAATAAAAAATGTTCGTCTGCCACCACTAATGAATGTCAT GCATTCTGGGTAGTTTAGTCTTA |

TABLE 4-continued ssODN design for studying ssODN-mediated genome editing

| | | |
|---|---|---|
| | Cas9-gRNA-CCR5-11 | TTTATAAAGTCCTAGAATGTATTTAGTTGCCCTCGTTGAATGCAAACT GTTTTATACATCAATAGGTTTT |
| | Cas9-gRNA-CCR5-12 | GCTCAACCTGGCCATCTCTGACCTGTTTTTCCTTCCCACTGTCCCCTT CTGGGCTCACTATGCTGCCGCC |
| | Cas9-gRNA-CCR5-13 | TTTTAAAGCAAACACAGCATGGACGACAGCCAGGCTCCTATCGATTG TCAGGAGGATGATGAAGAAGATT |
| | Cas9-gRNA-CCR5-14 | GCTTGTCATGGTCATCTGCTACTCGGGAATCCTAATTACTCTGCTTCG GTGTCGAAATGAGAAGAAGAGG |
| | Cas9-gRNA-CCR5-15 | ATACTGCCCCCGCGAGGCCACATTGGCAAACCAGCTTGGGTGTTCAA CTTCCAGACTTGGCCATGGAGAA |
| ssODN donor for reTALENs targeting CCR5 | reTALEN-CCR5-1 | CTGAAGAATTTCCCATGGGTCCCCACTTTCTTGTGAATCCTTGGAGTG AACCCCCCTGTCCTGAGTGGTTACTAGAACACACCTCTGGAC |
| | reTALEN-CCR5-2 | TGGAAGTATCTTGCCGAGGTCACACAGCAAGTCAGCAGCACAGCCA GTGTGACTCCGAGCCTGCTCCGCTAGCCCACATTGCCCTCTGGG |
| | reTALEN-CCR5-3 | CTACTGTCATTCAGCCCAATACCCAGACGAGAAAGCTGAGGGTATA ACAGGTTTCAAGCTTGGCAGTCTGACTACAGAGGCCACTGGCTT |
| | reTALEN-CCR5-4 | GGAAGCCCAGAGGGCATCTTGTGGCTCGGGAGTAGCTCTCTGCTACC TTCTCAGCTCTGCTGACAATACTTGAGATTTTCAGATGTCACC |
| | reTALEN-CCR5-5 | TCAGCTCTGCTGACAATACTTGAGATTTTCAGATGTCACCAACGCCC AAGAGAGCTTGATATGACTGTATATAGTATAGTCATAAAGAAC |
| | reTALEN-CCR5-6 | GTGGAAAATTTCTCATAGCTTCAGATAGATTATATCTGGAGTGAGCA ATCCTGCCACCTATGTATCTGGCATAGTGTGAGTCCTCATAAA |
| | reTALEN-CCR5-7 | GAAACAGCATTTCCTACTTTTATACTGTCTATATGATTGATTTGGTCA GCTCATCTGGCCAGAAGAGCTGAGACATCCGTTCCCCTACAA |
| | reTALEN-CCR5-8 | TTGATTTGCACAGCTCATCTGGCCAGAAGAGCTGAGACATCCGTATC CCTACAAGAAACTCTCCCCGGTAAGTAACCTCTCAGCTGCTTG |
| | reTALEN-CCR5-9 | GGAGAGGGTTTAGTTCTCCTTAGCAGAAGATAAGATTTCAAGATGAG AGCTAAGACTCATCTCTCTGCAAATCTTTCTTTTGAGAGGTAA |
| | reTALEN-CCR5-10 | TAATATAATAAAAAATGTTTCGTCTGCCACCACAGATGAATGTCGAG CATTCTGGGTAGTTTAGTCTTATAACCAGCTGTCTTGCCTAGT |
| | reTALEN-CCR5-11 | TTAAAAACCTATTGATGTATAAAACAGTTTGCATTCATGGAGGGTGA CTAAATACATTCTAGGACTTTATAAAAGATCACTTTTTATTTA |
| | reTALEN-CCR5-12 | GACATCTACCTGCTCAACCTGGCCATCTCTGACCTGTTTTTCCTATTT ACTGTCCCCTTCTGGGCTCACTATGCTGCCGCCCAGTGGGAC |
| | reTALEN-CCR5-13 | TCATCCTCCTGACAATCGATAGGTACCTGGCTGTCGTCCATGCTACG TTTGCTTTAAAAGCCAGGACGGTCACCTTTGGGGTGGTGACAA |
| | reTALEN-CCR5-14 | GGCTGGTCCTGCCGCTGCTTGTCATGGTCATCTGCTACTCGGGAGAC CTAAAAACTCTGCTTCGGTGTCGAAATGAGAAGAAGAGGCACA |
| | reTALEN-CCR5-15 | GGCAAGCCTTGGGTCATACTGCCCCCGCGAGGCCACATTGGCAAGTC AGCAAGGGTGTTCAACTTCCAGACTTGGCCATGGAGAAGACAT |

EXAMPLE VII

Amplicon Library Preparation of the Targeting Regions

Cells were harvested 6 days after nucleofection and 0.1 μl prepGEM tissue protease enzyme (ZyGEM) and 1 μl prepGEM gold buffer (ZyGEM) were added to 8.9 μl of the 2~5×105 cells in the medium. 1 ul of the reactions were then added to 9 μl of PCR mix containing 5 ul 2×KAPA Hifi Hotstart Readymix (KAPA Biosystems) and 100 nM corresponding amplification primer pairs. Reactions were incubated at 95° C. for 5 min followed by 15 cycles of 98° C., 20 s; 65° C., 20 s and 72° C., 20 s. To add the Illumina sequence adaptor used, 5 μl reaction products were then added to 20 μl of PCR mix containing 12.5 μl 2×KAPA HIFI Hotstart Readymix (KAPA Biosystems) and 200 nM primers carrying Illumina sequence adaptors. Reactions were incubated at 95° C. for 5 min followed by 25 cycles of 98° C., 20 s; 65° C., 20 s and 72° C., 20 s. PCR products were purified by QIAquick PCR purification kit, mixed at roughly the same concentration, and sequenced with MiSeq Personal Sequencer. The PCR primers are listed in Table 5 below.

TABLE 5

CCR5 targeting site PCR primer sequences (SEQ ID NOs: 161-221)

| # targeting in CCR5 | name | primer sequence |
|---|---|---|
| 1 | site1-F1 | ACACTCTTTCCCTACACGACGCTCTTCCGATCTCGTGATTTT GCAGTGTGCGTTACTCC |
| | site1-F2 | ACACTCTTTCCCTACACGACGCTCTTCCGATCTACATCGTTT GCAGTGTGCGTTACTCC |
| | site1-F3 | ACACTCTTTCCCTACACGACGCTCTTCCGATCTGCCTAATTT GCAGTGTGCGTTACTCC |
| | site1-F4 | ACACTCTTTCCCTACACGACGCTCTTCCGATCTTGGTCATTT GCAGTGTGCGTTACTCC |
| | site1-R | CTCGGCATTCCTGCTGAACCGCTCTTCCGATCTCCAAGCAA CTAAGTCACAGCA |

TABLE 5-continued

CCR5 targeting site PCR primer sequences (SEQ ID NOs: 161-221)

| # targeting in CCR5 | name | primer sequence |
|---|---|---|
| 2 | Site2-F1 | ACACTCTTTCCCTACACGACGCTCTTCCGATCTCGTGATATGAGGAAATGGAAGCTTG |
|  | Site2-F2 | ACACTCTTTCCCTACACGACGCTCTTCCGATCTACATCGATGAGGAAATGGAAGCTTG |
|  | Site2-F3 | ACACTCTTTCCCTACACGACGCTCTTCCGATCTGCCTAAATGAGGAAATGGAAGCTTG |
|  | Site2-F4 | ACACTCTTTCCCTACACGACGCTCTTCCGATCTTGGTCAATGAGGAAATGGAAGCTTG |
|  | Site2-R | CTCGGCATTCCTGCTGAACCGCTCTTCCGATCTCATTAGGGTATTGGAGGA |
| 3 | site3-F1 | ACACTCTTTCCCTACACGACGCTCTTCCGATCTCGTGATAATCCTCCCAACAACTCAT |
|  | site3-F2 | ACACTCTTTCCCTACACGACGCTCTTCCGATCTACATCGAATCCTCCCAACAACTCAT |
|  | site3-F3 | ACACTCTTTCCCTACACGACGCTCTTCCGATCTGCCTAAAATCCTCCCAACAACTCAT |
|  | site3-F4 | ACACTCTTTCCCTACACGACGCTCTTCCGATCTTGGTCAAATCCTCCCAACAACTCAT |
|  | site3_R | CTCGGCATTCCTGCTGAACCGCTCTTCCGATCTCCCAATCCTACAGAGGCAG |
| 4 | site4-F1 | ACACTCTTTCCCTACACGACGCTCTTCCGATCTCGTGATAAGCCAAAGCTTTTTATTC |
|  | site4-F2 | ACACTCTTTCCCTACACGACGCTCTTCCGATCTACATCGAAGCCAAAGCTTTTTATTC |
|  | site4-F3 | ACACTCTTTCCCTACACGACGCTCTTCCGATCTGCCTAAAAGCCAAAGCTTTTTATTC |
|  | site4-F4 | ACACTCTTTCCCTACACGACGCTCTTCCGATCTTGGTCAAAGCCAAAGCTTTTTATTC |
|  | site4_R | ACACTCTTTCCCTACACGACGCTCTTCCGATCTAAGCCAAAGCTTTTTATTCT |
| 5 | site5-F1 | ACACTCTTTCCCTACACGACGCTCTTCCGATCTCGTGATATCTTGTGGCTCGGGAGTAG |
|  | site5-F2 | ACACTCTTTCCCTACACGACGCTCTTCCGATCTACATCGATCTTGTGGCTCGGGAGTAG |
|  | site5-R | CTCGGCATTCCTGCTGAACCGCTCTTCCGATCTTGGCAGGATTCTTCACTCCA |
| 6 | site6-F1 | ACACTCTTTCCCTACACGACGCTCTTCCGATCTCGTGATCTATTTTGTTGCCCTTCAAA |
|  | site6-F2 | ACACTCTTTCCCTACACGACGCTCTTCCGATCTACATCGCTATTTTGTTGCCCTTCAAA |
|  | site6-R | CTCGGCATTCCTGCTGAACCGCTCTTCCGATCTAACCTGAACTTGACCATATACT |
| 7 | site7-F1 | ACACTCTTTCCCTACACGACGCTCTTCCGATCTCGTGATCAGCTGAGAGGTTACTTACC |
|  | site7-F2 | ACACTCTTTCCCTACACGACGCTCTTCCGATCTACATCGCAGCTGAGAGGTTACTTACC |
|  | site7-R | CTCGGCATTCCTGCTGAACCGCTCTTCCGATCTAATGATTTAACTCCACCCTC |
| 8 | site8-F1 | ACACTCTTTCCCTACACGACGCTCTTCCGATCTCGTGATACTCCACCCTCCTTCAAAAGA |
|  | site8-F2 | ACACTCTTTCCCTACACGACGCTCTTCCGATCTACATCGACTCCACCCTCCTTCAAAAGA |
|  | site8-R | CTCGGCATTCCTGCTGAACCGCTCTTCCGATCTTGGTGTTTGCCAAATGTCT |
| 9 | site9_F1 | ACACTCTTTCCCTACACGACGCTCTTCCGATCTCGTGATGGGCACATATTCAGAAGGCA |
|  | site9_F2 | ACACTCTTTCCCTACACGACGCTCTTCCGATCTACATCGGGGCACATATTCAGAAGGCA |
|  | site9_R | CTCGGCATTCCTGCTGAACCGCTCTTCCGATCTAGTGAAAGACTTTAAAGGGAGCA |
| 10 | site10-F1 | ACACTCTTTCCCTACACGACGCTCTTCCGATCTCGTGATCACAATTAAGAGTTGTCATA |
|  | site10-F2 | ACACTCTTTCCCTACACGACGCTCTTCCGATCTACATCGCACAATTAAGAGTTGTCATA |
|  | site10-R | CTCGGCATTCCTGCTGAACCGCTCTTCCGATCTCTCAGCTAGAGCAGCTGAAC |

TABLE 5-continued

CCR5 targeting site PCR primer sequences (SEQ ID NOs: 161-221)

| # targeting in CCR5 | name | primer sequence |
|---|---|---|
| 11 | site11-F1 | CTCGGCATTCCTGCTGAACCGCTCTTCCGATCTGACACTTG ATAATCCATC |
|  | site11-F2 | ACACTCTTTCCCTACACGACGCTCTTCCGATCTACATCGTCA ATGTAGACATCTATGTAG |
|  | site11-R | ACACTCTTTCCCTACACGACGCTCTTCCGATCTCGTGATTCA ATGTAGACATCTATGTAG |
| 12 | site12-F1 | ACACTCTTTCCCTACACGACGCTCTTCCGATCTCGTGATACT GCAAAAGGCTGAAGAGC |
|  | site12-F2 | ACACTCTTTCCCTACACGACGCTCTTCCGATCTACATCGACT GCAAAAGGCTGAAGAGC |
|  | site12-F3 | ACACTCTTTCCCTACACGACGCTCTTCCGATCTGCCTAAACT GCAAAAGGCTGAAGAGC |
|  | site12-F4 | ACACTCTTTCCCTACACGACGCTCTTCCGATCTTGGTCAACT GCAAAAGGCTGAAGAGC |
|  | site12-R | CTCGGCATTCCTGCTGAACCGCTCTTCCGATCTGCCTATAA AATAGAGCCCTGTCAA |
| 13 | site13-F1 | ACACTCTTTCCCTACACGACGCTCTTCCGATCTCGTGATCTC TATTTTATAGGCTTCTTC |
|  | site13-F2 | ACACTCTTTCCCTACACGACGCTCTTCCGATCTACATCGCTC TATTTTATAGGCTTCTTC |
|  | site13-R | CTCGGCATTCCTGCTGAACCGCTCTTCCGATCTAGCCACCA CCCAAGTGATC |
| 14 | site14-F1 | ACACTCTTTCCCTACACGACGCTCTTCCGATCTACATCGTTC CAGACATTAAAGATAGTC |
|  | site14-F2 | ACACTCTTTCCCTACACGACGCTCTTCCGATCTCGTGATTTC CAGACATTAAAGATAGTC |
|  | site14-R | CTCGGCATTCCTGCTGAACCGCTCTTCCGATCTAATCATGA TGGTGAAGATAAG |
| 15 | site15-F1 | ACACTCTTTCCCTACACGACGCTCTTCCGATCTCGTGATCCG GCAGAGACAAACATTAAA |
|  | site15-F2 | ACACTCTTTCCCTACACGACGCTCTTCCGATCTCCGGCAGA GACAAACATTAAA |
|  | site15-R | CTCGGCATTCCTGCTGAACCGCTCTTCCGATCTAGCTAGGA AGCCATGGCAAG |
| illumina adaptor | PE-PCR-F | AATGATACGGCGACCACCGAGATCTACACTCTTTCCCTACA cgac*g*c |
|  | PE-PCR-R | CAAGCAGAAGACGGCATACGAGATCGGTCTCGGCATTCCT GCTGAACc*g*c |
| 3 | site3-M-F | ACACTCTTTCCCTACACGACGCTCTTCCGATCTAGTGCATA GTATGTGCTAGATGCTG |

Multiplex sequencing PCR primer

| | | |
|---|---|---|
|  | site3-M-R | GTGACTGGAGTTCAGACGTGTGCTCTTCCGATCTTGATCTC TAAGAAGGCAAATGAGAC |
| illumina adaptor | Index-PCR | CAAGCAGAAGACGGCATACGAGATN1N2N3N4N5N6GTGAC TGGAGTTCAGACGTGTGCTCTTCCGATCT |
|  | universal-PCR | AATGATACGGCGACCACCGAGATCTACACTCTTTCCCTACA CGACGCTCTTCCGATCT |

*index-PCR primers are purchased from epicentre (ScriptSeq ™Index PCR Primers)

EXAMPLE VIII

Genome Editing Assessment System (GEAS)

Next generation sequencing has been utilized to detect rare genomic alterations. See references 27-30 hereby incorporated by reference in their entireties. To enable wide use of this approach to quickly assess HDR and NHEJ efficiency in hiPSCS, software was created, referred to as a "pipeline", to analyze the genome engineering data. This pipeline is integrated in one single Unix module, which uses different tools such as R, BLAT, and FASTX Toolkit.

Barcode splitting: Groups of samples were pooled together and sequenced using MiSeq 150 bp paired end (PE150) (Illumina Next Gen Sequencing), and later separated based on DNA barcodes using FASTX Toolkit.

Quality filtering: Nucleotides with lower sequence quality (phred score<20) were trimmed. After trimming, reads shorter than 80 nucleotides were discarded.

Mapping: BLAT was used to map the paired reads independently to the reference genome and .psl files were generated as output.

Indel calling: Indels were defined as the full length reads containing 2 blocks of matches in the alignment. Only reads following this pattern in both paired end reads were considered. As a quality control, the indel reads were required to possess minimal 70 nt matching with the reference genome and both blocks to be at least 20 nt long. Size and position of indels were calculated by the positions of each block to the reference genome. Non-homologous end joining (NHEJ) has been estimated as the percentage of reads containing indels (see equation 1 below). The majority of NHEJ events have been detected at the targeting site vicinity.

Homology directed recombination (HDR) efficiency: Pattern matching (grep) within a 12 bp window centering over DSB was used to count specific signatures corresponding to reads containing the reference sequence, modifications of the reference sequence (2 bp intended mismatches), and reads containing only 1 bp mutation within the 2 bp intended mismatches (see equation 1 below).

Equation 1. Estimation of NHEJ and HDR
A=reads identical to the reference: XXXXXABXXXXX
B=reads containing 2 bp mismatch programmed by ssODN: XXXXXabXXXXX
C=reads containing only 1 bp mutation in the target site: such as XXXXXaBXXXXX or XXXXXAbXXXXX
D=reads containing indels as described above $$NHEJ \text{ efficiency} = \left(100 \times \frac{D}{A+B+C+D}\right)\%$$

$$HDR \text{ efficiency} = \left(100 \times \frac{E}{A+B+C+D}\right)\%$$

EXAMPLE IX

Genotype Screening of Colonized hiPSCs

Human iPS cells on feeder-free cultures were pre-treated with mTesr-1 media supplemented with SMC4 (5 uM thiazovivin, 1 uM CHIR99021, 0.4 uM PD0325901, 2 uM SB431542) (see reference 23 hereby incorporated by reference in its entirety for at least 2 hrs prior to FACS sorting. Cultures were dissociated using Accutase (Millipore) and resuspended in mTesr-1 media supplemented with SMC4 and the viability dye ToPro-3 (Invitrogen) at concentration of 1~2 X107/mL. Live hiPS cells were single-cell sorted using a BD FACSAria II SORP UV (BD Biosciences) with 100 um nozzle under sterile conditions into 96-well plates coated with irradiated CF-1 mouse embryonic fibroblasts (Global Stem). Each well contained hES cell medium (see reference 31 hereby incorporated by reference in its entirety) with 100 ng/ml recombinant human basic Fibroblast Growth Factor (bFGF) (Millipore) supplemented with SMC4 and 5 ug/ml fibronectin (Sigma). After sorting, plates were centrifuged at 70×g for 3 min Colony formation was seen 4 days post sorting, and the culture media was replaced with hES cell medium with SMC4. SMC4 can be removed from hES cell medium 8 days after sorting.

A few thousand cells were harvested 8 days after Fluorescence-activated cell sorting (FACS) and 0.1 ul prepGEM tissue protease enzyme (ZyGEM) and 1 ul prepGEM gold buffer (ZyGEM) were added to 8.9 µl of cells in the medium. The reactions were then added to 40 µl of PCR mix containing 35.5 ml platinum 1.1× Supermix (Invitrogen), 250 nM of each dNTP and 400 nM primers. Reactions were incubated at 95° C. for 3 min followed by 30 cycles of 95° C., 20 s; 65° C., 30 s and 72° C., 20 s. Products were Sanger sequenced using either one of the PCR primers in Table 5 and sequences were analyzed using DNASTAR (DNASTAR).

EXAMPLE X

Immunostaining and Teratoma Assays of hiPSCs

Cells were incubated in the KnockOut DMEM/F-12 medium at 37° C. for 60 minutes using the following antibody: Anti-SSEA-4 PE (Millipore) (1:500 diluted); Tra-1-60 (BD Pharmingen) (1:100 diluted). After the incubation, cells were washed three times with KnockOut DMEM/F-12 and imaged on the Axio Observer Z.1 (ZIESS).

To conduct teratoma formation analysis, human iPSCs were harvested using collagenase type IV (Invitrogen) and the cells were resuspended into 200 µl of Matrigel and injected intramuscularly into the hind limbs of Rag2gamma knockout mice. Teratomas were isolated and fixed in formalin between 4-8 weeks after the injection. The teratomas were subsequently analyzed by hematoxylin and eosin staining.

EXAMPLE XI

Targeting Genomic Loci in Human Somatic Cells and Human Stem Cells Using reTALENS According to certain aspects, TALEs known to those of skill in the art are modified or re-coded to eliminate repeat sequences. Such TALEs suitable for modification and use in the genome editing methods in viral delivery vehicles and in various cell lines and organisms described herein are disclosed in references 2, 7-12 hereby incorporated by reference herein in their entireties. Several strategies have been developed to assemble the repetitive TALE RVD array sequences (see references 14 and 32-34 hereby incorporated by reference herein in their entireties. However, once assembled, the TALE sequence repeats remain unstable, which limits the wide utility of this tool, especially for viral gene delivery vehicles (see references 13 and 35 hereby incorporated by reference herein in their entireties. Accordingly, one aspect of the present disclosure is directed to TALEs lacking repeats, such as completely lacking repeats. Such a re-coded TALE is advantageous because it enables faster and simpler synthesis of extended TALE RVD arrays.

To eliminate repeats, the nucleotide sequences of TALE RVD arrays were computationally evolved to minimize the number of sequence repeats while maintaining the amino acid composition. Re-coded TALE (Re-TALEs) encoding 16 tandem RVD DNA recognition monomers, plus the final half RVD repeat, are devoid of any 12 bp repeats (see FIG. 5a). Notably, this level of recoding is sufficient to allow PCR amplification of any specific monomer or sub-section from a full-length re-TALE construct (see FIG. 5b). The improved design of re-TALEs may be synthesized using standard DNA synthesis technology (see reference 36 hereby incorporated by reference in its entirety without incurring the additional costs or procedures associated with repeat-heavy sequences. Furthermore, the recoded sequence design allows efficient assembly of re-TALE constructs using a modified isothermal assembly reaction as described in the methods herein and with reference to FIG. 6.

Genome editing NGS data was statistically analyzed as follows. For HDR specificity analysis, an exact binomial test was used to compute the probabilities of observing various numbers of sequence reads containing the 2 bp mismatch. Based on the sequencing results of 10 bp windows before and after the targeting site, the maximum base change rates of the two windows (P1 and P2) were estimated. Using the null hypothesis that the changes of each of the two target by were independent, the expected probability of observing 2 bp mismatch at the targeting site by chance as the product of these two probabilities (P1*P2) was computed. Given a dataset containing N numbers of total reads and n number of HDR reads, we calculated the p-value of the observed HDR efficiency was calculated. For HDR sensitivity analysis, the ssODN DNA donors contained a 2 bp mismatch against the targeting genome, which made likely the co-presence of the base changes in the two target by if the ssODN was incorporated into the targeting genome. Other non-intended observed sequence changes would not likely change at the same time. Accordingly, non-intended changes were much less interdependent. Based on these assumptions, mutual information (MI) was used to measure the mutual dependence of simultaneous two base pair changes in all other pairs of positions, and the HDR detection limit was estimated as the smallest HDR where MI of the targeting 2 bp site is higher than MI of all the other position pairs. For a given experiment, HDR reads with intended 2 bp mismatch from the original fastq file were identified and a set of fastq files with diluted HDR efficiencies were simulated by systematically removing different numbers of HDR reads from the original data set. Mutual information (MI) was computed between all pairs of positions within a 20 bp window centered on the targeting site. In these calculations, the mutual information of the base composition between any two positions is computed. Unlike the HDR specificity measure described above, this measure does not assess the tendency of position pairs to change to any particular pairs of target bases, only their tendency to change at the same time. (see FIG. 8A). Table 6 shows HDR and NHEJ efficiency of re-TALEN/ssODN targeting CCR5 and NHEL efficiency of Cas9-gRNA. We coded our analysis in R and MI was computed using the package infotheo.

domizing the position of the epigenetic parameter (N=100000). Observed correlations higher than the 95th percentile, or lower than the 5th percentile of the simulated distribution were considered as potential associations.

Figure 1A:
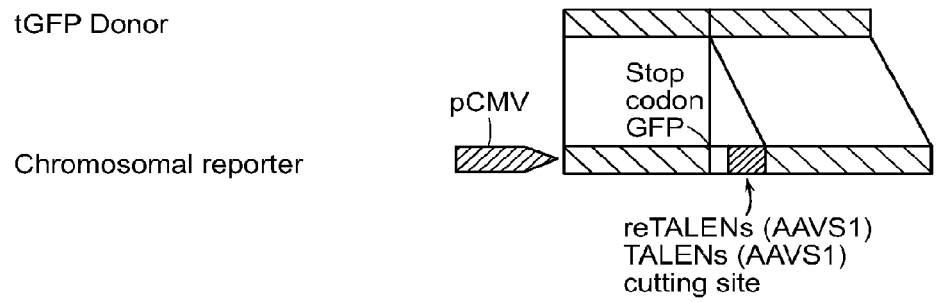
FIG. 1 is directed to functional tests of re-TALENs in human somatic and stem cells.
Figure 1B:
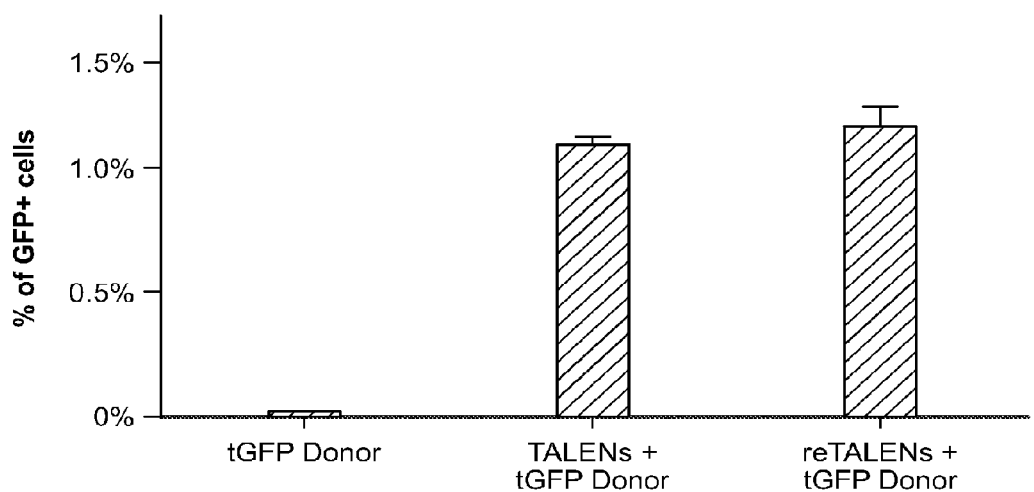
Figure 1B:
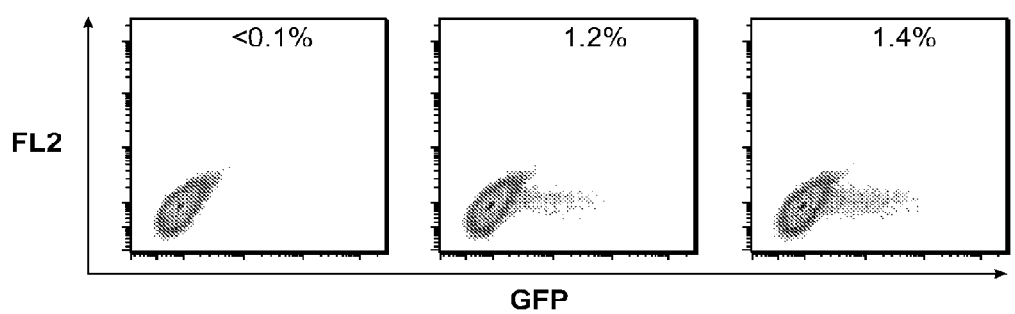
Figure 1C:
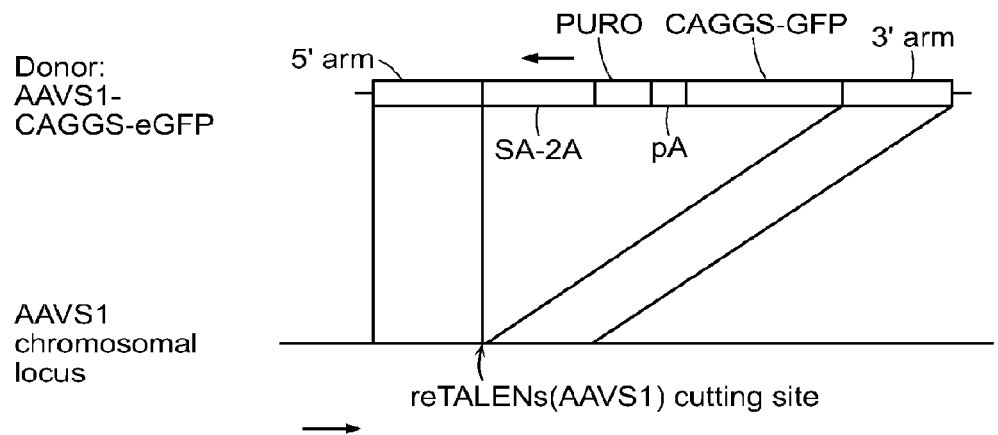
Figure 1D:
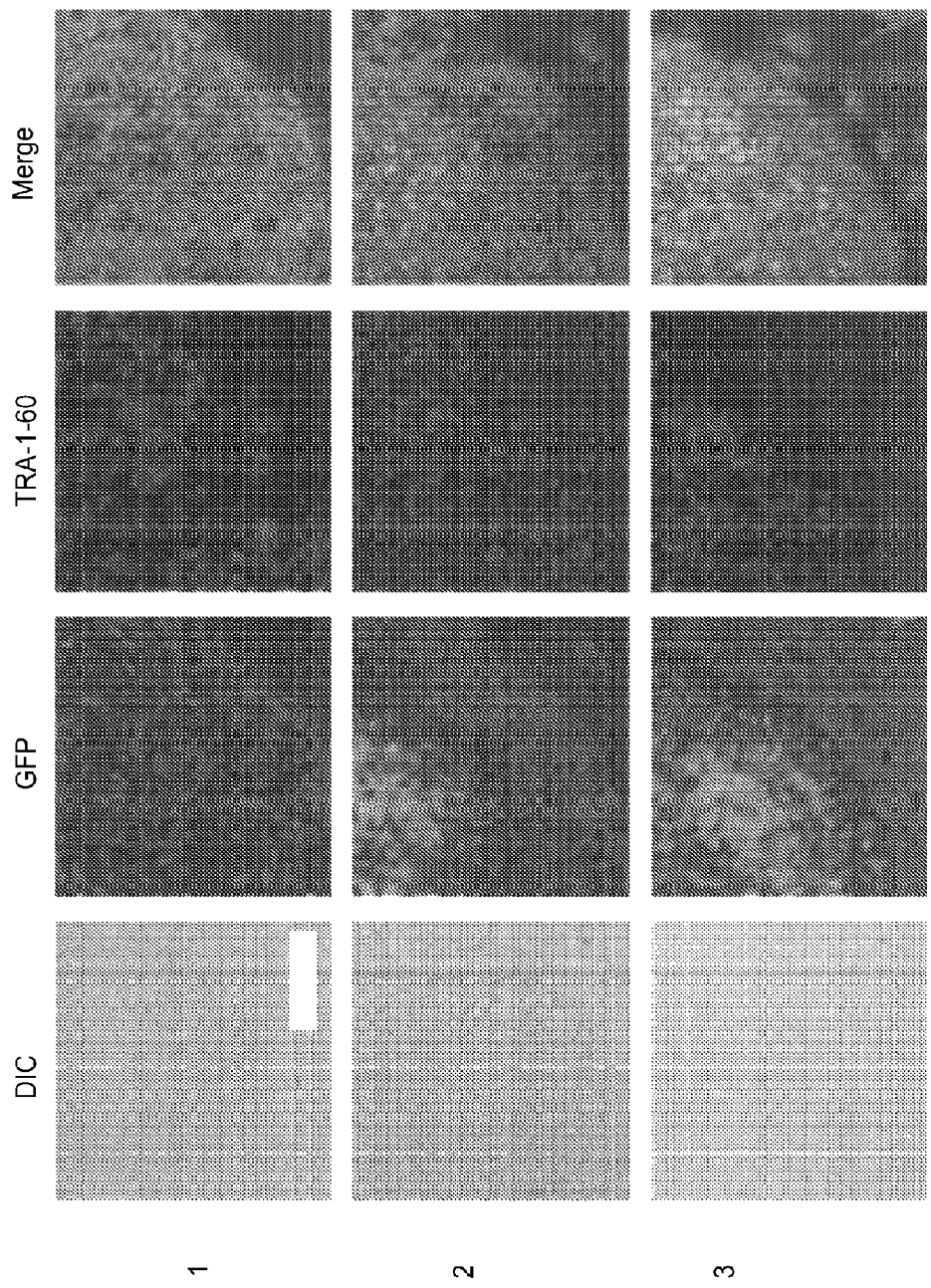
Figure 1E:
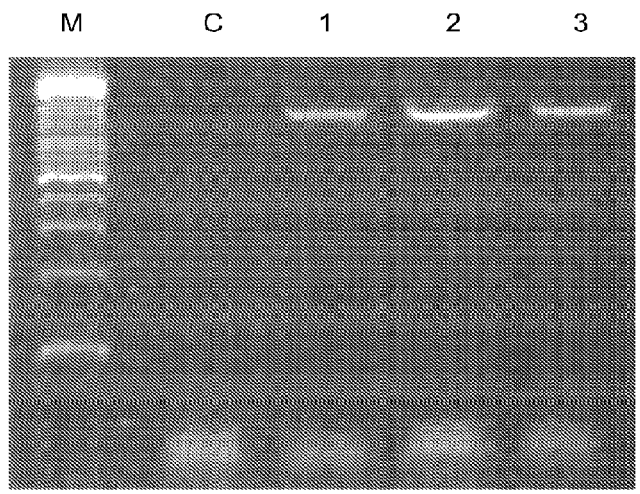
Figure 1F:
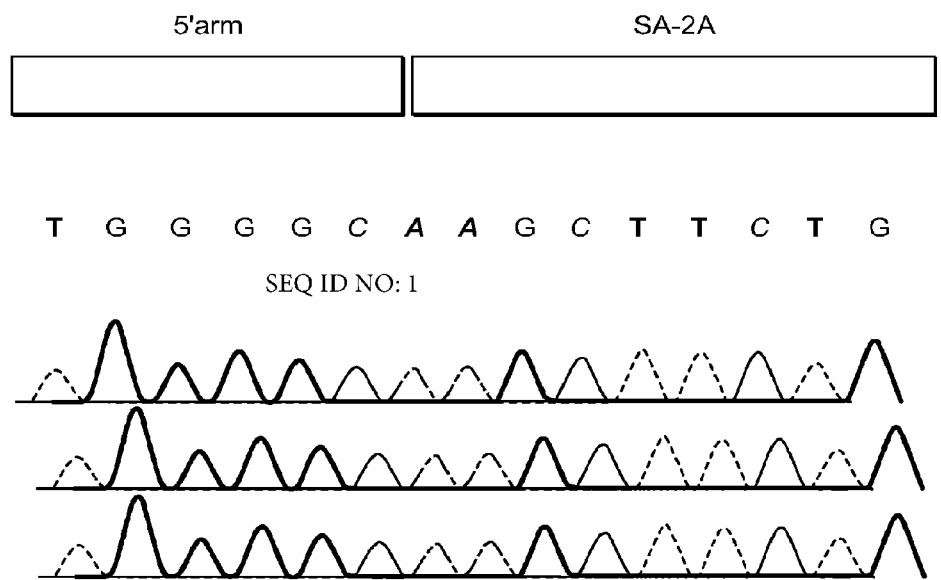

The function of reTALEN in comparison with the corresponding non-recoded TALEN in human cells was determined A HEK 293 cell line containing a GFP reporter cassette carrying a frame-shifting insertion was used as described in reference 37 hereby incorporated by reference in its entirety. See also FIG. 1a. Delivery of TALENs or reTALENs targeting the insertion sequence, together with a promoter-less GFP donor construct, leads to DSB-induced HDR repair of the GFP cassette, so that GFP repair efficiency can be used to evaluate the nuclease cutting efficiency. See reference 38 hereby incorporated by reference in its entirety. reTALENs induced GFP repair in 1.4% of the transfected cells, similar to that achieved by TALENs (1.2%) (see FIG. 1b). The activity of reTALENs at the AAVS1 locus in PGP1 hiPSCs was tested (see FIG. 1c) and successfully recovered cell clones containing specific insertions (see FIG. 1d,e), confirming that reTALENs are active in both somatic and pluripotent human cells.

The elimination of repeats enabled generation of functional lentivirus with a re-TALE cargo. Specifically, lentiviral particles were packaged encoding re-TALE-2A-GFP and were tested for activity of the re-TALE-TF encoded by viral particles by transfecting a mCherry reporter into a pool of lenti-reTALE-2A-GFP infected 293T cells. 293T cells transduced by lenti-re-TALE-TF showed 36X reporter expression activation compared with the reporter only negative (see FIG. 7a,b,c). The sequence integrity of the re-TALE-TF in the lentiviral infected cells was checked and full-length reTALEs in all 10 of the clones tested were detected. (see FIG. 7d).

TABLE 6

| # targeting site | cell type | HDR (reTALEN) (%) | NHEJ (reTALE) (%) | HDR detection limit based on Information analysis | NHEJ (Cas9-gRNA) | HDR (Cas9-gRNA) |
|---|---|---|---|---|---|---|
| 1 | PGP1-iPS | 0.06% | 0.80% | 0.04% | 0.58% | 0.38% |
| 2 | PGP1-iPS | 0.48% | 0.26% | 0.01% | 16.02% | 3.71% |
| 3 | PGP1-iPS | 1.71% | 0.07% | 0.03% | 3.44% | 3.20% |
| 4 | PGP1-iPS | 0.02% | 1.20% | 0.02%* | 1.50% | 0.14% |
| 5 | PGP1-iPS | 0.80% | 0.04% | 0.00% | 3.70% | 0.39% |
| 6 | PGP1-iPS | 0.20% | 0.73% | 0.00% | 1.12% | 0.49% |
| 7 | PGP1-iPS | 0.01% | 0.15% | 0.01%* | 1.98% | 1.78% |
| 8 | PGP1-iPS | 0.03% | 0.00% | 0.00% | 1.85% | 0.03% |
| 9 | PGP1-iPS | 1.60% | 0.06% | 0.00% | 0.50% | 0.13% |
| 10 | PGP1-iPS | 0.68% | 1.25% | 0.01% | 8.77% | 1.32% |
| 11 | PGP1-iPS | 0.06% | 0.27% | 0.00% | 0.62% | 0.44% |
| 12 | PGP1-iPS | 1.60% | 0.03% | 0.04% | 0.18% | 0.99% |
| 13 | PGP1-iPS | 0.00% | 1.47% | 0.00% | 0.65% | 0.02% |
| 14 | PGP1-iPS | 0.47% | 0.13% | 0.02% | 2.50% | 0.31% |
| 15 | PGP1-iPS | 0.8 | 0.14 | 0.08% | 1.50 | 1.10% |

*The group where HDR detection limit exceeds the real HDR detected

Correlations between genome editing efficiency and epigenetic state were addressed as follows. Pearson correlation coefficients were computed to study possible associations between epigenetic parameters (DNase I HS or nucleosome occupancy) and genome engineering efficiencies (HDR, NHEJ). Dataset of DNAaseI Hypersensitivity was downloaded from UCSC genome browser. hiPSCs DNase I HS: /gbdb/hg19/bbi/wgEncodeOpenChromDnaseIpsnihi7Sig.bigWig To compute P-values, the observed correlation was compared to a simulated distribution which was built by ran-

EXAMPLE XII

Comparison of ReTALEs and Cas9-gRNA Efficiency in hiPSCs with Genome Editing Assessment System (GEAS)

To compare the editing efficiencies of re-TALENs versus Cas9-gRNA in hiPSCs, a next-generation sequencing platform (Genome Editing Assessment System) was developed to identify and quantify both NHEJ and HDR gene editing events. A re-TALEN pair and a Cas9-gRNA were designed and constructed, both targeting the upstream region of CCR5 (re-TALEN, Cas9-gRNA pair #3 in Table 3), along with a 90 nt ssODN donor identical to the target site except for a 2 bp mismatch (see FIG. 2a). The nuclease constructs and donor ssODN were transfected into hiPSCs. To quantitate the gene editing efficiency, paired-end deep sequencing on the target genomic region was conducted 3 days after transfection. HDR efficiency was measured by the percentage of reads containing the precise 2 bp mismatch. NHEJ efficiency was measured by the percentage of reads carrying indels.

Delivery of the ssODN alone into hiPSCs resulted in minimal HDR and NHEJ rates, while delivery of the re-TALENs and the ssODN led to efficiencies of 1.7% HDR and 1.2% NHEJ (see FIG. 2b). The introduction of the Cas9-gRNA with the ssODN led to 1.2% HDR and 3.4% NHEJ efficiencies. Notably, the rate of genomic deletions and insertions peaked in the middle of the spacer region between the two reTALENs binding site, but peaked 3-4 bp upstream of the Protospacer Associated Motif (PAM) sequence of Cas9-gRNA targeting site (see FIG. 2b), as would be expected since double stranded breaks take place in these regions. A median genomic deletion size of 6 bp and insertion size of 3 bp generated by the re-TALENs was observed and a median deletion size of 7 bp and insertion of 1 bp by the Cas9-gRNA was observed (see FIG. 2b), consistent with DNA lesion patterns usually generated by NHEJ (see reference 4 hereby incorporated by reference in its entirety.) Several analyses of the next-generation sequencing platform revealed that GEAS can detect HDR detection rates as low as 0.007%, which is both highly reproducible (coefficient of variation between replicates=±15%*measured efficiency) and 400× more sensitive than most commonly used mismatch sensitive endonuclease assays (see FIG. 8).

re-TALEN pairs and Cas9-gRNAs targeted to fifteen sites at the CCR5 genomic locus were built to determine editing efficiency (see FIG. 2c, see Table 3). These sites were selected to represent a wide range of DNaseI sensitivities (see reference 39 hereby incorporated by reference in its entirety. The nuclease constructs were transfected with the corresponding ssODNs donors (see Table 3) into PGP1 hiPSCs. Six days after transfection, the genome editing efficiencies at these sites were profiled (Table 6). For 13 out of 15 re-TALEN pairs with ssODN donors, NHEJ and HDR was detected at levels above statistical detection thresholds, with an average NHEJ efficiency of 0.4% and an average HDR efficiency of 0.6% (see FIG. 2c). In addition, a statistically significant positive correlation (r2=0.81) was found between HR and NHEJ efficiency at the same targeting loci (P<1×10-4) (see FIG. 9a), suggesting that DSB generation, the common upstream step of both HDR and NHEJ, is a rate-limiting step for reTALEN-mediated genome editing.

In contrast, all 15 Cas9-gRNA pairs showed significant levels of NHEJ and HR, with an average NHEJ efficiency of 3% and an average HDR efficiency of 1.0% (see FIG. 2c). In addition, a positive correlation was also detected between the NHEJ and HDR efficiency introduced by Cas9-gRNA (see FIG. 9b) (r2=0.52, p=0.003), consistent with observations for reTALENs. The NHEJ efficiency achieved by Cas9-gRNA was significantly higher than that achieved by reTALENs (t-test, paired-end, P=0.02). A moderate but statistically significant correlation between NHEJ efficiency and the melting temperature of the gRNA targeting sequence was observed (see FIG. 9c) (r2=0.28, p=0.04), suggesting that the strength of base-pairing between the gRNA and its genomic target could explain as much as 28% of the variation in the efficiency of Cas9-gRNA-mediated DSB generation. Even though Cas9-gRNA produced NHEJ levels at an average of 7 times higher than the corresponding reTALEN, Cas9-gRNA only achieved HDR levels (average=1.0%) similar to that of the corresponding reTALENs (average=0.6%). Without wishing to be bound by scientific theory, these results may suggest either that the ssODN concentration at the DSB is the limiting factor for HDR or that the genomic break structure created by the Cas9-gRNA is not favorable for effective HDR. No correlation between DNaseI HS and the genome targeting efficiencies was observed for either method. (see FIG. 10).

EXAMPLE XIII

Optimization of ssODN Donor Design for HDR

Highly-performing ssODNs in hiPSCs were designed as follows. A set of ssODNs donors of different lengths (50-170 nt), all carrying the same 2 bp mismatch in the middle of the spacer region of the CCR5 re-TALEN pair #3 target sites was designed. HDR efficiency was observed to vary with ssODN length, and an optimal HDR efficiency of ~1.8% was observed with a 90 nt ssODN, whereas longer ssODNs decreased HDR efficiency (see FIG. 3a). Since longer homology regions improve HDR rates when dsDNA donors are used with nucleases (see reference 40 hereby incorporated by reference in its entirety), possible reasons for this result may be that ssODNs are used in an alternative genome repair process; longer ssODNs are less available to the genome repair apparatus; or that longer ssODNs incur negative effects that offset any improvements gained by longer homology, compared to dsDNA donors (see reference 41 hereby incorporated by reference in its entirety.) Yet, if either of the first two reasons were the case, then NHEJ rates should either be unaffected or would increase with longer ssODNs because NHEJ repair does not involve the ssODN donor. However, NHEJ rates were observed to decline along with HDR (see FIG. 3a), suggesting that the longer ssODNs present offsetting effects. Possible hypotheses would be that longer ssODNs are toxic to the cell (see reference 42 hereby incorporated by reference in its entirety), or that transfection of longer ssODNs saturates the DNA processing machinery, thereby causing decreased molar DNA uptake, and reducing the capacity of the cells to take up or express re-TALEN plasmids.

How rate of incorporation of a mismatch carried by the ssODN donor varies with its distance to the double stranded break ("DSB") was examined. A series of 90 nt ssODNs all possessing the same 2 bp mismatch (A) in the center of the spacer region of re-TALEN pair #3 was designed. Each ssODN also contained a second 2 bp mismatch (B) at varying distances from the center (see FIG. 3b). A ssODN possessing only the center 2 bp mismatch was used as a control. Each of these ssODNs was introduced individually with re-TALEN pair #3 and the outcomes were analyzed with GEAS. We found that overall HDR—as measured by the rate at which the A mismatch was incorporated (A only or A+B)—decreased as the B mismatches became farther from the center (see FIG. 3b, see FIG. 11a). The higher overall HDR rate observed when B is only 10 bp away from A may reflect a lesser need for annealing of the ssODN against genomic DNA immediately proximal to the dsDNA break.

For each distance of B from A, a fraction of HDR events only incorporated the A mismatch, while another fraction incorporated both A and B mismatches (see FIG. 3b (A only and A+B)), These two outcomes may be due to gene conversion tracts (see reference 43 hereby incorporated by reference in its entirety) along the length of the ssDNA oligo, whereby incoporation of A+B mismatches resulted from long conversion tracts that extended beyond the B mismatch, and incorporation of the A-only mismatch resulted from shorter tracts that did not reach B. Under this interpretation, a distribution of gene conversion lengths in both directions along the ssODN were estimated (see FIG. 11b). The estimated distribution implies that gene conversion tracts progressively become less frequent as their lengths increase, a result very similar to gene conversion tract distributions seen with dsDNA donors, but on a highly compressed distance scale of tens of bases for the ssDNA donor vs. hundreds of bases for dsDNA donors. Consistent with this result, an experiment with a ssODN containing three pairs of 2 bp mismatches spaced at intervals of 10 nt on either side of the central 2 bp mismatch "A" gave rise to a pattern in which A alone was incorporated 86% of the time, with multiple B mismatches incorporated at other times (see FIG. 11c). Although the numbers of B only incorporation events were too low to estimate a distribution of tract lengths less than 10 bp, it is clear that the short tract region within 10 bp of the nuclease site predominates (see FIG. 11b). Finally, in all experiments with single B mismatches, a small fraction of B-only incorporation events is seen (0.04%~0.12%) that is roughly constant across all B distances from A.

Furthermore, analysis was carried out of how far the ssODN donor can be placed from the re-TALEN-induced dsDNA break while still observing incorporation. A set of 90 nt ssODNs with central 2 bp mismatches targeting a range of larger distances (−600 bp to +400 bp) away from the re-TALEN-induced dsDNA break site were tested. When the ssODNs matched ≥40 bp away, we observed >30× lower HDR efficiencies compared to the control ssODN positioned centrally over the cut region (see FIG. 3c). The low level of incorporation that was observed may be due to processes unrelated to the dsDNA cut, as seen in experiments in which genomes are altered by a ssDNA donor alone see reference 42 hereby incorporated by reference in its entirety. Meanwhile, the low level of HDR present when the ssODN is ~40 bp away may be due to a combination of weakened homology on the mismatch-containing side of the dsDNA cut along with insufficient ssODN oligo length on the other side of the dsDNA break.

The ssODNs DNA donor design for Cas9-gRNA mediated targeting was tested. Cas9-gRNA (C2) targeting the AAVS1 locus was constructed and ssODN donors of variable orientations (Oc: complementary to the gRNA and On: non-complementary to the gRNA) and lengths (30, 50, 70, 90, 110 nt) were designed. Oc achieved better efficiency than On, with a 70 mer Oc achieving an optimal HDR rate of 1.5%. (see FIG. 3d) The same ssODN strand bias was detected using a Cas9-derived nickase (Cc: Cas9_D10A), despite the fact that the HDR efficiencies mediated by Cc with ssODN were significantly less than C2 (t-test, paired-end, P=0.02). (see FIG. 12).

EXAMPLE XIV hiPSC Clonal Isolation of Corrected Cells

GEAS revealed that re-TALEN pair #3 achieved precise genome editing with an efficiency of ~1% in hiPSCs, a level at which correctly edited cells can usually be isolated by screening clones. HiPSCs have poor viability as single cells. Optimized protocols described in reference 23 hereby incorporated by reference in its entirety along with a single-cell FACS sorting procedure was used to establish a robust platform for single hiPSCs sorting and maintenance, where hiPSC clones can be recovered with survival rates of >25%. This method was combined with a rapid and efficient genotyping system to conduct chromosomal DNA extraction and targeted genome amplification in 1-hour single tube reactions, enabling large scale genotyping of edited hiPSCs. Together, these methods comprise a pipeline for robustly obtaining genome-edited hiPSCs without selection.

Figure 4A:
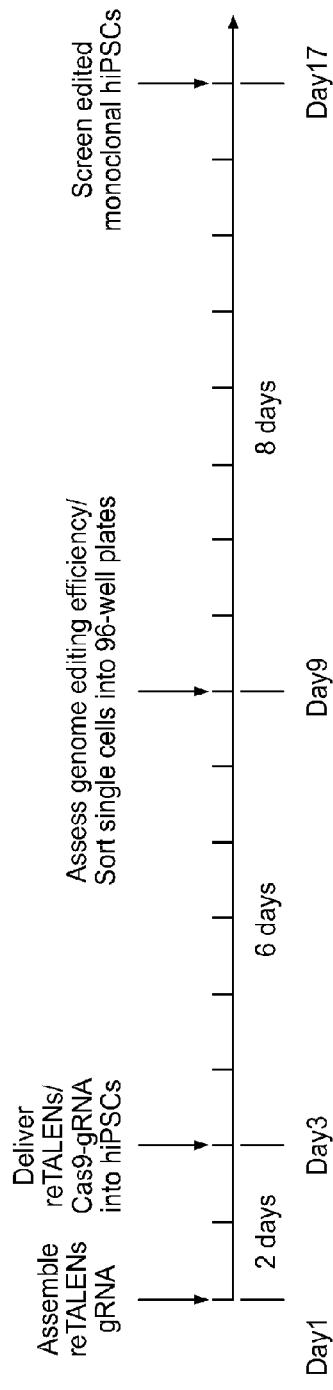
Figure 4C:
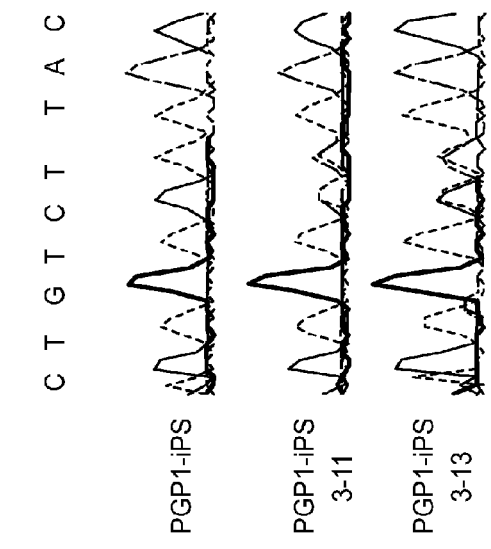
Figure 4B:
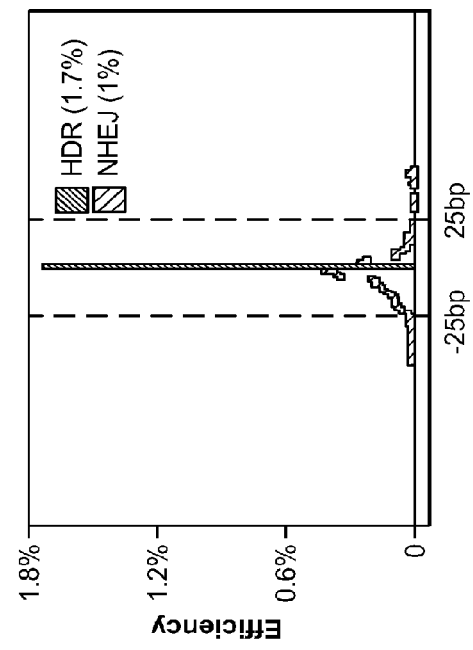
Figure 4E:
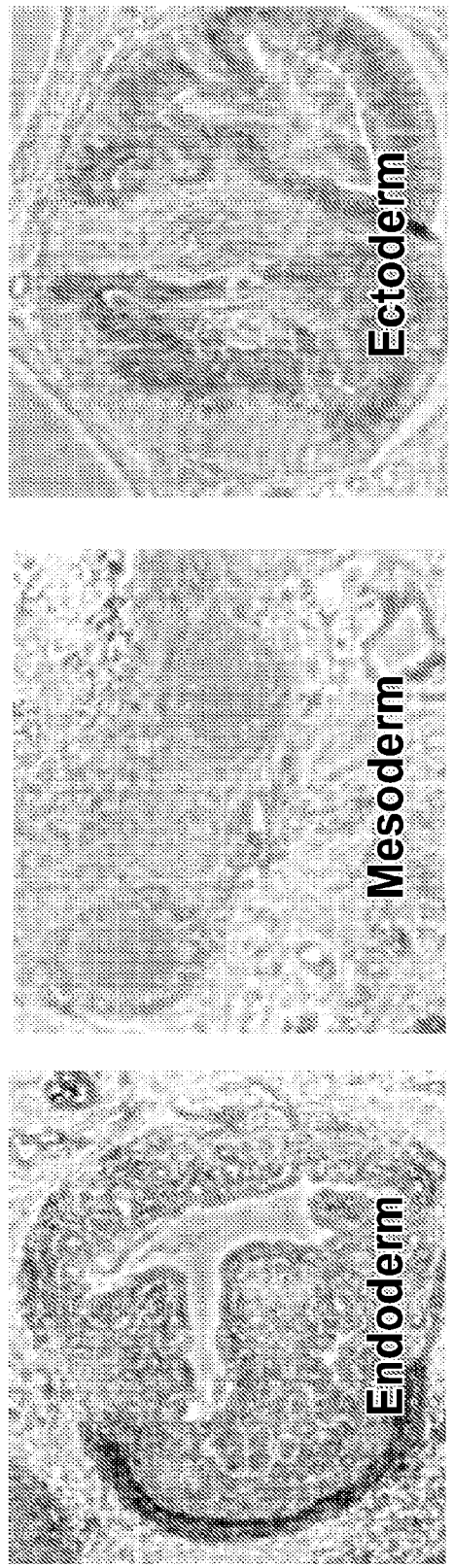

To demonstrate this system (see FIG. 4a), PGP1 hiPSCs were transfected with a pair of re-TALENs and an ssODN targeting CCR5 at site #3 (see Table 3). GEAS was performed with a portion of the transfected cells, finding an HDR frequency of 1.7% (see FIG. 4b). This information, along with the 25% recovery of sorted single-cell clones, allow estimation of obtaining at least one correctly-edited clone from five 96-well plates with Poisson probability 98% (assuming $\mu$=0.017*0.25*96*5*2). Six days after transfection, hiPSCs were FACS-sorted and eight days after sorting, 100 hiPSC clones were screened. Sanger sequencing revealed that 2 out of 100 of these unselected hiPSC colonies contained a heterozygous genotype possessing the 2 bp mutation introduced by the ssODN donor see (FIG. 4c). The targeting efficiency of 1% (1%=2/2*100, 2 mono-allelic corrected clones out of 100 cell screened) was consistent with the next-generation sequencing analysis (1.7%) (see FIG. 4b). The pluripotency of the resulting hiPSCs was confirmed with immunostaining for SSEA4 and TRA-1-60 (see FIG. 4d). The successfully targeted hiPSCs clones were able to generate mature teratomas with features of all three germ layers (see FIG. 4e).

EXAMPLE XV

Method for Continuous Cell Genome Editing

According to certain aspects, a method is provided for genome editing in cells, including a human cell, for example a human stem cell, wherein the cell is genetically modified to include a nucleic acid encoding an enzyme that forms a co-localization complex with RNA complementary to the target DNA and that cleaves the target DNA in a site specific manner. Such an enzyme includes an RNA guided DNA binding protein, such as an RNA-guided DNA binding protein of a Type II CRISPR system. An exemplary enzyme is Cas9. According to this aspect, the cell expresses the enzyme and guide RNA is provided to the cell from the media surrounding the cell. The guide RNA and the enzyme form a co-localization complex at target DNA where the enzyme cuts the DNA. Optionally, a donor nucleic acid may be present for insertion into the DNA at the cut site, for example by nonhomologous end joining or homologous recombination. According to one aspect, the nucleic acid encoding an enzyme that forms a co-localization complex with RNA complementary to the target DNA and that cleaves the target DNA in a site specific manner, such as Cas9, is under the influence of a promoter, such as the nucleic acid can be activated and silenced. Such promoters are well known to those of skill in the art. One exemplary promoter is the dox inducible promoter. According to one aspect, the cell is genetically modified by having reversibly inserted into its genome the nucleic acid encoding an enzyme that forms a co-localization complex with RNA complementary to the target DNA and that cleaves the target DNA in a site specific manner. Once inserted, the nucleic acid can be removed by use of a reagent, such as a transposase. In this manner, the nucleic acid can be easily removed after use.

According to one aspect, a continuous genome editing system in human induced pluripotent stem cells (hiPSCs) using a CRISPR system is provided. According to an exemplary aspect, the method includes use of a hiPSC line with Cas9 reversibly inserted in the genome (Cas9-hiPSCs); and gRNAs which have been modified from their native form to allow their passage from media surrounding the cells into the cells for use with the Cas9. Such gRNA has been treated with a phosphatase in a manner to remove phosphate groups. Genome editing in the cell is carried out with Cas9 by supplementing phosphatase treated gRNA in the tissue culture media. This approach enables scarless genome editing in HiPSCs with up to 50% efficiencies with single days of treatment, 2-10× times more efficient than the best efficiencies reported so far. Further, the method is easy to use and with significantly lower cellular toxicity. Embodiments of the present disclosure include single editing of hiPSCs for biological research and therapeutic applications, multiplex editing of hiPSCs for biological research and therapeutic applications, directional hiPSCs evolution and phenotype screening of hiPSCs and its derivative cells.

According to certain aspects, other cell lines and organisms described herein can be used in addition to stem cells. For example, the method described herein can be used to animal cells such as mouse or rat cells so that stable Cas9 integrated mouse cells and rat cells can be generated and tissue specific genome editing can be conducted by locally introducing phosphatase treated gRNA from media surrounding the cells. Moreover, other Cas9 derivatives can be inserted into many cell lines and organisms, and targeted genomic manipulations, such as sequence specific nicking, gene activation, suppression and epigenetic modification can be conducted.

Aspects of the present disclosure are directed to making stable hiPSCs with Cas9 inserted into the genome. Aspects of the present disclosure are directed to modifying RNA to enable entry into a cell through the cell wall and co-localization with Cas9 while avoiding the immune response of the cell. Such modified guide RNA can achieve optimal transfection efficiencies with minimal toxicity. Aspects of the present disclosure are directed to optimized genome editing in Cas9-hiPSCs using phosphatase treated gRNA. Aspects of the present disclosure include eliminating Cas9 from hiPSCs to achieve scarless genome editing, where the nucleic acid encoding Cas9 has been reversibly placed into the cell genome. Aspects of the present disclosure include biomedical engineering using hiPSCs with Cas9 inserted into the genome to create desired genetic mutations. Such engineered hiPSCs maintain pluripotency and can be successfully differentiated into various cell types, including cardiomyocyte, which fully recapitulate the phenotype of patient cell lines.

Aspects of the present disclosure include libraries of phosphatase treated gRNAs for multiplex genome editing. Aspects of the present disclosure include generating a library of PGP cell lines with each one carrying 1 to a few designated mutations in the genome, which can serve as resource for drug screening. Aspects of the present disclosure include generating PGP1 cell lines with all the retrotranselements barcoded with different sequences to track the location and activity of this element.

EXAMPLE XVI

Generating Stable hiPSCs with Cas9 inserted into the Genome

Cas9 was encoded under the dox inducible promoter and the construct was placed into a Piggybac vector which can be inserted into and removed out of the genome with the help of Piggybac transposase. PCR reaction validated the stable insertion of the vector (see FIG. 14). The inducible Cas9 expression was determined via RT-QPCR. The mRNA level of Cas9 increased 1000× after 8 hours of 1 ug/mL DOX supplementation in the culture media and the level of Cas9 mRNA dropped to normal level ~20 hours after withdrawal of the DOX. (See FIG. 15).

According to one aspect, the Cas9-hiPSC system based genome editing bypasses the transfection procedure of Cas9 plasmid/RNA, a large construct usually with <1% transfection efficiency in hiPSCs. The present Cas9-hiPSC system can serve as a platform to perform high efficient genomic engineering in human stem cells. In addition, the Cas9 cassette introduced into the hiPSCs using Piggybac system can be removed out from the genome easily upon introducing of transposases.

EXAMPLE XVII

Phosphatase Treated Guide RNA

To enable continuous genome editing on Cas9-hiPSCs, a series of modified RNA encoding gRNA were generated and supplemented into Cas9-iPS culture medium in complex with liposome. Phosphatase treated native RNA without any capping achieved the optimal HDR efficiency of 13%, 30× more than previously reported 5'Cap-Mod RNA (see FIG. 16).

According to one aspect, guide RNA is physically attached to the donor DNA. In this manner, a method is provided of coupling Cas9 mediated genomic cutting and ssODN-mediated HDR, thus stimulating sequence specific genomic editing. gRNA linked with DNA ssODN donor with optimized concentration achieved 44% HDR and unspecific NHEJ 2% (see FIG. 17). Of note, this procedure does not incurred visible toxicity as observed with nucleofection or electroporation.

According to one aspect, the present disclosure provides an in vitro engineered RNA structure encoding gRNA, which achieved high transfection efficiency, genome editing efficiency in collaboration with genomically inserted Cas9. In addition, the present disclosure provides a gRNA-DNA chimeric construct to couple a genomic cutting event with the homology directed recombination reaction.

EXAMPLE XVIII

Eliminating Reversibly Engineered Cas9 from hiPSCs to Achieve Scarless Genome Editing According to certain aspects, a Cas9 cassette is inserted into the genome of hiPSC cells using a reversible vector. Accordingly, a Cas9 cassette was reversibly inserted into the genome of hiPSC cells using a PiggyBac vector. The Cas9 cassette was removed from the genome edited hiPSCs by transfecting the cell with transposase-encoding plasmid. Accordingly, aspects of the present disclosure include use of a reversible vector, which is known to those of skill in the art. A reversible vector is one which can be inserted into a genome, for example, and then removed with a corresponding vector removal enzyme. Such vectors and corresponding vector removal enzymes are known to those of skill in the art. A screen was performed on colonized iPS cells and colonies devoid of Cas9-cassette were recovered as confirmed by PCR reaction. Accordingly, the present disclosure provides method of genome editing without affecting the rest of the genome by having a permanent Cas9 cassette present in the cell.

EXAMPLE XIX

Genome Editing in iPGP1 Cells

Research into the pathogenesis of cardiomyopathy has historically been hindered by the lack of suitable model systems. Cardiomyocyte differentiation of patient-derived induced pluripotent stem cells (iPSCs) offers one promising avenue to surmount this barrier, and reports of iPSC modeling of cardiomyopathy have begun to emerge. However, realization of this promise will require approaches to overcome genetic heterogeneity of patient-derived iPSC lines.

Cas9-iPGP1 cell lines and phosphatase treated guide RNA bound to DNA were used to generated three iPSC lines that are isogenic except for the sequence at TAZ exon 6, which was identified to carry single nucleotide deletion in Barth syndrome patients. Single round of RNA transfection achieved ~30% HDR efficiency. Modified Cas9-iPGP1 cells with desired mutations were colonized (see FIG. 18) and the cell lines were differentiated into cardiomyocyte. Cardiomyocyte derived from the engineered Cas9-iPGP1 fully recapitulated the cardiolipin, mitochondrial, and ATP deficits observed in patient-derived iPSCs and in the neonatal rat TAZ knockdown model (see FIG. 19). Accordingly, methods are provided for correcting mutations causing diseases in pluripotent cells followed by differentiation of the cells into desired cell types.

EXAMPLE XX

Materials and Methods

1. Establishment of PiggyBac Cas9 dox Inducible Stable Human iPS/ES Lines
    1. After cells reached 70% confluence pretreat the culture with ROCK inhibitor Y27632 at final concentration of 10 uM for overnight.
    2. The next day prepare the nucleofection solution by combine the 82 µl of human stem cell nucleofector solution and 18 ul supplement 1 in a sterile 1.5 ml eppendorf tube. Mix well. Incubate solution at 37° C. for 5 mins.
    3. Aspirate mTeSR1; gently rinse the cells with DPBS at 2 mL/well of a six-well plate.
    4. Aspirate the DPBS, add 2 mL/well of Versene, and put the culture back to incubator at 37° C. until they become rounded up and loosely adherent, but not detached. This requires 3-7 min
    5. Gently aspirate the Versene and add mTeSR1. Add 1 ml mTeSR1 and dislodge the cells by gently flowing mTeSR1 over them with a 1,000 uL micropipette.
    6. Collect the dislodged cells, gently triturate them into a single-cell suspension, and quantitate by hemacytometer and adjust cell density to 1 million cells per ml.
    7. Add 1 ml cell suspension to 1.5 ml eppendorf tube and centrifuge at 1100 RPM for 5 min in a bench top centrifuge.
    8. Resuspend cells in 100 µl of human stem cell nucleofector solution from Step 2.
    9. Transfer cells to a nucleofector cuvette using a 1 ml pipette tip. Add 1 µg of plasmid Transposonase and 5 ug PB Cas9 plasmids into the cell suspension in the cuvette. Mix cells and DNA by gentle swirling.
    10. Put the cuvette into the nucleofector. Programs B-016 was selected and nucleofect cells by pressing button X.
    11. Add 500 ul mTeSR1 medium with ROCK inhibitor in the cuvette after nucleofection.
    12. Asperate the nucleofected cells from the cuvette using the provided Pasteur plastic pipette. And transfer cells drop-wise into matrigel coated well of 6 well plate mTeSR1 medium with ROCK inhibitor. Incubate the cells at 37° C. overnight.
    13. Change the medium to mTesr1 the next day and after 72 hours of transfection; add puromycin at final concentration at 1 ug/ml. And the line will be set up within 7 days.

2. RNA Preparation
    1. Prepare DNA template with T7 promoter upstream of gRNA coding sequence.
    2. Purify the DNA using Mega Clear Purification and normalize the concentration.
    3. Prepare Custom NTPS mixtures for different gRNA production.

| #1 Native RNA Mix | [Final] (mM) |
|---|---|
| GTP | 7.5 |
| ATP | 7.5 |
| CTP | 7.5 |
| UTP | 7.5 |
| Total volume | |

| #2 Capped Native RNA Mix | [Final] (mM) |
|---|---|
| 3'—O—Me-m7G Cap structure analog (NEB) | 6 |
| GTP | 1.5 |
| ATP | 7.5 |
| CTP | 7.5 |
| UTP | 7.5 |
| Total volume | |

| #3 Modified RNA Mix | [Final] (mM) |
|---|---|
| GTP | 7.5 |
| ATP | 7.5 |
| 5-Me-CTP (Tri-Link) | 7.5 |
| Pseudo-UTP (Tri-Link) | 7.5 |
| Total volume | |

| #4 Capped/Modified RNA Mix | [Final] (mM) |
|---|---|
| 3'—O—Me-m7G Cap structure analog (NEB) | 6 |
| GTP | 1.5 |
| ATP | 7.5 |

-continued

| #4 Capped/Modified RNA Mix | [Final] (mM) |
|---|---|
| 5-Me-CTP (Tri-Link) | 7.5 |
| Pseudo-UTP (Tri-Link) | 7.5 |
| Total volume | |

4. Prepare the in vitro transcription mix at room temperature.

| | Amt (ul) |
|---|---|
| Custom NTPS (*Add vol/IVT rxn as indicated above) on ice | NA |
| PCR product (100 ng/ul) = 1600 ng total ([final] = 40 ng/ul) | 16 |
| Buffer X10 (MEGAscript kit from Ambion) @ RT | 4 |
| T7 Enzyme (MEGAscript kit from Ambion) | 4 |

5. Incubate for 4 hours (3-6 hrs ok) at 37° C. (thermocycler).
6. Add 2 μl Turbo DNAse (MEGAscript kit from Ambion) to each sample. Mix gently and incubate at 37° C. for 15'.
7. Purify DNAse treated reaction using MegaClear from Ambion according to the manufacturer's instructions.
8. Purify RNA using MEGAclear. (Purified RNA can be stored at −80 for several months).
9. To remove phosphate groups to avoid Toll 2 immune reaction from the host cell.

| RNA Phosphatase treatment | 1X | 12 |
|---|---|---|
| For each RNA sample | ~100 ul | NA |
| 10X Antarctic Phosphatase buffer | 11 ul | 132 |
| Antarctic Phosphatase | 2 ul | 24 |

Gently mix sample and incubate at 37° C. for 30' (30'-1 hr ok)

3. RNA Transfection
   1. Plate 10K-20K cells per 48 well without antibiotics. Cells should be 30-50% confluent for transfection.
   2. Change the cell media to with B18R (200 ng/ml), DOX (1 ug/ml), Puromycin (tug/ml) at least two hours before the transfection.
   3. Prepare the transfection reagent containing gRNA (0.5 ug~2 ug), donor DNA (0.5 ug~2 ug) and RNAiMax, incubate the mixture in rm temperature for 15 minutes and transfer to the cell.
4. Single Human iPS Cells Seed and Single Clone Pickup
   1. After 4 days of dox induction and 1 day dox withdraw, asperate the medium, rinse gently with the DPBS. add 2 mL/well of Versene, and put the culture back to incubator at 37° C. until they become rounded up and loosely adherent, but not detached. This requires 3-7 min.
   2. Gently aspirate the Versene and add mTeSR1Add 1 ml mTeSR1 and dislodge the cells by gently flowing mTeSR1 over them with a 1,000 uL micropipette.
   3. Collect the dislodged cells, gently triturate them into a single-cell suspension, and quantitate by hemacytometer and adjust cell density to 100K cells per ml.
   4. Seeding the cells into matrigel coated 10 cm dishes with mTeSR1 plus ROCK inhibitor at cell density of 50K, 100K and 400K per 10 cm dish.
5. Single Cell Formed Clones Screening
   1. After 12 days culture in 10 cm dish and clones are big enough to be identified by naked eyes and labeled by colon marker. Do not allow clones become too big and adhere to each other.
   2. Put the 10 cm dish to the culture hood and using a P20 pipette (set at 10 ul) with filter tips. Aspirate 10 ul medium for one well of 24 well plates. Pick up clone by scratching the clone into small pieces and transfer to one well of 24 well plate. Each filter tip for each clone.
   3. After 4-5 days the clones inside one well of 24 well plate become big enough to split.
   4. Aspirate the medium and rinse with 2 mL/well DPBS.
   5. Aspirate DPBS, replace with 250 ul/well dispase (0.1 U/mL). and incubate the cells in dispase at 37° C. for 7 min
   6. Replace the dispase with 2 ml DPBS.
   7. Add 250 ul mTeSR1. Using a cell scraper to lodge off the cells and collect the cells.
   8. Transfer 125 ul cell suspension into a well of matrigel coated 24 wells plates.
   9. Transfer 125 ul cell suspension into 1.5 ml eppendorf tube for genomic DNA extraction.
6. Clone Screening
   1. Centrifuge the tube from step 7.7
   2. Aspirate the medium and add 250 ul lysis buffer per well (10 mM+TrispH7.5+(or +8.0), 10 mMEDTA, 10 mM.
   3. NaCL+10% SDS, 40 ug/mL+proteinase K (added fresh before using the buffer).
   4. Incubate at 55 overnight.
   5. PrecipitateDNA by adding 250 ul Isopropanol.
   6. Spin for 30 minutes at highest speed. Wash with 70% ethanol.
   7. Gently remove ethanol. Air dry for 5 min
   8. Resuspend gDNA with 100-200 ul dH2O.
   9. PCR amplification of the targeted genomic region with specific primers.
   10. Sanger sequencing the PCR product with respective primer.
   11. Analysis of Sanger sequence data and expansion of targeted clones.
7. Piggybac Vector Remove
   1. Repeat the Step 2.1-2.9
   2. Transfer cells to a nucleofector cuvette using a 1 ml pipette tip. Add 2 μg plasmid of Transposonase into the cell suspension in the cuvette. Mix cells and DNA by gentle swirling.
   3. Repeat the step 2.10-2.11
   4. Asperate the nucleofected cells from the cuvette using the provided Pasteur plastic pipette. And transfer cells drop-wise into matrigel coated well of 10 cm dish with mTeSR1 medium plus ROCK inhibitor. Incubate the cells at 37° C. overnight.
   5. The next day change the medium to mTesr1 and change the medium every day for 4 following days.
   6. After the clones became big enough pick up 20-50 clones and seeding into 24 well.
   7. Genotype the clones with PB Cas9 PiggyBac vector primers and expansion negative clones.

REFERENCES

References are designated throughout the specification by their number below and are incorporated into the specification as if fully set forth therein. Each of the following references is hereby incorporated by reference in its entirety.
1. Carroll, D. (2011) Genome engineering with zinc-finger nucleases. Genetics, 188, 773-82.
2. Wood, A. J., Lo, T.-W., Zeitler, B., Pickle, C. S., Ralston, E. J., Lee, A. H., Amora, R., Miller, J. C., Leung, E., Meng, X., et al. (2011) Targeted genome editing across species using ZFNs and TALENs. Science (New York, N.Y.), 333, 307.
3. Perez-Pinera, P., Ousterout, D. G. and Gersbach, C. A. (2012) Advances in targeted genome editing. Current opinion in chemical biology, 16, 268-77.
4. Symington, L. S. and Gautier, J. (2011) Double-strand break end resection and repair pathway choice. Annual review of genetics, 45, 247-71.
5. Urnov, F. D., Miller, J. C., Lee, Y.-L., Beausejour, C. M., Rock, J. M., Augustus, S., Jamieson, A. C., Porteus, M. H., Gregory, P. D. and Holmes, M. C. (2005) Highly efficient endogenous human gene correction using designed zinc-finger nucleases. Nature, 435, 646-51.
6. Boch, J., Scholze, H., Schornack, S., Landgraf, A., Hahn, S., Kay, S., Lahaye, T., Nickstadt, A. and Bonas, U. (2009) Breaking the code of DNA binding specificity of TAL-type III effectors. Science (New York, N.Y.), 326, 1509-12.
7. Cell, P., Replacement, K. S., Talens, A., Type, A., Collection, C., Ccl-, A. and Quickextract, E. Genetic engineering of human pluripotent cells using TALE nucleases.
8. Mussolino, C., Morbitzer, R., Lütge, F., Dannemann, N., Lahaye, T. and Cathomen, T. (2011) A novel TALE nuclease scaffold enables high genome editing activity in combination with low toxicity. Nucleic acids research, 39, 9283-93.
9. Ding, Q., Lee, Y., Schaefer, E. A. K., Peters, D. T., Veres, A., Kim, K., Kuperwasser, N., Motola, D. L., Meissner, T. B., Hendriks, W. T., et al. (2013) Resource A TALEN Genome-Editing System for Generating Human Stem Cell-Based Disease Models.
10. Hockemeyer, D., Wang, H., Kiani, S., Lai, C. S., Gao, Q., Cassady, J. P., Cost, G. J., Zhang, L., Santiago, Y., Miller, J. C., et al. (2011) Genetic engineering of human pluripotent cells using TALE nucleases. Nature biotechnology, 29, 731-4.
11. Bedell, V. M., Wang, Y., Campbell, J. M., Poshusta, T. L., Starker, C. G., Krug Ii, R. G., Tan, W., Penheiter, S. G., Ma, A. C., Leung, A. Y. H., et al. (2012) In vivo genome editing using a high-efficiency TALEN system. Nature, 490, 114-118.
12. Miller, J. C., Tan, S., Qiao, G., Barlow, K. a, Wang, J., Xia, D. F., Meng, X., Paschon, D. E., Leung, E., Hinkley, S. J., et al. (2011) A TALE nuclease architecture for efficient genome editing. Nature biotechnology, 29, 143-8.
13. Holkers, M., Maggio, I., Liu, J., Janssen, J. M., Miselli, F., Mussolino, C., Recchia, A., Cathomen, T. and Gonçalves, M. a F. V (2012) Differential integrity of TALE nuclease genes following adenoviral and lentiviral vector gene transfer into human cells. Nucleic acids research, 10.1093/nar/gks1446.
14. Reyon, D., Tsai, S. Q., Khayter, C., Foden, J. a, Sander, J. D. and Joung, J. K. (2012) FLASH assembly of TALENs for high-throughput genome editing. Nature Biotechnology, 30, 460-465.
15. Qiu, P., Shandilya, H., D'Alessio, J. M., O'Connor, K., Durocher, J. and Gerard, G. F. (2004) Mutation detection using Surveyor nuclease. BioTechniques, 36, 702-7.
16. Mali, P., Yang, L., Esvelt, K. M., Aach, J., Guell, M., DiCarlo, J. E., Norville, J. E. and Church, G. M. (2013) RNA-guided human genome engineering via Cas9. Science (New York, N.Y.), 339, 823-6.
17. Ding, Q., Regan, S. N., Xia, Y., Oostrom, L. A., Cowan, C. A. and Musunuru, K. (2013) Enhanced Efficiency of Human Pluripotent Stem Cell Genome Editing through Replacing TALENs with CRISPRs. Cell Stem Cell, 12, 393-394.
18. Cong, L., Ran, F. A., Cox, D., Lin, S., Barretto, R., Habib, N., Hsu, P. D., Wu, X., Jiang, W., Marraffini, L. a, et al. (2013) Multiplex genome engineering using CRISPR/Cas systems. Science (New York, N.Y.), 339, 819-23.
19. Cho, S. W., Kim, S., Kim, J. M. and Kim, J.-S. (2013) Targeted genome engineering in human cells with the Cas9 RNA-guided endonuclease. Nature biotechnology, 31, 230-232.
20. Hwang, W. Y., Fu, Y., Reyon, D., Maeder, M. L., Tsai, S. Q., Sander, J. D., Peterson, R. T., Yeh, J.-R. J. and Joung, J. K. (2013) Efficient genome editing in zebrafish using a CRISPR-Cas system. Nature biotechnology, 31, 227-229.
21. Chen, F., Pruett-Miller, S. M., Huang, Y., Gjoka, M., Duda, K., Taunton, J., Collingwood, T. N., Frodin, M. and Davis, G. D. (2011) High-frequency genome editing using ssDNA oligonucleotides with zinc-finger nucleases. Nature methods, 8, 753-5.
22. Soldner, F., Laganiere, J., Cheng, A. W., Hockemeyer, D., Gao, Q., Alagappan, R., Khurana, V., Golbe, L. I., Myers, R. H., Lindquist, S., et al. (2011) Generation of isogenic pluripotent stem cells differing exclusively at two early onset Parkinson point mutations. Cell, 146, 318-31.
23. Valamehr, B., Abujarour, R., Robinson, M., Le, T., Robbins, D., Shoemaker, D. and Flynn, P. (2012) A novel platform to enable the high-throughput derivation and characterization of feeder-free human iPSCs. Scientific reports, 2, 213.
24. Sanjana, N. E., Cong, L., Zhou, Y., Cunniff, M. M., Feng, G. and Zhang, F. (2012) A transcription activator-like effector toolbox for genome engineering. Nature protocols, 7, 171-92.
25. Gibson, D. G., Young, L., Chuang, R., Venter, J. C., Iii, C. A. H., Smith, H. O. and America, N. (2009) Enzymatic assembly of DNA molecules up to several hundred kilobases. 6, 12-16.
26. Zou, J., Maeder, M. L., Mali, P., Pruett-Miller, S. M., Thibodeau-Beganny, S., Chou, B.-K., Chen, G., Ye, Z., Park, I.-H., Daley, G. Q., et al. (2009) Gene targeting of a disease-related gene in human induced pluripotent stem and embryonic stem cells. Cell stem cell, 5, 97-110.
27. Perez, E. E., Wang, J., Miller, J. C., Jouvenot, Y., Kim, K. a, Liu, O., Wang, N., Lee, G., Bartsevich, V. V, Lee, Y.-L., et al. (2008) Establishment of HIV-1 resistance in CD4+ T cells by genome editing using zinc-finger nucleases. Nature biotechnology, 26, 808-16.
28. Bhakta, M. S., Henry, I. M., Ousterout, D. G., Das, K. T., Lockwood, S. H., Meckler, J. F., Wallen, M. C., Zykovich, A., Yu, Y., Leo, H., et al. (2013) Highly active zinc-finger nucleases by extended modular assembly. Genome research, 10.1101/gr.143693.112.
29. Kim, E., Kim, S., Kim, D. H., Choi, B.-S., Choi, I.-Y. and Kim, J.-S. (2012) Precision genome engineering with programmable DNA-nicking enzymes. Genome research, 22, 1327-33.

30. Gupta, A., Meng, X., Zhu, L. J., Lawson, N. D. and Wolfe, S. a (2011) Zinc finger protein-dependent and -independent contributions to the in vivo off-target activity of zinc finger nucleases. Nucleic acids research, 39, 381-92.
31. Park, I.-H., Lerou, P. H., Zhao, R., Huo, H. and Daley, G. Q. (2008) Generation of human-induced pluripotent stem cells. Nature protocols, 3, 1180-6.
32. Cermak, T., Doyle, E. L., Christian, M., Wang, L., Zhang, Y., Schmidt, C., Baller, J. A., Somia, N. V, Bogdanove, A. J. and Voytas, D. F. (2011) Efficient design and assembly of custom TALEN and other TAL effector-based constructs for DNA targeting. Nucleic acids research, 39, e82.
33. Briggs, A. W., Rios, X., Chari, R., Yang, L., Zhang, F., Mali, P. and Church, G. M. (2012) Iterative capped assembly: rapid and scalable synthesis of repeat-module DNA such as TAL effectors from individual monomers. Nucleic acids research, 10.1093/nar/gks624.
34. Zhang, F., Cong, L., Lodato, S., Kosuri, S., Church, G. M. and Arlotta, P. (2011) LETTErs Efficient construction of sequence-specific TAL effectors for modulating mammalian transcription. 29, 149-154.
35. Pathak, V. K. and Temin, H. M. (1990) Broad spectrum of in vivo forward mutations, hypermutations, and mutational hotspots in a retroviral shuttle vector after a single replication cycle: substitutions, frameshifts, and hypermutations. Proceedings of the National Academy of Sciences of the United States of America, 87, 6019-23.
36. Tian, J., Ma, K. and Saaem, I. (2009) Advancing high-throughput gene synthesis technology. Molecular bioSystems, 5, 714-22.
37. Zou, J., Mali, P., Huang, X., Dowey, S. N. and Cheng, L. (2011) Site-specific gene correction of a point mutation in human iPS cells derived from an adult patient with sickle cell disease. Blood, 118, 4599-608.
38. Mali, P., Yang, L., Esvelt, K. M., Aach, J., Guell, M., Dicarlo, J. E., Norville, J. E. and Church, G. M. (2013) RNA-Guided Human Genome.
39. Boyle, A. P., Davis, S., Shulha, H. P., Meltzer, P., Margulies, E. H., Weng, Z., Furey, T. S. and Crawford, G. E. (2008) High-resolution mapping and characterization of open chromatin across the genome. Cell, 132, 311-22.
40. Orlando, S. J., Santiago, Y., DeKelver, R. C., Freyvert, Y., Boydston, E. a, Moehle, E. a, Choi, V. M., Gopalan, S. M., Lou, J. F., Li, J., et al. (2010) Zinc-finger nuclease-driven targeted integration into mammalian genomes using donors with limited chromosomal homology. Nucleic acids research, 38, e152.
41. Wang, Z., Zhou, Z.-J., Liu, D.-P. and Huang, J.-D. (2008) Double-stranded break can be repaired by single-stranded oligonucleotides via the ATM/ATR pathway in mammalian cells. Oligonucleotides, 18, 21-32.
42. Rios, X., Briggs, A. W., Christodoulou, D., Gorham, J. M., Seidman, J. G. and Church, G. M. (2012) Stable gene targeting in human cells using single-strand oligonucleotides with modified bases. PloS one, 7, e36697.
43. Elliott, B., Richardson, C., Winderbaum, J., Jac, A., Jasin, M. and Nickoloff, J. A. C. A. (1998) Gene Conversion Tracts from Double-Strand Break Repair in Mammalian Cells Gene Conversion Tracts from Double-Strand Break Repair in Mammalian Cells. 18.
44. Lombardo, A., Genovese, P., Beausejour, C. M., Colleoni, S., Lee, Y.-L., Kim, K. a, Ando, D., Urnov, F. D., Galli, C., Gregory, P. D., et al. (2007) Gene editing in human stem cells using zinc finger nucleases and integrase-defective lentiviral vector delivery. Nature biotechnology, 25, 1298-306.
45. Jinek, M., Chylinski, K., Fonfara, I., Hauer, M., Doudna, J. a and Charpentier, E. (2012) A programmable dual-RNA-guided DNA endonuclease in adaptive bacterial immunity Science (New York, N.Y.), 337, 816-21.
46. Shrivastav, M., De Haro, L. P. and Nickoloff, J. a (2008) Regulation of DNA double-strand break repair pathway choice. Cell research, 18, 134-47.
47. Kim, Y. G., Cha, J. and Chandrasegaran, S. (1996) Hybrid restriction enzymes: zinc finger fusions to Fok I cleavage domain. Proceedings of the National Academy of Sciences of the United States of America, 93, 1156-60.
48. Mimitou, E. P. and Symington, L. S. (2008) Sae2, Exo1 and Sgs1 collaborate in DNA double-strand break processing. Nature, 455, 770-4.
49. Doyon, Y., Choi, V. M., Xia, D. F., Vo, T. D., Gregory, P. D. and Holmes, M. C. (2010) Transient cold shock enhances zinc-finger nuclease-mediated gene disruption. Nature methods, 7, 459-60.

The invention claimed is:

1. A nucleic acid sequence encoding a modified transcription activator-like effector nuclease (TALEN) comprising SEQ ID NO:24, or a sequence having at least 90% sequence identity to SEQ ID NO: 24.

2. A plasmid including the nucleic acid sequence of claim 1.

3. A virus including the nucleic acid sequence of claim 1.

4. The virus of claim 3 being a lentivirus.

5. A cell including a nucleic acid sequence of claim 1.

6. The cell of claim 5 being a eukaryotic cell.

7. The cell of claim 5 being a yeast cell, a plant cell or an animal cell.

8. The cell of claim 5 being a somatic cell.

9. The cell of claim 5 being a stem cell.

10. The cell of claim 5 being a human stem cell.

11. A modified transcription activator-like effector nuclease (TALEN) having a TALE sequence encoded by a nucleic acid sequence comprising SEQ ID NO:24, or a sequence having at least 90% sequence identity to SEQ ID NO: 24.

12. A method of altering target DNA in a cell comprising introducing into a cell the modified transcription activator-like effector nuclease (TALEN) of claim 11 wherein the modified TALEN cleaves the target DNA and the cell undergoes nonhomologous end joining to produce altered DNA in the cell.

13. The method of claim 12 wherein the cell is a eukaryotic cell.

14. The method of claim 12 wherein the cell is a yeast cell, a plant cell or an animal cell.

15. The method of claim 12 wherein the cell is a somatic cell.

16. The method of claim 12 wherein the cell is a stem cell.

17. The method of claim 12 wherein the cell is a human stem cell.

18. The method of claim 12 comprising introducing into the cell a virus including the nucleic acid sequence, wherein the modified TALEN is expressed, and wherein the modified TALEN cleaves the target DNA to produce altered DNA in the cell.

19. The method of claim 12 further including providing a donor nucleic acid sequence within the cell wherein the modified TALEN cleaves the target DNA and the donor nucleic acid sequence is inserted into the DNA in the cell.

20. The method of claim 19 wherein the cell undergoes nonhomologous end joining to produce altered DNA in the cell.

21. The method of claim 19 wherein the cell undergoes homologous recombination to produced altered DNA in the cell.

* * * * *

UNITED STATES PATENT AND TRADEMARK OFFICE
CERTIFICATE OF CORRECTION

PATENT NO. : 9,914,939 B2
APPLICATION NO. : 14/907605
DATED : March 13, 2018
INVENTOR(S) : Church et al.

It is certified that error appears in the above-identified patent and that said Letters Patent is hereby corrected as shown below:

In the Specification

Column 1, Line 15:
Delete:
"This invention was made with government support under P50 HG003170 from the National Human Genome Research Center for Excellence in Genomic Science. The government has certain rights in the invention."

And insert:
-- This invention was made with government support under HG003170 awarded by the National Institutes of Health. The government has certain rights in the invention. --

Signed and Sealed this
Seventeenth Day of May, 2022

Katherine Kelly Vidal
*Director of the United States Patent and Trademark Office*